(12) United States Patent
Liu et al.

(10) Patent No.: US 11,155,820 B2
(45) Date of Patent: Oct. 26, 2021

(54) TARGET OF VGSC β3 PROTEIN FOR PREVENTION, TREATMENT AND DIAGNOSTIC DETECTION OF CANCERS

(71) Applicant: SHENYANG PHARMACEUTICAL UNIVERSITY, Liaoning (CN)

(72) Inventors: Yanfeng Liu, Shenyang (CN); Yong Cui, Shenyang (CN); Jinghai Zhang, Shenyang (CN)

(73) Assignee: SHENYANG PHARMACEUTICAL UNIVERSITY, Liaoning (CN)

( * ) Notice: Subject to any disclaimer, the term of this patent is extended or adjusted under 35 U.S.C. 154(b) by 279 days.

(21) Appl. No.: 15/329,128

(22) PCT Filed: May 20, 2015

(86) PCT No.: PCT/CN2015/079356
§ 371 (c)(1),
(2) Date: Jan. 25, 2017

(87) PCT Pub. No.: WO2016/011840
PCT Pub. Date: Jan. 28, 2016

(65) Prior Publication Data
US 2017/0253882 A1    Sep. 7, 2017

(30) Foreign Application Priority Data

Jul. 25, 2014  (CN) .......................... 201410359535.8

(51) Int. Cl.
| | | |
|---|---|---|
| *C07K 14/435* | (2006.01) | |
| *C12N 15/113* | (2010.01) | |
| *C07K 14/705* | (2006.01) | |
| *C07K 16/28* | (2006.01) | |
| *C07K 16/30* | (2006.01) | |
| *C12Q 1/6886* | (2018.01) | |
| *G01N 33/50* | (2006.01) | |
| *G01N 33/68* | (2006.01) | |
| *A61K 39/00* | (2006.01) | |
| *A61K 38/00* | (2006.01) | |

(52) U.S. Cl.
CPC .... *C12N 15/1138* (2013.01); *C07K 14/43522* (2013.01); *C07K 14/705* (2013.01); *C07K 16/28* (2013.01); *C07K 16/30* (2013.01); *C12Q 1/6886* (2013.01); *G01N 33/5011* (2013.01); *G01N 33/6872* (2013.01); *A61K 38/00* (2013.01); *A61K 2039/505* (2013.01); *C07K 2317/76* (2013.01); *C12N 2310/14* (2013.01); *C12Q 2600/136* (2013.01); *C12Q 2600/158* (2013.01); *G01N 2333/705* (2013.01)

(58) Field of Classification Search
CPC ............ C12N 15/1138; C12N 2310/14; C07K 14/43522; C07K 16/28; C07K 16/30; C07K 2317/76; C12Q 1/6886; C12Q 2600/136; C12Q 2600/158; G01N 33/5011; G01N 33/6872; G01N 2333/705; A61K 38/00

See application file for complete search history.

(56) References Cited

U.S. PATENT DOCUMENTS

| | | | | |
|---|---|---|---|---|
| 2005/0159378 A1* | 7/2005 | McSwiggen | ....... | A61K 49/0008 514/44 A |
| 2012/0082659 A1 | 4/2012 | Land et al. | | |

FOREIGN PATENT DOCUMENTS

WO     2000063367 A1    10/2000

OTHER PUBLICATIONS

McEwen et al, Neurosci Lett, 462:272-275, 2009.*
Shao et al, Peptides, 53:89-96, Mar. 2014.*
Zhao et al, J Cell Biochem, 112:2424-2434, 2011.*
Zhijian et al, Toxicon, 47:348-355, 2006.*
Granziero et al, Eur. J. Immunol. 1999, 29:1127-1138.*
Byers, T, CA Journal, vol. 49, No. 6, Nov./Dec. 1999.*
Pai et al, Gene Therapy 2005; 1-14.*
Ryther et al, Gene Therapy 2005; 12: 5-11.*
Schiffelers et al, Nucleic Acids Research 2004; 32: e149.*
Catterall, W.A. et al., "International Union of Pharmacology: Approaches to the Nomenclature of Voltage-Gated Ion Channels", Pharmacological Reviews, 55(4):573-574, the American Society for Pharmacology and Experimental Therapeutics (2003).
Catterall, W.A., "From Ionic Currents to Molecular Mechanisms: The Structure and Function of Voltage-Gated Sodium Channels", Neuron, 26:13-25, Cell Press (2000).
Catterall, W.A. et al., "International Union of Pharmacology. XXXIX. Compendium of Voltage-Gated Ion Channels: Sodium Channels", Pharmacological Reviews, 55(4):575-578, the American Society for Pharmacology and Experimental Therapeutics (2003).
Kaufmann, S.G. et al., "Functional Protein Expression of Multiple Sodium Channel α- and β-subunit Isoforms in Neonatal Cardiomyocytes", J. of Molecular and Cellular Cardiology, 28:261-269, Elsevier Inc. (2010).
Brackenbury, W.J. et al., "Voltage-Gated Na$^+$ Channel βI Subunit-Mediated Neurite Outgrowth Requires Fyn Kinase and Contributes to Postnatal CNS Delveopment in Vivo", Cellular/Molecular 28:3246-3256, J. of Neuroscience (2008).

(Continued)

*Primary Examiner* — J. E. Angell
(74) *Attorney, Agent, or Firm* — Potomac Law Group, PLLC

(57) ABSTRACT

The present application relates to inhibitors of VGSCβ3 protein and use thereof and methods of using the VGSCβ3 protein or an inhibitor thereof to diagnose, prevent and treat cancer, and to screen antineoplastic agents using the VGSCβ3 Protein or its regulatory sequences.

11 Claims, 15 Drawing Sheets

Specification includes a Sequence Listing.

(56) References Cited

OTHER PUBLICATIONS

Zhang, Z.N. et al., "The Voltage-Gated Na$^+$ Channel Na$_v$ 1.8 Contains an ER-Retention/Retrieval Signal Antagonized by the β3 Subunit", J. of Cell Science, 121:3243-3252, the Company of Biologists (2008).
McEwen, D.P. et al., "The Voltage-Gated Na$^+$ Channel β3 Subunit Does Not Mediate *Trans* Homophilic Cell Adhesion or Associate with the Cell Adhesion Molecule Contactin", Neurosci Lett., 462(3):272-275, Elsevier Ireland Ltd. (2009).
Roger, S. et al., "Voltage-Gated Sodium Channels: New Targets in Cancer Therapy?", Current Pharmaceutical Design 12:3681-3695, Bentham Science Publishers Ltd. (2006).
Hu, D. et al., "A Mutation in the β3 Subunit of the Cardiac Sodium Channel Associated with Brugada ECG Phenotype", Circ Cardiovasc Genet., 2(3):270-278, NIH Public Access Author Manuscript (2009).
Hummler, E. et al., "Lessons from Mouse Mutants of Epithelial Sodium Channel and Its Regulatory Proteins", J. Am Soc Nephrol, 16:3160-3166, the American Society of Nephrology (2005).
Randrianarison, N. et al., "Low Expression of the β-ENaC Subunit Impairs Lung Fluid Clearance in the Mouse", Am J Physiol Lung Cell Mo. Physiol, 294:L409-L416, American Physiological Society (2008).
Ho, C., "Differential Expression of Sodium Channel β Subunits in Dorsal Root Ganglion Sensory Neurons", J of Bio Chem, 287(18):15044-15053, the American Society for Biochemistry and Molecular Biology (2012).
Adachi, K. et al., "Identification of SCN3B as a Novel p53-Inducible Proapoptotic Gene", Oncogene, 23:7791-7798, Nature Publishing Group (2004).
Brackenbury, W.J., et al., "Na$^+$ Channel β Subunits: Overachievers of the Ion Channel Family", Frontiers in Pharmacology, 2(53):1-11, Frontiers Media SA (2011).
Cao, X.R. et al., "Mice Heterozygous for β-ENaC Deletion Have Defective Potassium Excretion", Am J Physiol Renal Physiol, 291:F107-F115, the American Physiological Society (2006).
An English translation of International Search Report for PCT/CN2015/079356 dated Aug. 28, 2015.
Brackenbury et al., "Voltage-gated Na+ channels: Potential for β subunits as therapeutic targets," Expert Opinion on Therapeutic Targets, 2008, vol. 12(9), pp. 1191-1203, Taylor & Francis Group, Oxfordshire United Kingdom.

\* cited by examiner

A

B

SEQUENCE LISTING

```
<160> NUMBER OF SEQ ID NOS: 10

<210> SEQ ID NO 1
<211> LENGTH: 215
<212> TYPE: PRT
<213> ORGANISM: Homo sapiens

<400> SEQUENCE: 1

Met Pro Ala Phe Asn Arg Leu Phe Pro Leu Ala Ser Leu Val Leu Ile
1               5                   10                  15

Tyr Trp Val Ser Val Cys Phe Pro Val Cys Val Glu Val Pro Ser Glu
            20                  25                  30

Thr Glu Ala Val Gln Gly Asn Pro Met Lys Leu Arg Cys Ile Ser Cys
        35                  40                  45

Met Lys Arg Glu Glu Val Glu Ala Thr Thr Val Val Glu Trp Phe Tyr
    50                  55                  60

Arg Pro Glu Gly Gly Lys Asp Phe Leu Ile Tyr Glu Tyr Arg Asn Gly
65                  70                  75                  80

His Gln Glu Val Glu Ser Pro Phe Gln Gly Arg Leu Gln Trp Asn Gly
                85                  90                  95

Ser Lys Asp Leu Gln Asp Val Ser Ile Thr Val Leu Asn Val Thr Leu
            100                 105                 110

Asn Asp Ser Gly Leu Tyr Thr Cys Asn Val Ser Arg Glu Phe Glu Phe
        115                 120                 125

Glu Ala His Arg Pro Phe Val Lys Thr Thr Arg Leu Ile Pro Leu Arg
    130                 135                 140

Val Thr Glu Glu Ala Gly Glu Asp Phe Thr Ser Val Val Ser Glu Ile
145                 150                 155                 160

Met Met Tyr Ile Leu Leu Val Phe Leu Thr Leu Trp Leu Leu Ile Glu
                165                 170                 175

Met Ile Tyr Cys Tyr Arg Lys Val Ser Lys Ala Glu Glu Ala Ala Gln
            180                 185                 190
```

Glu Asn Ala Ser Asp Tyr Leu Ala Ile Pro Ser Glu Asn Lys Glu Asn
        195                 200                 205

Ser Ala Val Pro Val Glu Glu
    210                 215

<210> SEQ ID NO 2
<211> LENGTH: 648
<212> TYPE: DNA
<213> ORGANISM: Homo sapiens

<400> SEQUENCE: 2
atgcctgcct tcaatagatt gtttccctg gcttctctcg tgcttatcta ctgggtcagt    60
gtctgcttcc ctgtgtgtgt ggaagtgccc tcggagacgg aggccgtgca gggcaacccc   120
atgaagctgc gctgcatctc ctgcatgaag agagaggagg tggaggccac cacggtggtg   180
gaatggttct acaggcccga ggcggtaaa gatttcctta tttacgagta tcggaatggc   240
caccaggagg tggagagccc ctttcagggg cgcctgcagt ggaatggcag caaggacctg   300
caggacgtgt ccatcactgt gctcaacgtc actctgaacg actctggcct ctacacctgc   360
aatgtgtccc gggagtttga gtttgagcg catcggccct tgtgaagac gacgcggctg   420 atccccctaa gagtcaccga ggaggctgga gaggacttca cctctgtggt ctcagaaatc   480
atgatgtaca tccttctggt cttcctcacc ttgtggctgc tcatcgagat gatatattgc   540
tacagaaagg tctcaaaagc cgaagaggca gcccaagaaa acgcgtctga ctaccttgcc   600
atcccatctg agaacaagga gaactctgcg gtaccagtgg aggaatag             648

<210> SEQ ID NO 3
<211> LENGTH: 21
<212> TYPE: DNA
<213> ORGANISM: Artificial
<220> FEATURE:
<223> OTHER INFORMATION: siRNA

<400> SEQUENCE: 3
ccugccuuca auagauucut t                                             21

<210> SEQ ID NO 4
<211> LENGTH: 21
<212> TYPE: DNA
<213> ORGANISM: Artificial
<220> FEATURE:
<223> OTHER INFORMATION: siRNA

<400> SEQUENCE: 4
acaaucuauu gaaggcaggt t                                             21

<210> SEQ ID NO 5
<211> LENGTH: 21
<212> TYPE: DNA
<213> ORGANISM: Artificial
<220> FEATURE:
<223> OTHER INFORMATION: siRNA

<400> SEQUENCE: 5
gcgguaaaga uuuccuuaut t                                             21

<210> SEQ ID NO 6
<211> LENGTH: 21
<212> TYPE: DNA
<213> ORGANISM: Artificial
<220> FEATURE:

```
<223> OTHER INFORMATION: siRNA

<400> SEQUENCE: 6
auaaggaaau cuuuaccgct t                                            21

<210> SEQ ID NO 7
<211> LENGTH: 21
<212> TYPE: DNA
<213> ORGANISM: Artificial
<220> FEATURE:
<223> OTHER INFORMATION: Negative seqeunce

<400> SEQUENCE: 7
uucuccgaac gugucacgut t                                            21

<210> SEQ ID NO 8
<211> LENGTH: 21
<212> TYPE: DNA
<213> ORGANISM: Artificial
<220> FEATURE:
<223> OTHER INFORMATION: Negative sequence

<400> SEQUENCE: 8
acgugacacg uucggaggat t                                            21

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cgtctaccgc ctgctcttct                                              20

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
ggtattccga ggcattctcc t                                            21
```

TARGET OF VGSC β3 PROTEIN FOR PREVENTION, TREATMENT AND DIAGNOSTIC DETECTION OF CANCERS

REFERENCE TO A SEQUENCE LISTING SUBMITTED ELECTRONICALLY VIA EFS-WEB

The content of the electronically submitted sequence listing, file name: PF140177USP-sequence listing.txt; size: 4,453 bytes; and date of creation: Apr. 7, 2017, filed herewith, is incorporated herein by reference in its entirety.

TECHNICAL FIELD

The present application relates to the association of VGSC β3 proteins with tumors, and in particular to inhibitors of VGSC β3 proteins and their use for the prevention and treatment of tumors, in particular cancers, to a method for preventing and treating tumors, in particular cancers using the inhibitors, to a method for screening antineoplastic agents using the VGSC β protein or its regulatory sequences, and to a method and use for diagnosis and detection of tumors using the VGSC β3 protein.

BACKGROUND OF THE INVENTION

Voltage-gated ion channels, or voltage-dependent and voltage-sensitive ion channels, are by far one of the most complex superfamilies involved in the signal transduction process known to mankind. There are more than 140 members (CATTERALL W A, CHANDY K G, CLAPHAM D E, et al International Union of Pharmacology: Approaches to the Nomenclature of Voltage-Gated Ion Channels [J]. Pharmacal Rev, 2003, 55 (4): 573-574), and new members are constantly being discovered. After purification, cloning and determination, it shows that the ion channel proteins are complexes composed of multiple subunits. Voltage-gated ion channels are composed of subunits α, β, γ, δ, but the composition of different ion channels is slightly different.

The voltage-gated sodium channel consists of an α subunit and a β subunit (see FIG. 1) (CATTERALL W A. From ionic currents to molecular mechanisms: the structure and run ion of voltage-gated sodium channels [J]. Neuron, 2000, 26 (11): 13-25, CATTERALL W A, GOLDIN A L, WAXMAN S G. International Union of Pharmacology. XXXIX. Compendium of Voltage-Gated Ion Channels: Sodium Channels [J]. Pharmacol Rev, 2003, 55 (4): 575-578). The α subunit has a molecular weight of about 260 kDa and consists of four homologous transmembrane domains (I-IV). Each domain contains six transmembrane helices (S1 to S6), S4 is a voltage receptor, and the short peptide between S5 and S6 participates in the formation of the pore, acts as a gate, and participates in mediating the depolarization process. In general, in addition to the α subunit, VGSC also contains 1 or 2 small molecule polypeptide stalled β subunit. For mammalian brain nerve cells, the sodium channels consist of a complex composed by one alpha subunit ($Na_v1.1$ to $Na_v1.9$) and one or more auxiliary beta subunits ($\beta_1$, $\beta_2$, $\beta_3$ and $\beta_4$ (33-36 kDa)).

According to the sensitivity of sodium channel to its blacker tetrodoxin (TTX), the subtypes of sodium channels are divided into two types: TTX-sensitive ($Na_v1.1$, $Na_v1.2$, $Na_v1.3$, $Na_v1.4$, $Na_v1.6$, $Na_v1.7$) and TTX insensitive ($Na_v1.5$, $Na_v1.8$, $Na_v1.9$) (ROGER S, POTIER M, VANDIER C, et al., Voltage-Gated Sodium Channels: New Targets in Cancer Therapy? [J]. Curr Pharm Des, 2006, 12 (28): 3681-3695). β subunit has many functions, which can not only regulate the expressions of voltage gating ion channels in the plasma membrane, but also interact with cytoskeleton protein, extracellular matrix and other cell adhesion molecules as a cell adhesion molecule (KAUFMANN S G, WESTENBROEK R E, ZECHNER C. Functional protein expression of multiple sodium channel alpha- and beta-subunits isoforms in neonatal cardiomyocytes [J]. J Mol Cell Cardiol, 2009, 48 (1): 261-269; BRACKENBURY W J, DAVIS T H, CHEN C, et al. Voltage-gated $Na^+$ channel beta-subunit-mediated neurite outgrowth requires Fyn kinase and contributes to postnatal CNS development in vivo [J]. J Neurosci, 2008, 28 (12): 3246-3256). In recent years, people gradually realized the importance of β subunits as auxiliary subunits on the channel function, such as β subunit can regulate the transporting and positioning of α subunit in the cell membrane, and regulate myocardial $Na^+$ channel late current. In addition, diseases caused by β subunit mutations are gradually incorporated into the study of gene-phenotype interactions.

$\beta_1$ and $\beta_3$ subunits have high homology, and they bind to α subunit by non-covalent bond. $\beta_2$ and $\beta_4$ subunits have high homology, and they bind to α subunit by disulfide bond. The functions of $\beta_1$ and $\beta_2$ subunit have been identified as cell adhesion molecules (CAM), the functions of $\beta_3$ and $\beta_4$ subunit are not clear. Although $\beta_3$ bind to α subunit through non-covalent bond as $\beta_1$ subunit, the role of the two is different, $\beta_3$ subunit regulates Nav1.8 expression on cell surface by antagonizing endoplasmic reticulum-releasing/recovering signal (ZHANG Z N, LI Q, LIU C, et al. The voltage-gated $Na^+$ channel $Na_v1.8$ contains an ER-retention/retrieval signal antagonized by the $\beta_3$ subunit $\beta_3$ Cell Sci, 2008, 121: 3243-3252). The $\beta_3$ subunit does not have the effect of cell adhesion, and the $\beta_3$ subunit neither does participate in the trans-homophilic cell-cell adhesion nor associate with anchoring protein ankyrinG (MCEWEN D P, CHEN C, MEADOWS L S, et al. The voltage-gated $Na^+$ channel β3 subunit does not mediate trans homophilic cell adhesion or associate with the cell adhesion molecule contactin. Neurosci Lett, 2009, 462: 272-275).

In summary, the research of voltage-gated sodium ion channel β subunit has been paid more and more attention, and functional subunits such as β subunit have become a new target for disease treatment and a new perspective to understand the pathogenesis of disease. However, the prior art does not relate to the association of the $\beta_3$ subunit with a tumor, nor does it relate to its use in the diagnosis and treatment of tumors.

SUMMARY OF THE INVENTION

The invention has the first discovery that the VGSC β3 has certain correlation with tumors and can act as a target for the diagnosis and treatment of tumors.

The first aspect of the present invention relates to inhibitors of VGSC β3, which can be used to prevent or treat a tumor in a subject.

The second aspect of the present invention relates to a pharmaceutical composition for the prevention or treatment of tumors in a subject comprising an inhibitor of VGSC β3, preferably further comprising a pharmaceutically acceptable carrier, optionally further comprising other tumor therapeutic agents in concert with the inhibitor of VGSC β3.

The third aspect of the present invention relates to a method of preventing or treating a tumor in a subject using an inhibitor of VGSC β3, comprising administering to a subject an amount of a VGSC β3 inhibitor effective to inhibit the expression and/or activity of VGSC β3.

The present invention also relates to the use of inhibitors of VGSC β3 in the prevention or treatment of tumors in a subject, and to the use of inhibitors of VGSC β3 for the preparation of pharmaceutical compositions for the prevention or treatment of tumors in a subject.

The fourth aspect of the present invention relates to a method of modulating one or more activities in a cell expressing VGSC β3, comprising contacting the cell with an amount of a VGSC β3 inhibitor effective to modulate said one or more activities.

The fifth aspect of the present invention relates to a method for diagnosing and detecting tumors using VGSC β3 proteins, to a method for diagnosing and detecting tumors using a means for detecting VGSC β3 proteins, such as a means for measuring VGSC β3 subunit encoding DNA level or mRNA level or protein expression level, to use of a means for detecting VGSC β3 protein in the diagnosis and detection of tumors, and use of a means for detecting VGSC β3 protein in the preparation of a kit for the diagnosis and detection of tumors.

The sixth aspect of the present invention relates to a method for inhibiting the proliferation of tumor cells by using an inhibitor of VGSC β3, to use of an inhibitor of VGSC β3 for inhibiting tumor cell proliferation, and to use of an inhibitor of VGSC β3 in preparing a pharmaceutical composition or a kit for inhibiting tumor cell proliferation.

The seventh aspect of the present invention relates to design, screening and preparation of an active substance for prophylaxis or treatment of tumors in a subject, using VGSC β3 protein or its expression regulation sequence as target, and a pharmaceutical composition comprising the said active substance.

The present invention also relates to a method of identifying a tumor suppressor, wherein the tumor is characterized by a differential expression of VGSC β3 compared to a control. The method comprises contacting a cell expressing VGSC β3 with a candidate compound to determine whether the VGSC β3-related activity is modulated. Regulation of VGSC β3-related activity is an indicator of cancer suppressors.

The present invention also relates to a kit for detecting or diagnosing a tumor comprising a means for measuring VGSC β3 subunit encoding DNA level or mRNA level or protein expression level.

In certain embodiment, the tumor is associated with VGSC β3, preferably a cancer, more preferably selected from lung cancer, liver cancer or leukemia.

In certain embodiment, the VGSC β3 inhibitor is selected from inhibitors capable of inhibiting DNA encoding the VGSC β3 protein, an inhibitor capable of inhibiting the expression of the gene by modulating the upstream and downstream regulatory sequences of the VGSC β3 protein coding gene, an RNAi active agent targeting the VGSC β3 protein, an antibody that binds to the VGSC β3 protein, a small molecule inhibitor of the VGSC β3 protein, an antisense oligonucleotide capable of inhibiting the expression or activity of the VGSC β3 protein, a (poly) peptide and other nucleic acids, or mimetics.

In one embodiment, the inhibitor is an RNAi inhibitor, preferably a dsRNA, more preferably an siRNA. Most preferably, the siRNA double-stranded region has a nucleotide length of 9-50 bp, 15-36 bp, 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 21-30 bp, 21-26 bp, 21-25 bp, 21-24 bp, 21-23 bp, 21-22 bp, 21 bp, 22 bp or 23 bp, and comprising an antisense strand and a sense strand substantially complementary to the antisense strand, wherein the antisense strand is at least about 80% to about 90% complementary to 15, 16, 17, 18, 19, 20 or 21 or more consecutive nucleotides of target gene, or hybridize with them under stringent conditions, or more preferably, is at least about 90-95% complementary to 15, 16, 17, 18, 19, 20 or 21 or more consecutive nucleotides of target gene, or hybridize with them under stringent conditions, or most preferably, is at least about 95%, 96%, 97%, 98% or 99% complementary to 15, 16, 17, 18, 19, 20 or 21 or more consecutive nucleotides of target gene, or hybridize with them under stringent conditions, or exactly the same to them, wherein the target gene is a target gene encoding a VGSC β3 protein, preferably the VGSC β3 is from a mammal, preferably from humans, also preferably the amino acid sequence of the VGSC β3 is set forth in SEQ ID NO: 1, most preferably the nucleotide sequence of the target gene encoding the VGSC β3 protein is set forth in SEQ ID NO: 2. Most preferably, the RNAi agent is an siRNA selected from the group consisting of:

```
SCN3B-homo-409
                                  (SEQ ID NO: 3)
5'-CCUGCCUUCAAUAGAUUCUTT-3'

(SEQ ID NO: 4)
5'-ACAAUCUAUUGAAGGCAGGTT-3';
or

SCN3B-homo-608
                                  (SEQ ID NO: 5)
5'-GCGGUAAAGAUUUCCUUAUTT-3

(SEQ ID NO: 6)
5'-AUAAGGAAAUCUUUACCGCTT-3'.
```

In another embodiment, the inhibitor is an antibody that binds to the VGSC β3 protein, preferably the antibody is a monoclonal antibody, more preferably a humanized monoclonal antibody. Preferably, the VGSC β3 protein bound to the antibody is from a mammal, preferably from a human, most preferably amino acid sequence thereof is set forth in SEQ ID NO: 1.

In another embodiment, the inhibitor is a peptide, such as analgesic antineoplastic valine (AGAP). In certain embodiment, the cells expressing VGSC β3 are tumor cells.

In certain embodiment, the tumor cells are preferably cancer cells, more preferably hepatoma cells or lung cancer cells, most preferably HepG2 cells or A549 cells.

In certain embodiment, the means for detecting the VGSC β3 protein is a means for measuring VGSC β3 subunit encoding DNA level or mRNA level or protein expression level, comprising a detectable antibody, small molecules, oligonucleotides, decoys, mimetics or probes capable of detecting the expression and activity of the VGSC β3 protein.

Other aspects and embodiments of the present invention are set forth in the following detailed description of the present invention, or as will become apparent from the description.

EMBODIMENTS OF THE PRESENT INVENTION

In particular, the present invention relates to the following specific embodiments:

1. A method for detecting or diagnosing a tumor associated with a VGSC β3 subunit in a patient using a VGSC β3 subunit, comprising:
   a) Separating a sample from a patient;
   b) Measuring VGSC β3 subunit encoding DNA level or mRNA level or protein expression level of the sample obtained in a) and normal control cells;
   c) Comparing the VGSC β3 subunit encoding DNA level or mRNA level or protein expression level measured in b);
   d) The higher protein or gene content of VGSCβ3 in the sample or cells to be tested than the normal control indicating that the subject has VGSC β3-related tumors.

2. Use of means for measuring VGSC β3 subunit encoding DNA level or mRNA level or protein expression level in the preparation of a kit for detecting or diagnosing a tumor associated with a VGSC β3 subunit in a patient, wherein the higher VGSC β3 subunit encoding DNA level or mRNA level or protein expression level measured in the sample from the patient than the normal control indicates that the patient has a tumor.

3. The method of embodiment 1 or the use of embodiment 2, wherein the sample is a sample of a tissue suspected of having a tumor, preferably a tumor biopsy or a cell extract thereof.

4. The method of embodiment 1 or 3 or the use of embodiment 2 or 3, wherein the tumor is cancer, preferably liver cancer, leukemia or lung cancer, most preferably the liver cancer is HepG2 liver cancer or the lung cancer is A549 lung cancer.

5. The method of any one of embodiments 1, 3 and 4, or use of any one of embodiments 2, 3 and 4, wherein the mRNA level is measured using a reverse transcription PCR method or the protein level is measured using Western blotting.

6. The method of any one of embodiments 1, 3, 4 and 5, or use of any one of embodiments 2, 3, 4 and 5, wherein the means for measuring the encoding DNA level or mRNA level or protein level comprises a probe or primer capable of measuring VGSC β3 subunit encoding DNA level or mRNA level, or a detectable antibody, small molecules, oligonucleotides, decoys, mimetics or probes capable of detecting the expression and activity of the VGSC β3 protein.

7. An inhibitor of VGSC β3 for use in prevention or treatment of a tumor in a subject.

8. A method for preventing or treating a tumor in a subject using an inhibitor of VGSC β3, comprising administering to a subject an amount of a VGSC β3 inhibitor effective to inhibit the expression and/or activity of VGSC β3.

9. Use of an inhibitor of VGSC β3 in the prevention or treatment of tumors in a subject, or use of an inhibitor of VGSC β3 in the preparation of a pharmaceutical composition for the prevention or treatment of tumors in a subject.

10. The inhibitor of embodiment 7 or the method of embodiment 8 or the use of embodiment 9, wherein the VGSC β3 inhibitor is selected from inhibitors capable of inhibiting DNA encoding the VGSC β3 protein, an inhibitor capable of inhibiting the expression of the gene by modulating the upstream and downstream regulatory sequences of the VGSC β3 protein coding gene, an RNAi active agent targeting the VGSC β3 protein, an antibody that binds to the VGSC β3 protein, a small molecule inhibitor of the VGSC β3 protein, an antisense oligonucleotide capable of inhibiting the expression or activity of the VGSC β3 protein, a (poly) peptide and other nucleic acids, or mimetics.

11. The inhibitor or method or use of embodiment 10, wherein the inhibitor is an RNAi inhibitor, preferably a dsRNA, more preferably an siRNA, most preferably, the siRNA double-stranded region has a nucleotide length of 9-50 bp, 15-36 bp, 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 21-30 bp, 21-26 bp, 21-25 bp, 21-24 bp, 21-23 bp, 21-22 bp, 21 bp, 22 bp or 23 bp, and comprising an antisense strand and a sense strand substantially complementary to the antisense strand, wherein the antisense strand is at least about 80% to about 90% complementary to 15, 16, 17, 18, 19, 20 or 21 or more consecutive nucleotides of target gene, or hybridize with them under stringent conditions, or more preferably, is at least about 90-95% complementary to 15, 16, 17, 18, 19, 20 or 21 or more consecutive nucleotides of target gene, or hybridize with them under stringent conditions, or most preferably, is at least about 95%, 96%, 97%, 98% or 99% complementary to 15, 16, 17, 18, 19, 20 or 21 or more consecutive nucleotides of target gene, or hybridize with them under stringent conditions, or exactly the same to them, wherein the target gene is a target gene encoding a VGSC β3 protein, preferably the VGSC β3 is from a mammal, preferably from humans, also preferably the amino acid sequence of the VGSC β3 is set forth in SEQ ID NO: 1, most preferably the nucleotide sequence of the target gene encoding the VGSC β3 protein is set forth in SEQ ID NO: 2.

12. The inhibitor or method or use of embodiment 11, wherein the RNAi agent is an siRNA selected from the group consisting of:

```
SCN3B-homo-409
                                         (SEQ ID NO: 3)
5'-CCUGCCUUCAAUAGAUUCUTT-3'

(SEQ ID NO: 4)
5'-ACAAUCUAUUGAAGGCAGGTT-3';
or

SCN3B-homo-608
                                         (SEQ ID NO: 5)
5'-GCGGUAAAGAUUUCCUUAUTT-3

(SEQ ID NO: 6)
5'-AUAAGGAAAUCUUUACCGCTT-3'.
```

13. The inhibitor or method or use of embodiment 10, wherein the inhibitor is an antibody or fragment thereof that binds to the VGSC β3 protein, preferably the antibody is a monoclonal antibody or fragment thereof, more preferably a humanized monoclonal antibody or fragment thereof, preferably the VGSC β3 protein bound to the antibody is from a mammal, preferably from a human, most preferably amino acid sequence thereof is set forth in SEQ ID NO: 1.

14. The inhibitor or method or use of embodiment 10, wherein the inhibitor is a polypeptide, preferably analgesic antineoplastic valine (AGAP).

15. The inhibitor or method or use of any one of embodiments 7-14, wherein the tumor is a tumor associated with the VGSC β3 subunit, preferably a cancer, more preferably a liver cancer, a leukemia or a lung cancer, most preferably the liver cancer is HepG2 liver cancer or the lung cancer is an A549 type lung cancer.

16. A method for modulating one or more activities in a cell expressing VGSC β3, comprising contacting the cell with an amount of a VGSC β3 inhibitor effective to modulate the one or more activities.

17. The method of embodiment 16, wherein the cell is a tumor cell.

18. A method for inhibiting the proliferation of tumor cells by using an inhibitor of VGSCβ3.

19. Use of an inhibitor of VGSC β3 in inhibiting tumor cell proliferation.

20. Use of an inhibitor of VGSC β3 in the preparation of a pharmaceutical composition or a kit for suppressing tumor cell proliferation.

21. The method of embodiment 17 or 18 or the use of embodiment 19 or 20, wherein the VGSC β3 inhibitor is selected from inhibitors capable of inhibiting DNA encoding the VGSC β3 protein, an inhibitor capable of inhibiting the expression of the gene by modulating the upstream and downstream regulatory sequences of the VGSC β3 protein coding gene, an RNAi active agent targeting the VGSC β3 protein, an antibody that binds to the VGSC β3 protein, a small molecule inhibitor of the VGSC β3 protein, an antisense oligonucleotide capable of inhibiting the expression or activity of the VGSC β3 protein, a (poly) peptide and other nucleic acids, or mimetics.

22. The method or use of embodiment 21, wherein the inhibitor is an RNAi inhibitor, preferably a dsRNA, more preferably an siRNA, most preferably, the siRNA double-stranded region has a nucleotide length of 9-50 bp, 15-36 bp, 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 21-30 bp, 21-26 bp, 21-25 bp, 21-24 bp, 21-23 bp, 21-22 bp, 21 bp, 22 bp or 23 bp, and comprising an antisense strand and a sense strand substantially complementary to the antisense strand, wherein the antisense strand is at least about 80% to about 90% complementary to 15, 16, 17, 18, 19, 20 or 21 or more consecutive nucleotides of target gene, or hybridize with them under stringent conditions, or more preferably, is at least about 90-95% complementary to 15, 16, 17, 18, 19, 20 or 21 or more consecutive nucleotides of target gene, or hybridize with them under stringent conditions, or most preferably, is at least about 95%, 96%, 97%, 98% or 99% complementary to 15, 16, 17, 18, 19, 20 or 21 or more consecutive nucleotides of target gene, or hybridize with them under stringent conditions, or exactly the same to them, wherein the target gene is a target gene encoding a VGSC β3 protein, preferably the VGSC β3 is from a mammal, preferably from humans, also preferably the amino acid sequence of the VGSC β3 is set forth in SEQ ID NO: 1, most preferably the nucleotide sequence of the target gene encoding the VGSC β3 protein is set forth in SEQ ID NO: 2.

23. The method or use of embodiment 22, wherein the RNAi agent is an siRNA selected from the group consisting of:

SCN3B-homo-409

(SEQ ID NO: 3)
5'-CCUGCCUUCAAUAGAUUCUTT-3'

(SEQ ID NO: 4)
5'-ACAAUCUAUUGAAGGCAGGTT-3';

or

SCN3B-homo-608

(SEQ ID NO: 5)
5'-GCGGUAAAGAUUUCCUUAUTT-3

(SEQ ID NO: 6)
5'-AUAAGGAAAUCUUUACCGCTT-3'.

24. The method or use of embodiment 21, wherein the inhibitor is an antibody or fragment thereof that binds to the VGSC β3 protein, preferably the antibody is a monoclonal antibody or fragment thereof, more preferably a humanized monoclonal antibody or fragment thereof, preferably the VGSC β3 protein bound to the antibody is from a mammal, preferably from a human, most preferably amino acid sequence thereof is set forth in SEQ ID NO: 1.

25. The method or use of embodiment 21, wherein the inhibitor is a polypeptide, preferably analgesic antineoplastic valine (AGAP).

26. The method or use of any one of embodiments 17-25, wherein the tumor is a tumor associated with the VGSC β3 subunit, preferably a cancer, more preferably a liver cancer, a leukemia or a lung cancer, most preferably the liver cancer is HepG2 liver cancer or the lung cancer is an A549 type lung cancer.

27. The method or use of any one of embodiments 18-26, wherein the tumor cell is a hepatoma cell or a lung cancer cell, preferably a HepG2 cell or an A549 cell.

28. A method for designing and preparing an active substance for prophylaxis or treatment of tumors in a subject, using VGSC protein or its gene regulation sequence as target, the method comprises designing an active substance capable of inhibiting the expression or activity of the VGSCβ3 protein based on the amino acid sequence and the nucleic acid coding sequence of the VGSCβ3 protein.

29. The method of embodiment 28, further comprises steps of preparing the active substance as designed above and determining whether it inhibits expression, activity and/or associated biological activity of VGSCβ3 or inhibits the growth of one or more of cancer cells.

30. A method for screening an active substance for preventing or treating tumors in a subject, comprising steps of contacting a cell expressing VGSC β3 with a candidate active substance to determine whether expression, activity and/or associated biological activity of VGSC β3 is inhibited, or whether or not one or more cancer cell indicators, such as growth of cancer cells, are inhibited, wherein if the expression, activity and/or associated biological activity of VGSCβ3 is inhibited or one or more cancer cell indicators are inhibited, then it is indicated that the candidate active substance is an active substance for preventing or treating a tumor.

31. A method for screening an anticancer agent or an inhibitor for inhibiting tumor cell proliferation, comprising contacting a cell expressing VGSC β3 with a candidate compound to determine whether expression, activity and/or associated biological activity of VGSC β3 is modulated, or whether or not one or more cancer cell indicators, such as growth of cancer cells, are inhibited, wherein if the expression, activity and/or associated biological activity of VGSCβ3 is inhibited or one or more cancer cell indicators are inhibited, then it is indicated the active substance is an anticancer agent or an inhibitor for inhibiting tumor cell proliferation.

32. The method of any one of embodiments 28-31, wherein the active substance is selected from inhibitors capable of inhibiting DNA encoding the VGSC β3 protein, an inhibitor capable of inhibiting the expression of the gene by modulating the upstream and downstream regulatory sequences of the VGSC β3 protein coding gene, an RNAi active agent targeting the VGSC β3 protein, an antibody that binds to the VGSC β3 protein, a small molecule inhibitor of the VGSC β3 protein, an antisense oligonucleotide capable of inhibiting the expression or activity of the VGSC β3 protein, a (poly) peptide and other nucleic acids, or mimetics.

33. The use of embodiment 32, wherein the active substance is an RNAi inhibitor, preferably a dsRNA, more preferably an siRNA, most preferably, the siRNA double-stranded region has a nucleotide length of 9-50 bp, 15-36 bp, 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 21-30 bp, 21-26 bp, 21-25 bp, 21-24 bp, 21-23 bp, 21-22 bp, 21 bp, 22 bp or 23 bp, and comprising an antisense strand and a sense strand substantially complementary to the antisense strand, wherein the antisense strand is at least about 80% to about 90% complementary to 15, 16, 17, 18, 19, 20 or 21 or more consecutive nucleotides of target gene, or hybridize with them under stringent conditions, or more preferably, is at least about 90-95% complementary to 15, 16, 17, 18, 19, 20 or 21 or more consecutive nucleotides of target gene, or hybridize with them under stringent conditions, or most preferably, is at least about 95%, 96%, 97%, 98% or 99% complementary to 15, 16, 17, 18, 19, 20 or 21 or more consecutive nucleotides of target gene, or hybridize with them under stringent conditions, or exactly the same to them, wherein the target gene is a target gene encoding a VGSC β3 protein, preferably the VGSC β3 is from a mammal, preferably from humans, also preferably the amino acid sequence of the VGSC β3 is set forth in SEQ ID NO: 1, most preferably the nucleotide sequence of the target gene encoding the VGSC β3 protein is set forth in SEQ ID NO: 2

34. The method or use of embodiment 33, wherein the active substance is an siRNA selected from the group consisting of:

```
SCN3B-homo-409
                                      (SEQ ID NO: 3)
5'-CCUGCCUUCAAUAGAUUCUTT-3'

(SEQ ID NO: 4)
5'-ACAAUCUAUUGAAGGCAGGTT-3';
or

SCN3B-homo-608
                                      (SEQ ID NO: 5)
5'-GCGGUAAAGAUUUCCUUAUTT-3

(SEQ ID NO: 6)
5'-AUAAGGAAAUCUUUACCGCTT-3'.
```

35. The use of embodiment 32, wherein the active substance is an antibody that binds to the VGSC β3 protein, preferably the antibody is a monoclonal antibody, more preferably a humanized monoclonal antibody, preferably the VGSC β3 protein bound to the antibody is from a mammal, preferably from a human, most preferably amino acid sequence thereof is set forth in SEQ ID NO: 1.

36. The use of embodiment 32, wherein the active substance is a polypeptide, preferably analgesic antineoplastic valine (AGAP)$_o$ 37. The method or use of any one of embodiments 28-36, wherein the tumor is a tumor associated with the VGSC β3 subunit, preferably a cancer, more preferably a liver cancer, a leukemia or a lung cancer, most preferably the liver cancer is HepG2 liver cancer or the lung cancer is an A549 type lung cancer.

38. The method or use of any one of embodiments 29-37, wherein the cancer cell is a cancer cell associated with the VGSC β3 subunit, preferably a liver cancer cell or a lung cancer cell, more preferably a HepG2 cell or an A549 cell.

39. Use of VGSC β3 as a target, in the preparation of a pharmaceutical composition for the prevention or treatment of tumors, and in the preparation of a reagent for the diagnosis or detection of tumors.

40. A kit for detecting or diagnosing a tumor associated with a VGSC β3 subunit in a patient, comprising a means for measuring VGSC β3 subunit encoding DNA level or mRNA level or protein expression level.

41. The kit of embodiment 40, wherein the kit further comprises one or more of the following: a control (positive and/or negative), control container, a photograph or description of a representative example of positive and/or negative results.

42. The kit of embodiment 40 or 41, wherein the tumor is cancer, preferably liver cancer, leukemia or lung cancer, most preferably the liver cancer is HepG2 liver cancer or the lung cancer is A549 type lung cancer.

43. The kit of any one of embodiments 40-42, wherein the means for measuring the encoding DNA level or mRNA level or protein level comprises a probe or primer capable of measuring VGSC β3 subunit encoding DNA level or mRNA level, or a detectable antibody, small molecules, oligonucleotides, decoys, mimetics or probes capable of detecting the expression and activity of the VGSC β3 protein.

A-D was the result of Annexin V-FITC-PI staining. A: Result when HepG2 cells were not interfered; B: Result when HepG2 cells were interfered for 48 h; C: Result when HepG2 cells were interfered for 60 h; Result when HepG2 cells were interfered for 72 h.

E-H was Hoechst 33342-PI staining results. E: Result when HepG2 cells were not interfered; F: Result when HepG2 cells were interfered for 48 h; G: Result when HepG2 cells were interfered for 60 h; H: Result when HepG2 cells were interfered for 72 h.

I: Q2 and Q4 statistical results, of which Q2 represents late apoptosis, Q4 represents early apoptosis.

Figure 14:
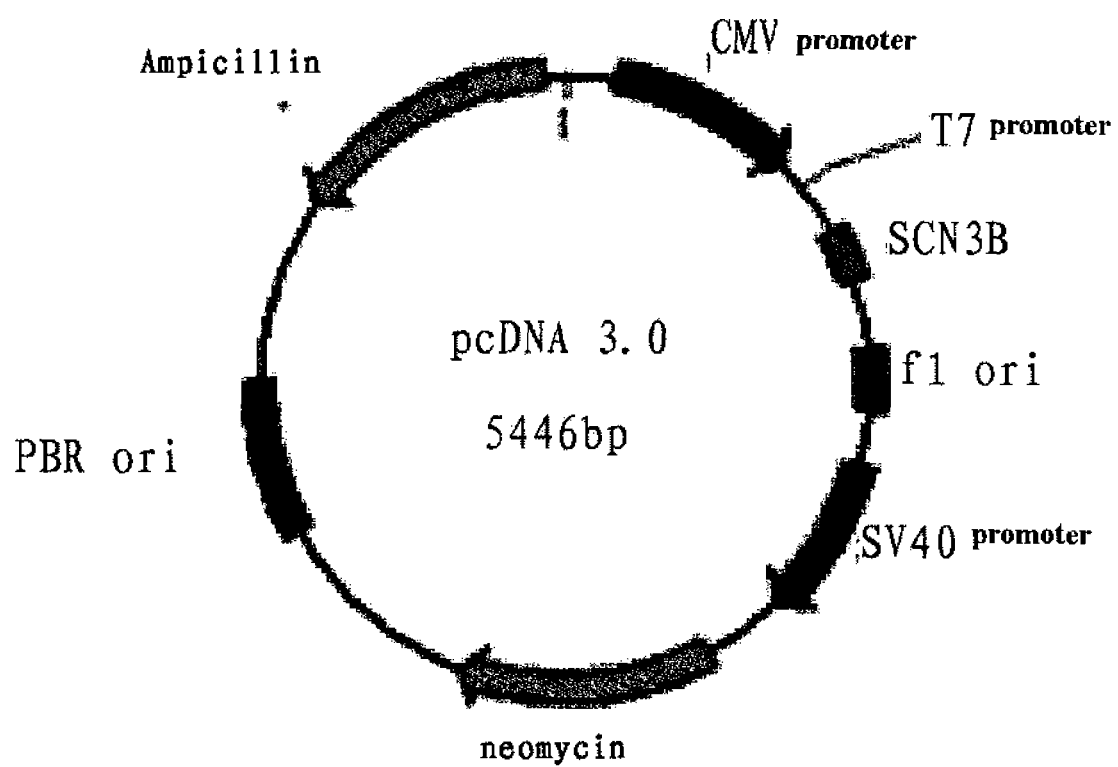
Figure 15:
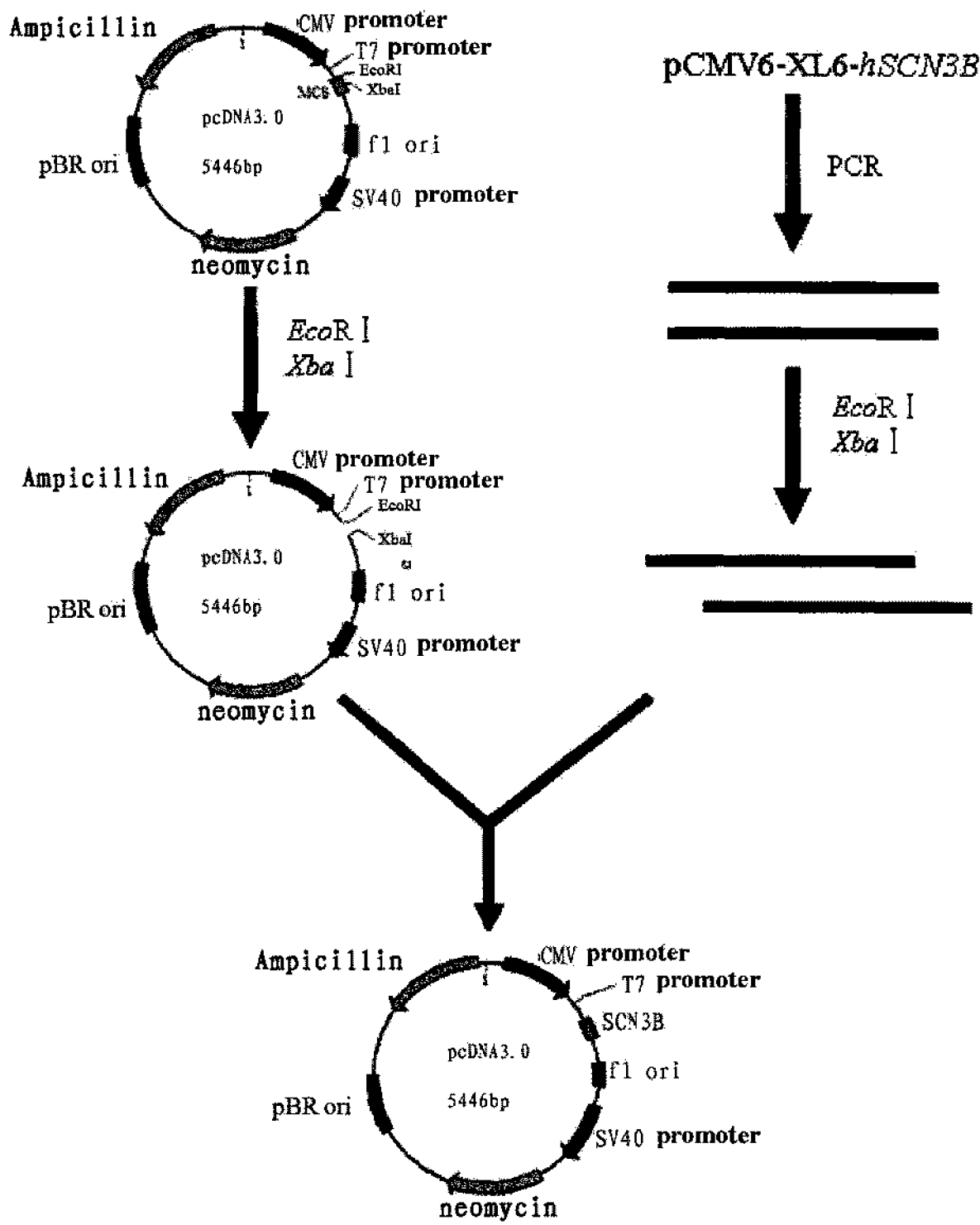

FIG. 14: Plasmid map containing the nucleic acid sequence encoding the VGSC β3 subunit (i.e., SCN3B, set forth in SEQ ID NO: 2);

FIG. 15: A flow chart showing the construction of the plasmid described in FIG. 14.

DETAILED DESCRIPTION OF THE INVENTION

The present invention may be more readily understood by reference to the following detailed description of the preferred embodiments of the invention and the examples contained herein. Unless otherwise indicated, the terminology used herein will be understood in accordance with the customary usage of those of ordinary skill in the relevant art. In addition to the definitions of terms provided below, definitions of commonly used terms in molecular biology can also be found in Rieger et al., 1991 Glossary of genetics: classical and molecular, fifth edition, Berlin: Springer-Verlag; and in Current protocols in Molecular Biology, F M Ausubel et al., Current Protocols, a joint venture of Greene Publishing Associates, Inc. and John Wiley & Sons, Inc. (1998 supplement). It is to be understood that the terminology used herein is for the purpose of describing particular embodiments only and is not meant to be limiting.

Reference is made to various publications throughout the application. The disclosures of all of these publications and those references cited in these publications are incorporated herein by reference in their entirety for the purpose of more fully describing the state of the art to which the invention pertains. Standard techniques for cloning, DNA isolation, amplification and purification, standard techniques for enzymatic reactions involving DNA ligase, DNA polymerase, restriction endonuclease, and the like, and a variety of separation techniques are well known in the art and commonly used. Some standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (ed.) 1993 Meth. Enzymol. 218, Part I; Wu (ed.) 1979 Meth Enzymol. 68; Wu et al., (Ed.) 1983 Meth. Enzymol. 100 and 101; Grossman and Moldave (ed.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical. Methods in Molecular Biology; Glover (ed.) 1985 DNA Cloning Vol I and II, IRL Press, Oxford, UK; Hames Higgins (ed.) 1985 Nucleic Acid Hybridization, IRL Press, Oxford, UK; And Setlow and Hollaender 1979 Genetic Engineering: Principles and Methods, Vol. 1-4, Plenum Press, New York; Remington's Pharmaceutical Sciences, 18th Edition (Easton, Pa.: Mack Publishing Company, 1990); Methods In Enzymology (edited by Colowick and N. Kaplan, Academic Press, Inc.) and Handbook of Experimental Immunology, Volumes I-IV (D. M. Weir and C. C. Blackwell, eds., 1986, Blackwell Scientific Publications). When used, abbreviations and nomenclature are considered standard in the art and are often used in specialized journals such as those referred to herein as specialized journals.

I. VGSC β3 Protein

As used herein, the term "VGSC β3" refers to the β3 subunit of any voltage-sensitive ion channel known in the art, preferably the mammalian VGSC β3, more preferably the VGSC β3 protein is from a human. Exemplary VGSC β3 that has been characterized in the art includes Gene ID 55800, NM 018400 (http://www.ncbi.nlm.nih.gov/gene/55800). Exemplary VGSC β3 muteins are also described in Dan Hu MD, Hector Barajas-Martines, Elena Burashnikov B S, et al. A mutation in the β3 subunit of the cardiac sodium channel associated with brugada ECG phenotype. Circ Cardiovasc Genet. 2009 2 (3): 270-278.

For example, a human VGSC β3 protein comprises the amino acid sequence as follows, or its amino acid sequence is as follows:

```
SEQ ID NO: 1: Amino acid sequence of human VGSC β3 protein:
M P F N R L F P A S L V L I Y W V S V C F P V C

V E V P S E T E A V Q G N P M K L R C I S C M K R

E E V E A T T V V E W F Y R P E G G K D F L I Y E

Y R N G H Q E V E S P F Q G R L Q W N G S K D L Q
```

-continued

```
D V S I T V L N V T L N D S G L Y T C N V S R E F

E F E A H R P F V K T T R L I P L R V T E E A G E D

F T S V V S E I M M Y I L L V F L T L W L L I E M I

Y C Y R K V S K A E E A A Q E N A S D Y L A I P  S

E N K E N S A V P V E E *
```

SEQ ID NO:2: Nucleic acid sequence encoding human VGSC β3 protein:
atgc ctgccttcaa tagattgttt ccctggcttctctcgtgct tatctactgg gtcagtgtct gcttccctgt gtgtgtgaa gtgccctcggagacggaggc cgtgcagggc aaccccatga agctgcgctg catctcctgc atgaagagagaggaggtgga ggccaccacg gtggtggaat ggttctacag gcccgagggc ggtaaagatt tcatattta cgagtatcgg aatggccacc aggaggtgga gagcccttt caggggcgcctgcagtggaa tggcagcaag gacctgcagg acgtgtccat cactgtgctc aacgtcactetgaacgactc tggcctctac acctgcaatg tgtcccggga gtttgagttt gaggcgcatcggcctttgt gaagacgacg cggctgatcc cctaagagt caccgaggag gctggagaggacttcacctc tgtggtctca gaaatcatga tgtacatcct tctggtcttc ctcaccttgtggctgctcat cgagatgata tattgctaca gaaaggtctc aaaagccgaa gaggcagcccaagaaaacgc gtctgactac cttgccatcc catctgagaa caaggagaac tctgcggtac cagtggagga atag

II. VGSC β3 Inhibitors

As used herein, the term "VGSC β3 inhibitor" includes any substance capable of inhibiting DNA, mRNA or protein of VGSC β3, such as interfering RNA (RNAi agent), antibody, small molecule inhibitor, (poly) peptide and nucleic acid, antisense oligonucleotides, or mimetics. In particular, the VGSC β3 protein is capable of inhibiting the expression, activity and/or associated biological activity of the VGSC β3 protein by inhibiting its encoding DNA sequences, upstream and downstream regulatory sequences, mRNA and VGSC β3 proteins.

The terms"inhibition", "inhibit", "inhibiting" or "inhibited" VGSC β3 refer to any statistically significant reduction in the biological activity, biological level, activity and/or expression of VGSC β3, including complete blockade of activity and/or expression. For example, "inhibition", "inhibit", "inhibiting" or "inhibited" may refer to a reduction in VGSC β3 level, activity and/or expression of at least about 10, 20, 30, 40, 50, 60, 70, 80, 90 or 100%. Meanwhile, as used herein, the terms"inhibition", "inhibit", "inhibiting" or "inhibited" similarly refers to a significant reduction in level, activity and/or expression for any other biologically active agent or composition.

In some embodiments, the inhibitor of VGSC β3 inhibits VGSC β3 biological activity by 25%, 50%, 75%, 80%, 90%, 95%, 97%, 98%, 99% or 100%, compared with controls. In some embodiments, an inhibitor of VGSC β3 inhibits expression of VGSC β3 by at least 25%, 50%, 75%, 80%, 90%, 95%, 97%, 98%, 99% or 100%, compared with controls.

In a certain embodiment, the inhibitor of VGSC β3 disclosed herein comprises any agent known to inhibit VGSC β3 disclosed herein or in the art and administered to a patient in need thereof, such as a patient suffering from a tumor, in particular a cancer.

In the context of the symptoms of VGSC β3-related diseases, "decrease", "decreasing" or "decreased" refer to a statistically significant reduction in such level. Such reduction may for example be at least 10%, at least 20%, at least 30%, at least 40% or more. For a particular disease or a subject suffering from a particular disease, if the level or expression of VGSC β3 is elevated, the treatment with a VGSC β3 RNAi active agent as disclosed herein may specifically reduce the level or expression of VGSC β3 to a level within the normal range that is considered to be in the literature for individuals without such conditions. The level or expression of VGSC β3 can be measured by the evaluation of mRNA (e.g. by Northern blot or PCR) or by protein (e.g. Western blotting). The effect of RNAi agents on the expression of VGSCβ3 can be determined by measuring the transcription rate of the VGSCβ3 gene (e.g. by Northern blotting; or reverse transcriptase polymerase chain reaction or real-time polymerase chain reaction). Direct measurements can be performed on the level of VGSC β3 (expressed on the cell surface), for example by performing Western blotting on the tissue in which VGSC β3 is expressed.

As used herein, "down-regulation", "down-regulate", "down-regulated" or "down-regulating" refer to any statistically significant decrease in the biological activity and/or expression of VGSC β3, including complete blocking activity (i.e., complete inhibition) and/or expression. For example, "down-regulation", "down-regulate", "down-regulated" or "down-regulating" may refer to a reduction in VGSC β3 level, activity and/or expression of at least about 10, 20, 30, 40, 50, 60, 70, 80, 90 or 100%.

As used herein, the terms "inhibition", "inhibit", "inhibiting" or "inhibited" VGSC β3 refer to any statistically significant reduction in the biological level, activity and/or expression of VGSC β3, including complete blockade of activity and/or expression. For example, "inhibition", "inhibit", "inhibiting" or "inhibited" may refer to a reduction in VGSC β3 level, activity and/or expression of at least about 10, 20, 30, 40, 50, 60, 70, 80, 90 or 100%. Meanwhile, as used herein, the terms"inhibition", "inhibit", "inhibiting" or "inhibited" similarly refers to a significant reduction in level, activity and/or expression for any other biologically active agent or composition.

"Level" means that the VGSC β3 RNAi active agent or other inhibitor can alter the level of VGSC β3, for example, the level of VGSC β3 DNA or the level of mRNA or the level of VGSC β3 protein, or the level of activity of VGSC β3.

In one embodiment, an inhibitor of VGSC β3 is administrated, for example, an RNAi agent, reduces the level, expression and/or activity of VGSC β3 in the event that a disease is characterized by overexpression and/or activity of VGSC β3.

For level, expression and/or activity, "normal" or "almost normal" refers to at least about 50%, about 60%, about 70%, about 80%, about 90%, and/or about 100%; and/or no more than about 100%, about 120%, about 130%, about 140%, or about 150% of the level, expression or activity of VGSC β3 in healthy cells, tissues or organs.

In addition, in various embodiments, the level of VGSC β3 expression, activity, and/or level may be inhibited by the use of a VGSC β3 inhibitor of the present disclosure depending on the disease conditions and the biological environments.

II-1 Interfering RNA

In some embodiments, the VGSC β3 inhibitor is an interfering RNA (RNAi) active agent.

RNA interference techniques are well known in the art, and the design and acquisition of RNAi active agents are also known in the art, see, e.g., WO2011/073326 or WO2011/131707 for details.

RNA interference, known as "RNAi", is a method of reducing the expression of a gene of interest with a small single-stranded or double-stranded RNA molecule. Interfering RNAs include double-stranded or single-stranded small interfering RNA (ds siRNA or ss siRNA), microRNA (miRNA), small hairpin RNA (shRNA), and the like. Without wishing to be bound by theory, RNA interference seems to occur in vivo, and double-stranded RNA precursors are cleaved into small RNAs that are approximately 20-25 nucleotides in length. The cleavage was performed by RNAeIII-RNA helicase dicer. The sense strand of the siRNA, i.e. the strand having exactly the same sequence as the target mRNA sequence, is removed, leaving the "antisense strand" complementary to the target mRNA sequence to reduce mRNA expression. The antisense strand of the siRNA seems to lead the protein complex called RISC (RNA-induced silencing complex) to the mRNA, and then the Argonaute protein of RISC cleaves the mRNA, thereby reducing the protein production of the mRNA. Interfering RNA has catalytic activity, sub-chemical dose of mRNA-related interference RNA can reduce mRNA expression. Decreased mRNA expression may also occur through transcriptional and translational mechanisms.

RNAi active agents of the present disclosure target (e.g., bind, anneal, etc.) VGSC β3 mRNA. The use of a VGSC β3-specific RNAi agent results in a decrease in VGSC β3 activity, level and/or expression, such as a knock-down or knock-out target gene or target sequence.

In one embodiment, the RNAi comprises a single strand (e.g., a shRNA as described herein).

In various embodiments, one or both strands are nicked.

In one embodiment, a single stranded RNAi active agent oligonucleotide or polynucleotide may comprise a sense and/or antisense strand. See, e.g., Sioud 2005 J. Mol. Biol. 348: 1079-1090, and the references cited therein. Thus, the present disclosure contemplates RNAi active agents having single chains comprising the sense or antisense strand of an RNAi agent as described herein.

SiRNAs specifically for use in the present disclosure include those that can specifically bind to the VGSC β3 mRNA region and that have one or more of the following properties: binding in the coding region of VGSC β3; binding at or near the junction of 5' untranslated region and the coding section starting site; binding at or near the translation initiation site of the mRNA; binding at or near the junction of exons and introns; mRNAs or transcripts with little or no binding to other genes (with little or no "off-target effect"); binding to VGSC β3 mRNA in or near one or more regions that are not double stranded or stem, e.g., in the loop or single strand portion; little or no immunogenicity; in the segment of the VGSC β3 mRNA sequence conserved among a variety of animal species (including human, mouse, rat, cynomolgus monkey, etc.), the presence of conserved sequences facilitates the use of a variety of experimental animals; binding to double strand region of the mRNA; binding to an AT-rich region (e.g., at least about 50, 51, 52, 53, 54, 55, 56, 57, 58, 59 or 60% AT rich); and/or lack of specific sequences known or suspected to reduce siRNA activity, e.g., the presence of a GG sequence at the 5' end, which may reduce the separation of siRNA double stranded portions. In one embodiment, a VGSC β3-specific RNAi agent may be a double-stranded RNA having any one or more of these properties.

As used herein, the term "double-stranded RNA" or "dsRNA" refers to an RNAi active agent comprising a first strand and a second strand; for example, a composition comprising an RNA molecule or molecular complex having a hybrid duplex region i.e. the region of the nucleotide base pairing of the first strand and the second strand) comprising two antiparallel and substantially complementary nucleic acid strands known as "sense" and "antisense" directions relative to the target RNA. In the context of mRNA targets, the antisense strand is also referred to as the "guide" chain, and the sense strand is also referred to as the "passerby" chain. The passerby strand may include at least one or more of the following properties: one or more additional nucleotides (e.g., protrusions or 1 nt rings) compared to other chains, gaps, vacancies, etc., compared to other chains. In various embodiments, the RNAi active agent comprises a first strand and a second strand. In various embodiments, the first strand is a sense strand and the second strand is an antisense strand. In other embodiments, the first strand is an antisense strand and the second strand is a sense strand.

The duplex region may be any length that allows specific degradation of the desired target RNA by the RISC pathway, but typically ranges from 9 to 36 base pair ("bp"), for example, 15-30 bp in length. Considering the duplex between 9 and 36 bp, the duplex can be any length within that range, e.g. 9, 10, 11, 12, 13, 14, 15, 16, 17, 18, 19, 20, 21, 22, 23, 24, 25, 26, 27, 28, 29, 30, 31, 32, 33, 34, 35, or 36 bp, and any subranges therebetween, including but not limited to 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 20-25 bp, 20-23 bp, 20-23 bp, 20-21 bp, 21-30 bp, 21-26 bp, 20-25 bp, 21-25 bp, 21-24 bp, 21-23 bp, 21-22 bp, 21 bp, 22 bp, or 23 bp. The length of the dsRNA produced within the cell is typically in the range of about 19 to about 22 bp by Dicer and similar enzyme processing. One strand of the duplex domain of the dsRNA contains a sequence that is substantially complementary to the region of the target RNA. The two strands forming the duplex structure may be derived from a single RNA molecule having at least one self-complementary duplex domain or may be formed from two or more isolated RNA molecules that hybridize to form duplexes. When a duplex domain is formed from two self-complementary regions of a single molecule, the molecule may have a duplex domain that is separated by a single stranded nucleotide (referred to herein as "hairpin loops", for example, found in the shRNA structure), and the single-strand nucleotide is located between the 3' end of one strand that forms the duplex structure and the 5' end of the corresponding other strand. The hairpin loop may comprise at least one unpaired nucleotide; in some embodiments, the hairpin loop may comprise at least 3, at least 4, at least 5, at least 6, at least 7, at least 8, at least 9, at least 10, at least 20, at least 23, or more unpaired nucleotides. When two substantially complementary dsRNA strands are included in an isolated RNA molecule, these molecules do not have to be but can be covalently linked. When two strands are covalently linked by a hairpin loop, the structure is generally referred as "shRNA" herein and in the art. When the two strands are covalently linked by means other than the hairpin loop, the connection structure is referred to as a "linker".

The dsRNA molecules described herein (RNAi active agents) can be used for RNA interference of VGSC (A) Characters of RNAi Active Agent:Sense Strand, Antisense Strand and (Optionally) Overhang In various embodiments, the RNAi active agent comprises a first strand and a second strand, for example, a sense strand and an antisense strand, and optionally, one or both ends of the duplex containing unpaired nucleotides referred to herein as a overhang.

The term "antisense strand" refers to a chain of RNAi active agents that comprises a region that is substantially complementary to a target sequence. As used herein, the term "complementary region" refers to a region of the antisense strand that is substantially complementary to a sequence (e.g., a target sequence) as defined herein. When the complementary region is not fully complementary to the target sequence, the mismatch may be located in the internal or terminal region of the molecule. In general, the most tolerated mismatches are located in the internal region, for example, within 5, 4, 3 or 2 nucleotides at the 5'; and/or 3'.

As used herein, the term "sense strand" refers to a chain of RNAi active agents comprising a region that is substantially complementary to the region of the antisense strand of the term as defined herein.

Gene sequences may be different between individuals, especially in the wobbling position within the coding region, or in the untranslated region; the coding sequences of the individual may also be different from each other, resulting in additional differences in mRNA. Thus, the sense and antisense strand sequences of the RNAi active agent may be designed to correspond to the sequence of the individual patient when desired. The sequence of the RNAi active agent can also be modified to reduce immunogenicity, bind to undesirable mRNAs (e.g., "off-target effects") or to increase stability in the blood. These sequence variants do not depend on the chemical modification of the bases or 5'; or 3'; or other end caps of the RNAi active agent.

The RNAi active agent may also have 0, 1 or 2 overhangs, and in the case of 0 overhang, the active agent is blunt-ended. The RNAi active agent may have 0, 1 or 2 blunt ends. In the "blunt-ended RNAi active agent", both strands end with a base pair; therefore, the blunt-ended molecule lacks a 3'; or 5' single stranded nucleotide overhang.

As used herein, the term "overhang" or "nucleotide overhang" refers to at least one unpaired nucleotide that protrudes from the end of at least one of the two strands of the duplex structure of the RNAi active agent. For example, unpaired nucleotides form overhangs when the 3' end of a strand of the dsRNA extends beyond the 5' end of the other strand or vice versa. The dsRNA may comprise a overhang of at least one nucleotide; alternatively, the overhang may comprise at least two nucleotides, at least 3 nucleotides, at least 4 nucleotides, at least 5 nucleotides or more. The overhangs may comprise nucleotides/nucleoside analogs or consist of nucleotide/nucleoside analogs, including deoxynucleotides/nucleosides. The overhangs may be located on a sense strand, an antisense strand, or any combination thereof. In addition, nucleotides at the overhangs may be located 5', 3' or both ends of the antisense or sense strand of the dsRNA.

The RNAi active agent may also optionally comprise a cap. The term "cap" or the like includes a chemical moiety that is attached to a double stranded nucleotide duplex, but is used herein to exclude a chemical moiety that is a nucleotide or nucleoside. A "3" cap is attached to the 3' end of a nucleotide or oligonucleotide. A "5" cap is attached to the 5' end of the nucleotide or oligonucleotide. In one embodiment, the 3' end cap is as disclosed in, for example, WO 2005/021749 and WO 2007/128477.

Accordingly, the present disclosure contemplates VGSC β3-specific RNAi agents comprising antisense strands in the RNAi active agent, which may be continuous or linked through a linker or loop. In a more specific embodiment, the RNAi active agent comprises an antisense strand and a sense strand, and together comprise a double stranded or complementary region. In one embodiment, one or both overhangs and/or one or both caps may optionally also be included. RNAi active agent is used to induce RNA interference of VGSC β3.

(B) Target and Complementary Sequences

The RNAi agent of the present disclosure targets (e.g., specifically binds, annealing, etc.) the mRNA of the encoding gene of VGSC β3. The use of a VGSC β3-specific RNAi agent results in a decrease in VGSC β3 activity, level and/or expression, such as a knock-down or knock-out target gene or target sequence. In particular, in one embodiment, the RNAi active agent directed against VGSC β3 is administered to knock down the VGSC β3 gene to a level sufficient to restore normal level of VGSC β3 activity and/or normal $Na^+$ reabsorption level in conditions where the disease state is characterized by overexpression or hyperactivity of VGSC β3.

As used herein, a "target sequence" or "target gene" refers to a contiguous portion of the nucleotide sequence of an mRNA molecule that is formed during transcription of a gene (e.g., a gene encoding a VGSC β3 protein), including the mRNA which is the RNA processing product of the primary transcript. The target portion of the sequence will be at least long enough to serve as a substrate for cleavage directed by the iRNA at the portion or near the portion. For example, the target sequence will typically be 9-36 nucleotides ("nt") long, for example 15-30 nt long, including all sub-regions therebetween. As a non-limiting example, the target sequence may be 15-30 nt, 15-26 nt, 15-23 nt, 15-22 nt, 15-21 nt, 15-20 nt, 15-19 nt, 15-18 nt, 18-22 nt, 19-30 nt, 19-30 nt, 19-26 nt, 19-23 nt, 18-22 nt, 19-22 nt, 19-21 nt, 19-20 nt, 19 nt, 20-30 nt, 20-26 nt, 20-25 nt, 20-24 nt, 20-23 nt, 20-22 nt, 20-21 21-30 nt, 21-26 nt, 21-25 nt, 21-24 nt, 21-23 nt or 21-22 nt, 21 nt, 22 nt, or 23 nt. The sense and antisense strands of RNAi comprise a sequence complementary to the target nucleic acid VGSC β3.

As used herein, and unless otherwise specified, the term "complementary" means that an oligonucleotide or polynucleotide comprising a first nucleotide sequence, under certain conditions, binds to an oligonucleotide or polynucleotide comprising a second nucleotide sequence to form a duplex structure. Such conditions may, for example, be stringent, e.g. 400 mM NaCl, 40 mM PIPES pH 6.4, 1 mM EDTA, 50° C. or 70° C. for 12-16 hours followed by washing. Other conditions, such as physiologically relevant conditions that may be encountered in an organism, may also be applied. The skilled person will be able to determine the set of conditions that are most suitable for testing the complementarity of the two sequences based on the end use of the hybridized nucleotides.

A "complementary" sequence, as used herein, may also include non-Watson-Crick base pairs and/or base pairs formed from unnatural and modified nucleotides, or entirely non-Watson-Crick base pairs and/or base pairs formed from unnatural and modified nucleotides, as long as the above requirements regarding their hybridization ability can be met. Such non-Watson-Crick base pairs include, but are not limited to, G:U Wobble or Hoogstein base pairing.

The terms "complementary", "fully complementary" and "substantially complementary" may also be used herein to refer to a base pairing between the sense and antisense strands of a dsRNA or between the antisense strand of an RNAi active agent and a target sequence, as understood in the context of its use.

As used herein, a polynucleotide that is "substantially complementary to at least a portion" of the messenger RNA (mRNA) refers to a polynucleotide that is substantially complementary to a contiguous portion of a target mRNA, such as an mRNA encoding VGSC β3. For example, a polynucleotide is complementary to at least a portion of the VGSC β3 mRNA if the sequence is substantially complementary to the non-breaking portion of the mRNA encoding VGSC β3.

The complementary sequence within an RNAi agent (e.g., within a dsRNA as described herein) includes an oligonucleotide or polynucleotide comprising a first nucleotide sequence and an oligonucleotide or polynucleotide comprising a second nucleotide sequence are base paired over the full length of one or two nucleotide sequences. Such sequences may be referred to herein as being "fully complementary" to each other. However, when the first sequence is referred to herein as being "substantially complementary" to the second sequence, the two sequences may be fully complementary, or when hybridizing to duplexes of up to 30 base pairs, they may form one or more, but usually no more than 5, 4, 3 or 2 mismatched base pairs, but remain capable of hybridizing under the conditions most relevant to their end use (e.g., inhibition of gene expression via the RISC pathway). However, when two oligonucleotides are designed to form one or more single-stranded overhangs during hybridization, such overhangs will not be considered mismatches when determining complementarity. For example, for purposes described herein, a duplex comprising one oligonucleotide having a length of 21 nucleotides and another oligonucleotide having a length of 23 nucleotides (wherein the longer oligonucleotide comprises a sequence of 21 nucleotides that is fully complementary to the shorter oligonucleotide) can still be considered "fully complementary". The term overhang describes nucleotides that are not paired at the 3' or 5' end of a double stranded nucleotide duplex, as described above. In one embodiment, the overhang is 0 to 4 nt long and is located at the 3' end.

Thus, the RNAi agent of the present disclosure is complementary or substantially complementary to the target sequence in the target VGSC β3 and is double-stranded, comprising a sense strand and an antisense strand (which may be contiguous, connected via a loop, or linked), wherein the double-stranded region is 9 to 36 bp in length (in particular e.g. 19-22 bp or 19-23 bp in length) and may further optionally comprise a 3' or 5' overhang, and the RNAi active agent may further comprise 3' cap. RNAi agents mediate RNA interference, down-regulate or inhibit the level, expression and/or activity of VGSC β3 and/or establish or reestablish almost normal ENaC level and/or VGSC β3 activity or other biological functions associated with ENaC.

(C) RNAi Active Agents that Reduce the Level, Expression and/or Activity of VGSC β3

RNAi agents for targeting VGSC β3 include agents that bind to the VGSC β3 sequences provided herein and act by RNAi mechanisms to reduce VGSC β3. Exemplary siRNAs for VGSC β3 are provided, for example, in Table 1.

The RNAi agent of the present disclosure silences, inhibits the expression of the VGSC β3 gene, down-regulates expression of the VGSC β3 gene, and/or represses expression of the VGSC β3 gene, resulting in an almost normal level of VGSC β3 activity, expression and/or level, and/or Na+ reabsorption.

In addition, in various embodiments, RNAi agents of the present disclosure may be employed to establish lower than normal level, or higher than normal level of VGSC β3 expression, activity and/or level, depending on the disease condition and the biological environment level.

Changes in VGSC β3 activity, level and/or expression induced by VGSC β3 siRNAs can be measured using any method known in the art. Measurements can be performed at multiple time points before, during, or after siRNA administration to determine the effect of siRNA.

The term "silencing", "inhibiting the expression of . . . ", "down-regulating the expression of . . . ", "repressing the expressing of . . . " and the like are referred to herein as at least partially repression of VGSC β3 gene expression when referring to the VGSC β3 gene, showed as for example: a decrease in the amount of VGSC β3 mRNA that can be isolated or detected in a first cell or group of cells in which the VGSC β3 gene is transcribed and which has been treated to inhibit the expression of the VGSC β3 gene, compared with a second cell or group of cells (control cell) that are substantially the same as the first cell or group of cells but not treated with such treatment. The degree of suppression is usually expressed as:

$$\frac{(mRNA \text{ in control cell}) - (mRNA \text{ in treated cell})}{(mRNA \text{ in treated cell})} \cdot 100\% \qquad \text{Equation 1}$$

Alternatively, the degree of inhibition can be given as a decrease in the parameters associated with VGSC β3 gene expression functions, e.g., the amount of protein encoded by the VGSC β3 gene, changes in lung fluid level or mucus level, and the like. In principle, VGSC β3 gene silencing can be determined by any appropriate assay in any cell that constitutively or genetically expresses VGSC β3. However, the assays provided in the examples below may serve as reference for determining whether a given RNAi agent inhibits VGSC β3 gene expression to such an extent that it is covered in the present disclosure and requires reference or control.

For example, in certain instances, at least about 10%, 15%, 20%, 25%, 30%, 35%, 40%, 45% and 50% of the expression of the VGSC β3 gene is inhibited by administration of the characteristic RNAi active agent in the present disclosure. In some embodiments, the VGSC β3 gene is at least about 60%, 70%, or 80% inhibited by the administration of the RNAi active agent characteristic in the present disclosure. In some embodiments, the VGSC β3 gene is inhibited by at least about 85%, 90%, or 95% or more by administration of an RNAi active agent as described herein.

The ability of an RNAi active to inhibit VGSC β3 can be tested in vitro (e.g., using a test cell such as H441) in vitro. Then, an immunostimulatory effect capable of inhibiting the RNAi active agent against VGSC β3 can be tested in vitro using, for example, PBMC (Peripheral Blood Mononuclear Cells) assay. RNAi active agents can also be tested in animal testing. Test and control animals include animals that overexpress or low express VGSC β3, described in, for example, Hummer et al., 2005 3. Am. Soc. Nephrol. 16: 3160-3166; Randrianarison et al., 2007 Am. J. Physiol. Lung Cell Phys. 294: 409-416; Cao et al., 2006 Am. J. Physiol. Renal Physiol., and references cited therein. RNAi active agents that inhibit or alter the level, activity and/or expression of VGSC β3 are useful in the treatment of a variety of VGSC β3-related diseases.

(D) Types of RNAi Active Agents and Modifications Thereof

Down-regulation of the expression of a particular protein within a cell using an RNAi active agent or composition comprising an antisense nucleic acid is generally known in the art. An RNAi active agent includes a sequence that is complementary to, and capable of being hydrogen-bounding to a coding strand (e.g., mRNA) of another nucleic acid. Thus, in various embodiments, an RNAi agent of the present disclosure encompasses any RNAi active agent that targets (e.g., is complementary thereto, is capable of hydrogen bonding to, etc.) sequences such as those shown in Table 1.

The antisense sequence complementary to the mRNA may be complementary to the coding region, the 5' or 3' untranslated region of the mRNA, and/or the region of the bridging encoding regions and untranslated regions, and/or portions thereof. In addition, an RNAi agent or part thereof may be complementary to a regulatory region of a gene encoding an mRNA, such as a transcription or translation initiation sequence or a regulatory element. In particular, a RNAi active agent or portion thereof may be complementary to a region preceding the initiation codon of the coding strand, or to a region comprising the initiation codon, or complementary to the region in the 3'untranslated region of the mRNA.

RNAi activator molecules can be designed according to Watson and Crick base pairing rules. The RNAi active agent may be complementary to the complete coding region of the VGSC β3 mRNA, but more specifically an oligonucleotide which is antisense to a portion of the coding region or non-coding region of the VGSC β3 mRNA. For example, an antisense oligonucleotide may be complementary to a region located around the translation initiation site of the VGSC β3 mRNA. The antisense oligonucleotides may be, for example, about 5, 10, 15, 19, 20, 21, 22, 23, 24, 25, 30, 35, 40, 45 or 50 nucleotides in length.

RNAi active agents may be modified internally or at one or both ends. The terminal modification can help stabilize the RNAi active agent and protect it from nuclease degradation in the blood. The RNAi agent may optionally be directed against a region known or predicted to be close to or located at the gene splicing site of the VGSC β3 mRNA; for example, an exon-intron link (for example, Saxena et al., 1998).

RNAi active agents may also optionally be designed to anneal to known or predicted exposure and/or single stranded regions (e.g., loops) of mRNA.

RNAi active agents can be constructed using procedures known in the art, using chemical synthesis and enzymatic ligation reactions. For example, naturally occurring nucleotides or modified nucleotides (designed to reduce off-target effects and/or increase the biological stability of the molecule or increase the physical stability of the duplex formed between the antisense and sense nucleic acids) may be used to chemically synthesize RNAi active agents, for example, phosphorothioate derivatives, and acridine-substituted nucleotides can be used.

"G", "C", "A", "T" and "U" each generally represent nucleotides each respectively containing guanine, cytosine, adenine, thymidine and uracil as bases. The term "ribonucleotide" or "nucleotide" may also denote a modified nucleotide or surrogate replacement moiety. It is well known to those skilled in the art that guanine, cytosine, adenine and uracil can be replaced by other moieties without substantially altering the base pairing properties of oligonucleotides containing nucleotides having such substitutions. For example and without limitation, nucleotides comprising inosine as their base may be paired with a nucleotide base containing adenine, cytosine, or uracil. Thus, nucleotides containing uracil, guanine, or adenine may be replaced by nucleotides containing, for example, inosine, in the nucleotide sequence of the dsRNA referred to in the present disclosure. In another example, adenine and cytosine at any position in the oligonucleotide may be replaced by guanine and uracil respectively to form a G-U Wobble base pair with the target mRNA. Sequences containing such substitutions are applicable to the compositions and methods described herein.

The skilled person will recognize that the term "RNA molecule" or "ribonucleic acid molecule" includes not only RNA molecules that are found or expressed in nature (i.e., naturally occurring), but also non-naturally occurring RNA analogues and derivatives comprising one or more ribonucleotide/ribonucleotide analogs or derivatives as described herein or known in the art. Strictly speaking, "ribonucleoside" includes nucleobases and riboses, and "ribonucleotides" are ribonucleosides with one, two or three phosphate moieties. However, the terms "ribonucleoside" and "ribonucleotide" may be considered to be equivalent when used herein. RNA may be modified in the nucleobase structure or in the ribose-phosphate backbone structure, for example as described herein below. However, a molecule comprising a ribonucleoside analog or derivative must retain the ability to form a duplex. As non-limiting examples, an RNA molecule may also include at least one modified ribonucleoside including, but not limited to, a 2'-O-methyl modified nucleotide, a nucleoside comprising a 5' phosphorothioate group, a terminal nucleoside linked to a cholesterol-based derivative or a dodecanoic acid dicapanoic acid amide group, a locked nucleoside, an abasic nucleoside, a 2'-deoxy-2'-fluoro-modified nucleoside, 2'-amino-modified nucleosides, 2'-alkyl modified nucleosides, morpholino nucleosides, unlinked ribonucleotides (e.g., acyclic nucleotide monomers as described in WO 2008/147824), phosphoramidates or nucleosides containing unnatural bases, or any combination thereof. Alternatively, the RNA molecule may comprise at least two modified ribonucleotides, at least 3, at least 4, at least 5, at least 6, at least 7, at least 8, at least 9, at least 10, at least 15, at least 20 or more, up to the full length of the dsRNA molecule. For each of the plurality of modified ribonucleosides in the RNA molecule, the modifications need not be the same. In one embodiment, the modified RNA considered for use in the methods and compositions described herein is peptide nucleic acid (PNA) which has the ability to form the desired duplex structure and allows or mediates the specific degradation of the target RNA via the RISC pathway.

Examples of modified nucleotides that may be used to generate RNAi active agents include 5-fluorouracil, 5-bromouracil, 5-chlorouracil, 5-iodouracil, hypoxanthine, xantine, 4-acetyl cytosine, 5-(carboxyhydroxymethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosyl Q-nucleoside, 5'-methoxycarboxyethyluracil, 5-methoxyuracil, 2-methylthio-N6-isopentenyladenine, uracil-5-hydroxyacetic acid (v), wybutoxosine, pseudouracil, queosine, 2-thiocytosine, 5-methyl-2-thiouracil, 2-thiouracil, 4-thiouracil, 5-methyluracil, uracil-5-hydroxyacetic acid methyl ester, uracil-5-hydroxyacetic acid (v), 5-methyl-2-thiouracil, 3-(3-amino-3-N-2-carboxypropyl) uracil, (acp3) w and 2,6-diaminopurine.

In one embodiment, the present disclosure contemplates any modified variant of any of the RNAi active agents disclosed herein. Modified variants contain the same sequence, but may be modified to contain modifications in phosphoric acid, sugars, bases, nucleotides, and the like. For example, modified variants may contain one or more of the modified nucleotides recited herein, such as C substituted with 2'-modified Cs.

In one aspect, the modified ribonucleoside comprises deoxyribonucleoside. In this case, the RNAi active agent may comprise one or more deoxynucleosides including, for example, deoxynucleoside overhangs, or one or more deoxyribonucleotides within the double stranded portion of the dsRNA. However, it goes without saying that the term "RNAi active agent" in any case does not include double-stranded DNA molecules.

Replacing the 3' terminal nucleotide overhang segment of the 21-nt siRNA duplex with the 3' overhang of the two nucleotides with deoxyribonucleotides do not adversely affect RNAi activity. Substituting deoxyribonucleotides for up to four nucleotides at each end of the siRNA has been well tolerated, whereas complete substitution with deoxyribonucleotides results in no RNAi activity. International PCT Publication No. WO 00/44914 and Beach et al., International PCT Publication No. WO 01/68836, tentatively suggest that siRNAs can include modifications to the phosphate-sugar backbone or nucleosides to include at least one nitrogen or thia-atom. Kreutzer et al., Canadian Patent Application No. 2,359,180, also describe certain chemical modifications for dsRNA constructs to counteract the activation of double-stranded RNA-dependent protein kinase PKR, in particular 2'-amino or 2'O-methyl nucleotides, and nucleotides containing 2'-O or 4'-C methylene bridge. In addition, 3'-terminal nucleotide overhangs include dt (deoxythymidine), 2'-O, 4'-C-vinylthymidine (eT) and 2-hydroxyethyl phosphate (hp).

Parrish et al. 2000 Molecular Cell 6: 1077-1087 used long (>25 nt) siRNA transcripts to test certain chemical modifications targeting the unc-22 gene in *C. elegans*. The authors described the incorporation of thiophosphoric acid residues into these siRNA transcripts by incorporating nucleotide analogs of phosphorothioates with T7 and T3 RNA polymerases, and it was observed that RNA with two thiophosphate-modified nucleotides, as well as RNAi, also has a considerable reduction in efficacy. In addition, Parrish et al. reported that phosphorothioate modification of more than two residues in vitro allows the RNA to be largely destabilized, thereby interfering with undetectable activity. Id. at 1081. The authors also tested some modifications of the 2'-position of the nucleotide sugar in long siRNA transcripts and found that substitution of ribonucleotides with deoxynucleotides greatly reduced the interference activity, especially uridine to thymidine substitution and/or cytidine to deoxycytidine substitution. In addition, the authors tested certain base modifications, including uracil substituted with 4-thiouracil, 5-bromouracil, 5-iodouracil, and 3-(aminoallyl)-carboxylic acid and guanosine substituted with inosine in the sense and antisense strands of siRNA. Although 4-thiouracil and 5-bromouracil substitutions are shown to be permissible, Parrish reported that inosine incorporation into either strand resulted in a substantial reduction in interfering activity. Parrish also reported that 5-iodouracil and 3-(aminoallyl) uracil were incorporated into the antisense strand resulting in a substantial decrease in RNAi activity.

Those skilled in the art will recognize that siRNAs may be synthesized and modified as desired using any conventional method known in the art. (see Henschel et al., 2004 DEQOR: a web-based tool for the design and quality control of siRNA. Nucleic Acids Research 32 (Web Server Issue): W113-W120). In addition, it will be apparent to those skilled in the art that a variety of regulatory sequences (e.g. constitutive or inducible promoters, tissue specific promoters or functional fragments thereof, etc.) can be used for antisense oligonucleotides, siRNA or shRNA expression construct/carrier.

Numerous examples in the art describe sugars, bases, phosphoric acid, and backbone modifications that can be introduced into nucleic acid molecules and significantly enhance the stability and potency of their nuclease. For example, the oligonucleotides are modified to enhance stability and/or enhance biological activity by using modification of a nuclease resistance group (e.g., 2'-amino, 2'-C-allyl, 2'-fluoro, 2'-O-methyl, 2'-O-allyl, 2'-H), modification of a nucleotide base (reviews see Usman and Cedergren 1992 TIBS. 17:34; Usman et al., J. Biol. Chem. 1994 Nucleic Acids Symp. Ser. 31: 163; Burgin et al., 1996 Biochemistry 35: 14090). Sugar modification of nucleic acid molecules is extensively described in the art.

Additional modifications and conjugations of RNAi active agents have been described. Soutschek et al., 2004 Nature 432: 173-178 show conjugation of cholesterol to the 3'end of the sense strand of the siRNA molecule via a pyrrolidine linker, thereby generating covalent and irreversible conjugates. Chemical modification of the RNAi active agent (including conjugation with other molecules) can also be performed to improve in vivo pharmacokinetic residence time and efficiency.

In various embodiments, an RNAi agent for VGSC β3 comprises at least one 5'-uridine-adenine-3'(5'-ua-3') dinucleotide, wherein the uridine is a 2'-modified nucleotide; at least one 5'-uridine-guanine-3'(5'-ug-3') dinucleotide, wherein the 5'-uridine is a 2'-modified nucleotide; at least one 5'-cytidine-adenine-3'(5'-ca-3') dinucleotide, wherein the 5'-cytidine is a 2'-modified nucleotide; and/or at least one 5'-uridine-uridine-3'(5'-uu-3') dinucleotide, wherein the 5'-uridine is a 2'-modified nucleotide.

In various embodiments, the RNAi active agent comprises a 2'-modification selected from the group consisting of 2'-deoxy, 2'-deoxy-2'-fluoro, 2'43-methyl, 2'-O-methoxyethyl (2'-O-MOE), 2'-O-aminopropyl (2'-O-AP), 2'-O-dimethylaminoethyl (2'-O-DMAOE), 2'-O-dimethylamino propyl (2'-O-DMAP), 2'-O-dimethylaminoethoxyethyl (2'-O-DMAEOE), and 2'-O—N-methylacetamido (2'-O-NMA).

In another embodiment, the RNAi comprises a gap or a missing base. For example, the phosphate-sugar backbone may be present, but the base is lost.

In another embodiment, the RNAi agent has a single stranded incision (e.g., a broken or missing bond in the backbone). In various embodiments, single-stranded gaps can be in either sense or antisense strands or both strands.

The incision may, for example, produce small, internal fragmented interfering RNA, or siRNA, in the sense strand, which may have fewer off-target effects than the corresponding RNAi active agent without the incision.

The antisense nucleic acid or RNAi active agent may also have an alternative backbone such as locked nucleic acid (LNA), morpholino, peptide nucleic acid (PNA), threo-nucleic acid (TNA) or ethylene glycol nucleic acid (GNA), or it may be labeled (e.g., radiolabeled or tagged).

One chain or two chains may comprise an alternative backbone.

In another embodiment, the RNAi active agent utilized in the methods disclosed herein may comprise an α-anomeric nucleic acid molecule. An α-anomeric nucleic acid molecule forms a specific double-stranded hybrid with the complementary RNA, wherein, in contrast to the usual β-units, the strands are arranged in parallel to each other. Gaultier et al., 1987 Nucleic Acids. Res. 15: 6625-6641.

The antisense nucleic acid molecule may also comprise a 2'-o-methyl ribonucleotide (Inoue et al., 1987 Nucleic Acids Res. 15: 6131-6148) or a chimeric RNA-DNA analog (Inoue et al., 1987 FEBS Lett. 215: 327-330).

In still another embodiment, the RNAi agent is a ribozyme. Ribozymes are catalytic RNA molecules with ribonuclease activity that cleave single-stranded nucleic acids, such as mRNA, that have complementary regions to them. Thus, ribozymes [e.g., Hammerhead ribozymes (described in Haselhoff et al., 1988, Nature 334: 585-591)] can be used to catalytically cleave VGSC β3 mRNA transcripts thereby inhibiting translation of VGSC β3 mRNA.

Alternatively, gene expression may be inhibited by targeting a nucleotide sequence that is complementary to a regulatory region of VGSC β3 (e.g., a promoter and/or enhancer) to form a triple helix structure that prevents transcription of the VGSC β3 gene. Generally, refer to Helene 1991 anticancer drug DES. 6 (6): 569-84; Helene et al., 1992 Ann. N.Y. Acad. Sci. 660: 27-36; and Maher 1992, bioassays 14 (12): 807-15.

(E) Producing an RNAi Active Agent

The RNAi agent can be biologically produced using an expression vector in which the nucleic acid is subcloned in an antisense direction (i.e., the RNA transcribed from the inserted nucleic acid is in the antisense direction to the target nucleic acid). The RNAi active agent can also be biologically produced using an expression vector in which the nucleic acid is subcloned into a shRNA construct (i.e., the RNA transcribed from the inserted nucleic acid has a first region directed in a antisense direction to the target nucleic acid, including a second region of a loop or hinge, and a third region directed in a sense direction to the target nucleic acid, wherein the first and third regions of the transcript preferably hybridize to itself to form a stem-loop structure).

Methods for producing RNAi active agents are generally known in the art and are available to those of ordinary skill in the art.

Kits for the synthesis of RNAi are commercially available from, for example, New England Biolabs and Ambion.

(F) RNAi Active Agents of the Present Invention

In one embodiment of the invention, the RNAi agent is a dsRNA, preferably a double-stranded siRNA having a length of from 9 to 50 (e.g., 15-36 bp, 15-30 bp, 15-26 bp, 15-23 bp, 15-22 bp, 15-21 bp, 15-20 bp, 15-19 bp, 15-18 bp, 15-17 by, 18-30 bp, 18-26 bp, 18-23 bp, 18-22 bp, 18-21 bp, 18-20 bp, 19-30 bp, 19-26 bp, 19-23 bp, 19-22 by, 19-21 bp, 19-20 bp, 19 bp, 20-30 bp, 20-26 bp, 20-25 bp, 20-24 bp, 20-23 bp, 20-22 bp, 20-21 bp, 21-30 bp, 21-26 bp, 21-25 bp, 21-24 bp, 21-23 bp, 21-22 bp, 21 bp, 22 bp or 23 bp nucleotide length, or 9, 10, 11, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) nucleotides, comprising an antisense strand and a sense strand substantially complementary to the antisense strand, wherein the antisense strand is complementary to or hybridizes under stringent conditions to at least about 80% to 90% of the 15, 16, 17, 18, 19, 20 or 21 or more contiguous nucleotides of the nucleotide sequence of VGSC β3, or, more preferably, is complementary to or hybridizes under stringent conditions to at least about 90% to 95% of the 15, 16, 17, 18, 19, 20 or 21 or more contiguous nucleotides of the nucleotide sequence of the target gene, and most preferably, is complementary to or hybridizes under stringent conditions to at least about 95%, 96%, 97%, 98%, or 99% of the 15, 16, 17, 18, 19, 20 or 21 or more contiguous nucleotides of the nucleotide sequence of the target gene.

As used herein, the phrase "stringent hybridization conditions" or "stringent conditions" means that a probe, primer, or oligonucleotide will hybridize to its target sequence under the conditions described, but will hybridize to a minimum number of other sequences. Stringent conditions are sequence-dependent and vary with the environment. Longer sequences hybridize specifically at higher temperature to their appropriate complementary sequences. Typically, the stringent conditions are selected to be about 5° C. below the thermal chain point (Tm) of a particular sequence at defined ionic strength and pH. Tm is the temperature at which 50% of the probe complementary to the target sequence hybridizes to the target sequence equilibrates (at defined ionic strength, pH, and nucleic acid concentration). Since the target sequence is usually present in excess, at Tm, 50% of the probes hybridize to their complementary sequences to reach equilibrium. Typically, the stringent conditions may be such that the salt concentration is less than about 1.0 M sodium ion, typically about 0.01 to 1.0 M sodium ion (or other salt), pH 7.0 to 8.3, and for short probes, primers or oligonucleotides (e.g., 10-50 nucleotides) at a temperature of at least about 30° C., for longer probes, primers or oligonucleotides at a temperature of at least about 60° C. Stringent conditions can also be achieved by the addition of destabilizing agents such as formamide.

As used herein, the term "moderately stringent conditions" refers to conditions under which a probe, primer, or oligonucleotide may hybridize to its target sequence but hybridize to a limited number of other sequences. Moderately stringent conditions are sequence-dependent and vary with different environments. Moderate conditions are generally known to those skilled in the art and are described, inter alia, in Maniatis et al. (Molecular Cloning: A Laboratory Manual, Cold Spring Harbor Laboratory; 2nd edition (December 1989)).

The present invention also relates to a nucleic acid, an expression cassette, an expression vector, and a host cell comprising the RNAi active agent.

II-2 Antibodies

In some embodiments, the VGSC β3 inhibitor is a monoclonal antibody, a polyclonal antibody, a chimeric antibody, a human antibody, a humanized antibody, a single chain antibody, or an antibody fragment, such as a Fab fragment. Antibodies against VGSC β3 are known and available in the art, such as commercially available anti-VGSCβ3 antibody by ABcam Corporation (Aibo (Shanghai) Trading Co., Ltd. Room 5401, Floor 4, Building 5, No. 338 Galileo Road, Pudong New Area, Shanghai. Postal Code: 201203), Such as antibodies mentioned in HoC et al. Differential expression of sodium channel β subunits in dorsal root ganglion sensory neurons. J Biol Chem. 2012 287 (18): 15044-15053 and Hu D et al. A mutation in the β3 subunit of the cardiac sodium channel associated with brugada ECG phenotype. Circ Cardiovasc Genet. 2009 2 (3): 270-278.

The antibody can be labeled with, for example, an enzyme, a radioactive isotope or a fluorophore. In some embodiments, the binding affinity of the antibody to a polypeptide other than VGSC β3 is less than about $1 \times 10^5$ Ka. In some embodiments, the VGSC β3 inhibitor is a monoclonal antibody that binds to VGSC β3 with an affinity of at least $1 \times 10^8$ Ka.

As used herein, the term "antibody" refers to a monoclonal and polyclonal antibody, single chain antibody, chimeric antibody, bifunctional/bispecific antibody, humanized antibody, human antibody specific for a target protein or fragment thereof, and a complementarity determining region (CDR) grafted antibody. The term "antibody" also includes in vivo therapeutic antibody gene transfer. The present invention also provides antibody fragments, including Fab, Fab', F (ab')2, scFv and Fv.

As used herein, the term "monoclonal antibody" refers to an antibody that is obtained from a population of substantially homogeneous antibodies, i.e., the individual antibodies comprising the population are identical except for possible naturally occurring mutations present in small quantities. Monoclonal antibodies are highly specific for a single antigenic site. In addition, each monoclonal antibody is directed against a single determinant of the antigen, as opposed to polyclonal antibody preparations comprising different antibodies directed against different determinants (epitopes). In addition to their specificity, monoclonal antibodies have the advantage that they can be synthesized without being contaminated by other antibodies. The modifier "monoclonal" refers to a feature of an antibody that is obtained from a substantially homogeneous population of antibodies, and is not considered to require production of antibodies by any particular method. For example, a monoclonal antibody for use in accordance with the present invention may be prepared by a hybridoma method first described in Kohler et al., Nature 256: 495 (1975), or may be produced by recombinant DNA methods (see, e.g., U.S. Pat. No. 4,816,567). Monoclones can also be isolated from phage antibody libraries using techniques such as those described in Clackson et al., Nature 352: 624-628 (1991) and Marks et al., J. Mol. Biol. 222: 581-597 (1991) antibody".

The monoclonal antibodies herein specifically include "chimeric" antibodies and fragments of such antibodies as long as they exhibit desirable biological activity in which a portion of the heavy and/or light chain is identical or homologous to the corresponding sequence of the antibody which is derived from a particular species or belonging to a particular antibody class or subclass and the remaining strand is identical or homologous to the corresponding sequence of an antibody derived from another species or belonging to another antibody class or subclass (U.S. Pat. No. 4,816,567; and Morrison et al., Proc. Natl. Acad. Sci. USA, 81: 6851-6855 (1984)). Target chimeric antibodies herein include "primatized" antibodies comprising variable region domain antigen binding sequences derived from non-human primates (e.g., old world monkeys, anthropoids, etc.) and humans;

"Antibody fragment" includes a portion of an intact antibody, preferably including its antigen binding or variable region. Examples of antibody fragments include Fab, Fab', F (ab') 2 and Fv fragments; diabodies; linearized antibodies (Zapata et al., Protein Eng. 8 (10): 1057-1062 [1995]); single chain antibody molecules; and multispecific antibodies formed from antibody fragments.

In some embodiments, the antibody of the invention is a humanized antibody. Humanized antibodies can be achieved by a variety of methods including, for example, (1) non-human complementarity determining region (CDR) is transplanted into human framework regions and constant regions (procedures known in the art as "humanized") or alternatively (2) the entire non-human variable domain is grafted, but by "cloaking" them by replacing surface residues with human-like surfaces (a process known in the art as "veneering"). In the present invention, humanized antibodies may include "humanized" and "veneered" antibodies. Similarly, a human antibody can be produced by introducing a human immunoglobulin locus into a transgenic animal, e.g., a mouse in which the endogenous immunoglobulin gene is partially or completely inactivated. Human antibody production is observed based on stimulation, which in all respects was rigorously modeled in humans, including gene rearrangement, aggregation, and antibody profiles. This method is described, for example, in U.S. Pat. Nos. 5,545,807, 5,545,806, 5,569,825, 5,625,126, 5,633425, 5,661,016 and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); Jones et al., Nature 321:522-525 (1986); Morrison et at, Proc. Natl. Acad. Sci, U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991), each of which is incorporated herein by reference.

In some embodiments, an antibody of the present invention may act as an inhibitor/antagonist of a polypeptide of the present invention.

The antibodies of the present invention may be used alone or in combination with other compositions. The antibody may also be recombinantly fused to the heterologous polypeptide at the N- or C-terminus, or chemically conjugated to the polypeptide or other composition (including covalent and non-covalent conjugations). For example, the antibodies of the present invention may be recombinantly fused or conjugated as molecules and effector molecules used to detect markers in assays, such as heterologous polypeptides, drugs, radionuclides or toxins. See, for example, PCT publications WO 92/08495; WO 91/14438; WO 89/12624; U.S. Pat. No. 5,314,995; and EP 396,387.

In addition to the chimeric and humanized antibodies, a fully human antibody can be derived from transgenic mice having human immunoglobulin genes (see, e.g., U.S. Pat. Nos. 6,075,181, 6,091,001 and 6,114,598, incorporated herein by reference), or from a phage display library of human immunoglobulin genes (see e.g., McCafferty et al., Nature, 348:552□554 (1990) Clackson et al., Nature, 352: 624□628 (1991), and Marks et al., 3. Mol. Biol., 222:581-597 (1991)). In some embodiments, an antibody can be produced and identified by an scFv-phage display library. Antibody phage display library technology is available from commercial sources, such as Xoma (Berkeley, Calif.).

Monoclonal antibodies can be prepared using the method of Kohler et al., (1975) Nature 256: 495-496, or modifications thereof. In general, mice are immunized with solutions containing the antigen. The immunization may be carried out by mixing or emulsifying the antigen-containing solution in saline, preferably in an adjuvant such as Freund's complete adjuvant and parenteral injection of the mixture or emulsion. Monoclonal antibodies of the present invention can be obtained using any immunization method known in the art. After immunizing the animal, the spleen (optionally, some large lymph nodes) is removed and isolated into single cells. Splenocytes are selected by applying a cell suspension to a plate or well coated with the antigen of interest. B cells expressing antigen-specific membrane-bound immunoglobulins bind to the plate and are not washed away. Then, the obtained B cells or all the dissociated splenocytes are induced to fuse with the myeloma cells to form hybridomas and cultured in a selective medium. The production of antibodies that specifically bind to the antigen of interest (and does not bind unrelated antigens) is determined by cells obtained by serial or limited dilution, and plating. The selected hybridomas secreting monoclonal antibodies (mAbs) are then cultured in vitro (e.g., in tissue culture flasks or hollow fiber reactors) or in vivo (in mouse ascites).

As an alternative to using hybridoma expression, antibodies can be produced in cell lines such as CHO or myeloma cell lines, as disclosed in U.S. Pat. Nos. 5,545,403; 5,545,405 and 5,998,144; all incorporated herein by reference. Briefly, cell lines were transfected with vectors capable of expressing light and heavy chains, respectively. Chimeric antibodies can be produced by transfection of two proteins on different vectors. Immunol. 147: 8; Banchereau et al., (1991) Clin. Immunol. Spectrum 3: 8; and Banchereau et al., (1991) Science 251: 70, all incorporated herein by reference.

Human antibodies can be produced using techniques known in the art, including phage display libraries (Hoogenboom and Winter, J. Mal. Biol., 227:381 (1991); Marks et al., C. J. Mol. Biol., 222:581 (1991)). The techniques of Cole et al. and Boerner et al. can also be used to prepare human monoclonal antibodies. (Cole et al., Monoclonal Antibodies and Cancer Therapy, Alan R. Liss, page 77 (1985) and Boerner et al., J. Immunol., 147(1):86 95 (1991)). Humanized antibodies can be achieved by a variety of methods including, for example, (1) non-human complementarity determining region (CDR) is transplanted into human framework regions and constant regions (procedures known in the art as "humanized") or alternatively (2) the entire non-human variable domain is grafted, but by "cloaking" them by replacing surface residues with human-like surfaces (a process known in the art as "veneering"). In the present invention, humanized antibodies may include "humanized" and "veneered" antibodies. Similarly, a human antibody can be produced by introducing a human immunoglobulin locus into a transgenic animal, e.g., a mouse in which the endogenous immunoglobulin gene is partially or completely inactivated. Human antibody production is observed based on stimulation, which in all respects was rigorously modeled in humans, including gene rearrangement, aggregation, and antibody profiles. This method is described, for example, in U.S. Pat. Nos. 5,545,807, 5,545,806, 5,569,825, 5,625,126, 5,633,425, 5,661,016 and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); Jones et al., Nature 321:522-525 (1986); Morrison et al., Proc. Natl. Acad. Sci, U.S.A., 81:6851-6855 (1984); Morrison and Oi, Adv, Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991), which are incorporated herein by reference. Fully humanized antibodies can be identified in screening assays using commercially available sources such as Morphosys (Martinsried/Planegg, Germany).

Humanized antibodies can also be produced using modified transgenic animals containing human immunoglobulin loci. For example, WO98/24893 discloses transgenic animals having a human Ig locus in which the animal does not produce a functional endogenous immunoglobulin due to inactivation of the endogenous heavy and light chain loci. WO 91/10741 also discloses a transgenic non-primate mammalian host capable of producing an immune response to an immunogen, wherein the antibody has a primate constant region and/or a variable region, and wherein the locus encoding an endogenous immunoglobulin is replaced or inactivated. WO 96/30498 discloses modifying the immunoglobulin locus of a mammal using the Cre/Lox system, for example replacing all or a portion of a constant or variable region to form a modified antibody molecule. WO94/02602 discloses non-human mammalian hosts with an inactivated endogenous Ig locus and a functional human Ig locus. U.S. Pat. No. 5,939,598 discloses a method of making a transgenic mouse in which the mouse lacks an endogenous heavy chain and expresses an exogenous immunoglobulin locus comprising one or more heterologous constant regions. Antibodies of the invention can also be produced using the human modification techniques disclosed in U.S. Pat. No. 5,766,886, which is incorporated herein by reference.

With the transgenic animal described above, an immune response against a selected antigen molecule can be produced, and antibody producing cells can be removed from an animal and used for producing a hybridoma secreting a human monoclonal antibody. Immunization protocols, adjuvants, and the like are known in the art for immunizing transgenic mice as described in WO96/33735, for example. The ability of a monoclonal antibody to inhibit or neutralize the biological activity or physiological effect of a corresponding protein can be tested.

The antibodies of the invention can be administered to a subject by the in vivo therapeutic antibody gene transfer discussed in Fang et al., (2005), Nat. Biotechnol. 23, 584-590. For example, a recombinant vector may be produced to deliver a polycistronic expression cassette comprising a peptide that mediates enzyme-independent, co-translational autologous cleavage of the polypeptide, which is located between MAb heavy and light chain coding sequences. The expression produces two Mab chains in a stoichiometric amount. A preferred example of an enzyme-independent, co-translational autologous cleavage peptide is the foot-and-mouth disease derived 2A peptide.

In some embodiments, the antibody fragment retains the ideal affinity of the full length antibody. Thus, in some embodiments, a fragment of an anti-VGSC β3 antibody retains the ability to bind VGSC β3. Such fragments are characterized by properties similar to those of the corresponding full-length anti-VGSC β3 antibodies, i.e. the fragments specifically bind to the human VGSC β3 antigen expressed on the surface of human cells In some embodiments, the antibody binds to one or more epitopes of VGSC β3. In some embodiments, the antibody modulates one or more VGSC β3-related biological activities. In some embodiments, the antibody inhibits the growth of one or more cancer cells, tumor formation, and cancer cell proliferation.

II-3 Antisense Oligonucleotides

According to one or more embodiments of the invention, antisense therapy is a form of treatment for genetic disorders or infections. When the genetic sequence of a particular gene is known to be the cause of a particular disease, a nucleic acid strand (DNA, RNA, or chemical analog) that binds to and inactivates the messenger RNA (mRNA) produced by the gene can be synthesized and thereby "shutting" the gene. This is because the mRNA must be single stranded for translation. This synthetic nucleic acid is referred to as an "antisense" oligonucleotide since its base sequence is complementary to the messenger RNA (mRNA) of the gene, the latter known as the "sense" sequence (In this way, the sense mRNA segment "5'-AAGGUC-3'" can be blocked by the antisense mRNA segment "3'-UUCCAG-5'").

In some embodiments, the oligonucleotide is complementary to the region, domain, portion, or fragment of the VGSC β3 gene or gene product. In some embodiments, the oligonucleotide comprises from about 5 to about 100 nucleotides, from about 10 to about 50 nucleotides, from about 12 to about 35 nucleotides, and from about 18 to about 25 nucleotides. In some embodiments, the oligonucleotides are at least 50%, at least 75%, at least 80%, at least 90%, at least 95%, at least 96%, at least 90%, at least 90%, at least 97%, at least 98%, at least 99%, or 100% homologous to the region, portion, domain, or fragment of the VGSC β3 gene or gene product. In some embodiments, at least 15, 20, 25, 30, 35, 40, 50 or 100 contiguous nucleotides of the VGSC Beta 3 gene or gene product have substantial or complete sequence homology. In some embodiments, the full-length VGSC β3 gene or gene product has substantial or complete sequence homology.

In some embodiments, the oligonucleotide hybridizes to a nucleic acid molecule having the nucleotide sequence of SEQ ID NO: 2 under moderate or stringent hybridization conditions.

II-4 Mimetics

In some embodiments, the VGSC β3 inhibitor is a mimetic. As used herein, the term "mimetic" refers to a compound that mimics the activity of a peptide. A mimetic is not a peptide, but may comprise an amino acid linked by a non-peptide bond. U.S. Pat. No. 5,637,677, filed Jun. 10, 1997, and its parent application, which are incorporated herein by reference in their entireties, include detailed guidance for the production of mimetics. Briefly, the three-dimensional structure of the peptide is replicated by a molecule that is not a peptide that specifically interacts with the three-dimensional structure of VGSC β3.

II-5 Small Molecules

In some embodiments, the VGSC β3 inhibitor is a small molecule. As used herein, the term "small molecule" refers to an organic or inorganic non-polymeric compound having a molecular weight of less than about 10 kilodaltons. Examples of small molecules include peptides, oligonucleotides, organic compounds, inorganic compounds, and the like. In some embodiments, the small molecule has a molecular weight of less than about 9, about 8, about 7, about 6, about 5, about 4, about 3, about 2, or about 1 kilodalton.

In some embodiments, the VGSC ββ3 inhibitor is a (poly) peptide. In a preferred embodiment, the peptide is an analgesic antineoplastic valine (AGAP). In this content, analgesic antineoplastic valine is an active peptide isolated and purified from scorpion venom of scorpionia scaberi. Its gene can be cloned from scorpionia scaberi. The gene sequence number in GENBANK is AF464898.

In one embodiment, the gene encoding AGAP is cloned into an *E. coli* expression vector, transformed into *E. coli* cells, and a recombinant bacterium is constructed to express the active peptide in *E. coli*, which is purified by chromatography to obtain recombinant analgesic antineoplastic valine; in vivo experiments showed that the active peptide has antitumor activity and analgesic activity (Liu Y Fl, Ma R L, Wang S L, Duan Z Y, Zhang J H, Wu L T, Wu C F. Expression of an antitumor-analgesic peptide from the venom of Chinese scorpion *Buthus martensii* karsch in *Escherichia coli*. Protein Expr Purif. 2003 February; 27(2): 253-8; Qinghong Mao,1 Jiaping Ruan,1,* Xueting Cai,1,2 Wuguang Lu,1,2 Juan Ye,1,2 Jie Yang,1,2 Yang Yang,1,2 Xiaoyan Sun,1,2 Junli Cao,3 and Peng Cao1,2,*Published online Nov. 14, 2013. doi: 10.1371/journal.pone. 0078239PMCID: PMC3828337 Antinociceptive Effects of Analgesic-Antitumor Peptide (AGAP), a Neurotoxin from the Scorpion *Buthus martensii* Karsch, on Formalin-Induced Inflammatory Pain through a Mitogen-Activated Protein Kinases-Dependent Mechanism in Mice PLoS One. 2013; 8(11): e78239). In vitro experiments showed that the active peptide inhibited the proliferation and migration of human malignant glioma cell line SHG-44 (Zhao Y, Cai X, Ye T, Huo J, Liu C, et al., (2011) Analgesic-antitumor peptide inhibits proliferation and migration of SHG-44 human malignant glioma cells. J Cell Biochem 112: 2424-2434).

III. Tumors

As used herein, "tumor" refers to any tissue mass resulting from excessive cell growth or proliferation, or benign (non-cancerous) or malignant (cancerous), including precancerous lesions.

As used herein, "cancer" refers to primary or metastatic cancer, leukemia, or lymphoma. The term "cancer cell" refers to a transformed cell. These cells can be isolated from patients suffering from cancer, or these cells are transformed into cancerous cells in vitro. The cancer cells can be derived from a variety of types of samples, including any tissue or cell culture system. In some embodiments, the cancer cells are hyperplastic, tumor cells or neoplasms. In some embodiments, the cancer cells are isolated from liver cancer, lung cancer, colon cancer, testicular cancer, thymic cancer, breast cancer, skin cancer, esophageal cancer, pancreatic cancer, prostate cancer, uterine cancer, cervical cancer, bladder cancer, ovarian cancer, multiple myeloma and melanoma. In some embodiments, the cancer cell is taken from a publicly available cell line that is already present. In some embodiments, the cancer cells are isolated from an existing patient sample, or isolated from a library comprising cancer cells. In some embodiments, the cancer cells are isolated and then implanted into different hosts, such as xenografts. In some embodiments, the cancer cells are transplanted and used in SCID mouse models. In some embodiments, the cancer is liver cancer, lung cancer, or leukemia.

Particular examples of tumors that can be treated by the methods and compositions of the invention, in particular cancers include, but are not limited to, VGSC β3-related tumors, particularly VGSC β3-related cancers. As used herein, a "VGSC β-related tumor" refers to any tumor that involves the level, expression and/or activity of VGSC β3, and/or any other tumor that can be modulated (particularly inhibited) by the level, expression and/or active treatment and/or remission of the tumor. In particular, "VGSC β3-related cancer" refers to a cancer characterized by a differential (especially increased) expression of VGSC β3 relative to non-cancerous cells. The present invention is also applicable to any tumor cell type in which VGSC β3 functions in the growth of cancer cells and the like. In some embodiments, the cancers are leukemia, colon cancer, liver cancer, testicular cancer, thymic cancer, breast cancer, skin cancer, esophageal cancer, pancreatic cancer, prostate cancer, uterine cancer, cervical cancer, lung cancer, bladder cancer, ovarian cancer, multiple myeloma and melanin tumor. In some embodiments, the cancer is liver cancer, leukemia or lung cancer. In some embodiments, such cancers exhibit at least about 25%, at least about 50%, at least about 75%, at least about 100%, at least about 150%, at least about 200%, or at least about 300% differential expression of VGSC β3 (especially increased expression) relative to a control.

VI. Pharmaceutical Compositions

As used herein, "pharmaceutical composition" includes a pharmaceutically effective amount of one or more VGSC β3 inhibitors, a pharmaceutically acceptable carrier, and optionally other tumor therapeutic agents in synergy with the VGSC β3 inhibitor. As used herein, "pharmaceutically effective amount", "therapeutically effective amount", or a simple "effective amount" means an amount of a VGSC β3 inhibitor that is effective to produce the desired pharmacological, therapeutic or prophylactic results. For example, if a measurable parameter associated with a disease or condition has a decrease of at least 10%, then a given clinical treatment is considered to be effective and a therapeutically effective amount of a medicament for treating said disease or condition is an amount necessary to cause said parameter to produce a decrease of at least 10%. In this embodiment, a therapeutically effective amount of a VGSC β3 inhibitor targeted to VGSC β3 may reduce the VGSC β3 protein level by at least 10%. In other embodiments, a given clinical treatment is considered to be effective when there is a reduction of at least 15, 20, 25, 30, 35, 40, 45, 50, 55, 60, 65, 70, 75, 80, 85, 90, or 95% in measurable parameters associated with the disease or condition, and a therapeutically effective amount of a medicament for treating the disease or condition is an amount necessary to produce a reduction of the parameter by at least 15, 20, 25, 30, 35, 40, 45, 50, 55, 60, 65, 70, 75, 80, 85, 90, or 95%, respectively.

The term "pharmaceutically acceptable carrier" refers to a carrier to which a therapeutically active agent is administered. Such carrier includes, but is not limited to, saline, buffered saline, dextrose, water, glycerol, ethanol, and combinations thereof. The term expressly excludes cell culture media. For a medicament administered orally, pharmaceutically acceptable carriers include, but are not limited to, pharmaceutically acceptable excipients such as inert diluents, disintegrants, binders, lubricants, sweeteners, flavoring agents, coloring agents and preservatives. Suitable inert diluents include sodium and calcium carbonates, sodium and calcium phosphates, and lactose, while corn starch and alginic acid are suitable disintegrants. The binder may include starch and gelatin, and the lubricant, if present, is typically magnesium stearate, stearic acid or talc. If desired, the tablet may be coated with a material such as glyceryl monostearate or glyceryl distearate to delay absorption in the gastrointestinal tract. The active agents included in the pharmaceutical formulations are also described herein.

A pharmaceutical composition comprising a VGSC β3 inhibitor may be in solid form, such as a powder, granules, tablets, pills, soft capsules, capsules, liposomes, suppositories, chews or patches. Pharmaceutical compositions comprising a VGSC β3 inhibitor may also be presented in liquid form, such as solutions, emulsions, suspensions, elixirs or syrups. Suitable liquid supports may be, for example, water, organic solvents (e.g., polyols such as glycerol or ethylene glycol, including propylene glycol and polyethylene glycol) or ethanol, Cremophor EL or mixtures thereof (in a variety of proportions, in water). The composition may comprise nano-sized amorphous or crystalline particles, which are coated with aluminum or a surfactant.

Suitable supports may include, for example, antibacterial and antifungal agents, buffers, calcium phosphate, cellulose, methylcellulose, chlorobutanol, cocoa butter, colorants, dextrins, emulsions, enteric coatings, flavoring agents, gelatin, isotonic agents, lecithin, magnesium stearate, aromatics, polyalcohols such as mannitol, injectable organic esters such as ethyl oleate, paraben, phenol sorbic acid, poly ethylene glycol, polyvinylpyrrolidine, phosphate buffered saline (PBS), preservatives, propylene glycol, sodium carboxymethyl cellulose, sodium chloride, sorbitol, various sugars including but not limited to sucrose, fructose, galactose, lactose and trehalose, starch, suppository wax, talc, vegetable oils such as olive and corn oil, vitamins, waxes and/or wetting agents. For VGSC β3 inhibitors, preferred supports include dextran and water, for example, 5% dextrose in water (D5W).

The biologically inert portion of the pharmaceutical composition may optionally be erodible to allow release of the VGSC β3 inhibitor over time.

The pharmaceutical compositions may include other components that contribute to delivery, stability, efficacy, or reduced immunogenicity.

VI-1. Administration of VGSC β3 Inhibitors

A pharmaceutical composition comprising a VGSC β3 inhibitor may be administered by buccal, inhalation (including insufflation or deep inhalation), nasal, oral, parenteral, implantable, injection or infusion (via epidural, intraarterial, intraarticular, intracapsular, intracardiac, intracerebroventricular, intracranial, intradermal, intramuscular, intraorbital, intraperitoneal, intraspinal, intrasternal, intrasternal, intrathecal, intravenous, subarachnoid, subcapsular, subcutaneous, sub epidermal, endothelial, tracheal, vascular, rectal, sublingual, topical and/or vaginal route). This can be done by injection, infusion, skin patch or any other method known in the art. The formulations may be powdered, aerosolized, aerosolized, pelleted or suitably prepared for delivery. If it is a liquid, administration may be performed slowly or by bolus injection, although in some cases known in the art, bolus injection may result in renal loss of the material.

A pharmaceutical composition comprising a VGSC β3 inhibitor can be administered using a medical device known in the art. For example, in certain embodiments, a VGSC β3 inhibitor can be administered with a needleless hypodermic injection device such as disclosed in U.S. Pat. No. 5,399, 163; 5,383,851; 5,312,335; 5,064,413; 4,941,880; 4,790, 824; or 4,596,556. Examples of well-known implants and modules that can be used in the present disclosure include U.S. Pat. No. 4,487,603, which discloses an implantable microinfusion pump for dispensing medicament at a controlled rate; U.S. Pat. No. 4,486,194, which discloses a therapeutic device for administering a medicament via the skin; U.S. Pat. No. 4,447,233, which discloses a pharmaceutical infusion pump for delivering an agent at a precise infusion rate; U.S. Pat. No. 4,447,224, which discloses a variable flow rate implantable infusion device for continuous drug delivery; U.S. Pat. No. 4,439,196 which discloses a permeable drug delivery system having a multi-lumen compartment; and U.S. Pat. No. 4,475,196, which discloses a permeable drug delivery system. Many other such implants, delivery systems and modules are known to those skilled in the art.

In certain embodiments, a pharmaceutical composition comprising a VGSC β3 inhibitor can be formulated to ensure proper distribution in vivo. Administration of a VGSC β3 inhibitor against VGSC β3 can be systemic (systemic) or in particular tissues or organs targeted to express (or overexpress or overactivate) VGSC β3 such as lung, kidney, colon and gland. Methods for targeting these specific tissues or organs are described herein and/or are known in the art. For example, they may be formulated in liposomes. For methods of making liposomes, see, for example, U.S. Pat. Nos. 4,522,811; 5,374,548 and 5,399,331. Liposomes may comprise one or more moieties selectively transported into a particular cell or organ, thereby enhancing targeted drug delivery (see, e.g., V. V. Ranade (1989) *J. Clin. Pharmacol,* 29: 685).

Examples of targeted moieties include folic acid or biotin (See, e.g., Low et al, U.S. Pat. No. 5,416,016); mannoside (Umezawa et al., (1988) *Biochem. Biophys. Res. Commun.* 153: 1038); antibiotics (P. G. Bloeman et al. (1995) *FEBS Lett.* 357: 140; M. Owais et al. (1995) *Antimicrob. Agents Chemother.* 39: 180); surfactant protein A receptors (Briscoe et al. (1995) *Am. J. Physiol.* 1233: 134), different classes of which may comprise the formulations of the present disclosure and the components of the inventive molecules; p120 (Schreier et al. (1994) *J. Biol. Chem.* 269: 9090); See also K. Keinanen; M. L. Laukkanen (1994) *FEBS Lett.* 346: 123; J. J. Killion; I. J. Fidler (1994) *Immunomethods* 4: 273.

Thus, the present disclosure encompasses a pharmaceutical composition comprising one or more VGSC β3 inhibitors directed against VGSC β3, which may optionally contain a plurality of modifications and/or other components for the treatment of VGSC β3-related diseases.

VI-2 Dosage and Effective Amount of VGSC β3 Inhibitors

Administering to a Patient in Need Thereof a Therapeutically Effective Amount of a VGSC β3 Inhibitor of the Present Disclosure.

"Effective amount" or "therapeutically effective amount" is an amount that treats an individual's disease or medical condition, or more generally, provides a nutritional, physiological or medical benefit to the individual. As used herein, the phrase "therapeutically effective amount" and "prophylactically effective amount" represent an amount that provides a therapeutic benefit in the treatment, prevention or management of a pathological process mediated by VGSC β3 expression or a distinct symptom of a pathological process mediated by VGSC β3 expression. The specific therapeutically effective amount can be readily ascertained by the general practitioner and may vary depending on factors known in the art such as the type of pathological process mediated by VGSC β3 expression, the patient's medical history and age, the stage of pathological process mediated by β-ENaC expression, as well as administration of other active agents that inhibit the pathological process mediated by VGSC β3 expression.

In various embodiments of the present disclosure, a patient is at least about 1, 3, 6 or 9 months, or 1, 5, 10, 20, 30, 40, 50, 55, 60, 65, 70, or 75-year-old. In various embodiments, the patient age does not exceed about 1, 3, 6 or 9 months, or 1, 5, 10, 20, 30, 40, 50, 55, 60, 65, 70, 75, or 100-year-old. In various embodiments, the patient has a weight of at least about 5, 10, 15, 20, 30, 40, 50, 60, 70, 80, 90, 100, 120, 140, 160, 180, 200, 220, 240, 260, 280, 300, 320, 340, 360, 380 or 400 lbs. In various embodiments, the patient has a weight of no more than about 5, 10, 15, 20, 30, 40, 50, 60, 70, 80, 90, 100, 120, 140, 160, 180, 200, 220, 240, 260, 280, 300, 320, 340, 360, 380 or 400 lbs.

In various embodiments of the present disclosure, the dose [measuring the active ingredient only] may be at least about 1, 5, 10, 25, 50, 100, 200, 250, 300, 350, 400, 450, 500, 550, 600, 650, 700, 750, 800, 850, 900, 950, or 1000 ng, 1, 5, 10, 25, 50, 100, 200, 250, 300, 350, 400, 450, 500, 550, 600, 650, 700, 750, 800, 850, 900, 950 or 1000 µg, 1, 5, 10, 25, 50, 100, 200, 250, 300, 350, 400, 450, 500, 550, 600, 650, 700, 750, 800, 850, 900, 950 or 1000 mg. In various embodiments, the dose may not exceed about 10, 25, 50, 100, 200, 250, 300, 350, 400, 450, 500, 550, 600, 650, 700, 750, 800, 850, 900, 950 or 1000 mg. In various embodiments, the dosage may be administered at least once per day, daily, more than once per week, per week, every other week, every month and/or every 2, 3, 4, 5, 6, 7, 8, 9, 10, 11 or 12 months, or a combination thereof.

In various embodiments, the dose is related to an individual's body weight or body surface area. Actual dosage levels may vary to obtain the amount of active agent active for a particular patient, composition and mode of administration but not toxic to the patient. The selected dose will depend on a variety of pharmacokinetic factors including the activity of the particular VGSC β3 inhibitor used, the route of administration, the VGSC β3 inhibitor excretion rate, the duration of treatment, other drugs used in combination with the VGSC β3 inhibitor, compound and/or materials, age, sex, weight, condition, general health and prior medical history of the patient, and similar factors well known in the medical arts. An effective amount of the desired VGSC β3 inhibitor can be readily determined by a physician or veterinarian having ordinary skill in the art. A suitable dose will be an amount which is the lowest dose effective for producing a therapeutic effect, or a dose that is sufficiently low to produce a therapeutic effect, but without causing side effects.

IV Prevention/Treatment of Tumors (Especially Cancer)

The present invention provides methods for the prevention and/or treatment of tumors associated with VGSC β3, such as cancer, including other active ingredients in combination with the VGSC β3 inhibitors of the invention. In some embodiments, the method further comprises administering to the patient one or more conventional cancer therapeutic agents. In some embodiments, the method of the invention further comprises treating the patient with one or more of chemotherapy, radiation therapy, hormone ablation, or surgery.

The present invention also provides methods and compositions for the treatment, suppression and management of cancer or other tumors which have been partially or completely resisted by existing or standard cancer treatments such as surgery, chemotherapy, radiation therapy, hormonal therapy and biological therapy.

The present invention provides a method for treating and/or preventing a tumor or cancer or symptom of a cancer in a subject comprising administering to the subject a therapeutically effective amount of one or more of the VGSC β3 inhibitors of the invention. In some embodiments, the cancer is a cancer associated with VGSC β3. In some embodiments, the cancer is leukemia, colon cancer, liver cancer, testicular cancer, thymic cancer, breast cancer, skin cancer, esophageal cancer, pancreatic cancer, prostate cancer, uterine cancer, cervical cancer, lung cancer, bladder cancer, ovarian cancer, multiple myeloma or melanoma. In some embodiments, the cancer is in a non-hormone-regulated tissue. In some embodiments, the subject has been diagnosed with or susceptible to cancer. In some embodiments, the cancer is liver cancer, lung cancer, or leukemia.

Symptoms of cancer are commonly known to those skilled in the art and include, but are not limited to, weight loss, anemia, abdominal pain, intestinal obstruction, blood in the stool, diarrhea, constipation, other changes in bowel habits, colon metastasis, death, weakness, fatigue, eating difficulty, loss of appetite, chronic cough, dyspnea, hemoptysis, hematuria, nausea, vomiting, liver metastasis, lung metastasis, bone metastasis, belly bulge, bloating, abdominal effusion, vaginal bleeding, abdominal distension, colon perforation, acute peritonitis (infection, fever, pain), pain, hematemesis, severe sweating, fever, high blood pressure, jaundice, dizziness, cold, muscle cramps, lung metastasis, bladder metastasis, liver metastasis, bone metastasis, renal metastasis and pancreatic metastasis, dysphagia and so on.

The therapeutically effective amount of the compound can be determined and adjusted empirically according to procedures generally known to pharmaceutical chemists, and depending on the age of the patient, the severity of the condition, and the desired final pharmaceutical formulation.

The present invention also provides a method for inhibiting cancer cell growth in a patient in need thereof comprising administering to the patient a therapeutically effective amount of one or more VGSC β3 inhibitors. Suitable assays for measuring the growth of VGSC β3-related cells are known to those of skill in the art and are presented in the context.

The present invention also provides a method for inhibiting cancer in a patient in need thereof. The method comprises administering to the patient a therapeutically effective amount of one or more VGSC β3 inhibitors.

The present invention also provides a method for inhibiting cancer in a patient diagnosed or suspected of having cancer. The method comprises administering to the patient a therapeutically effective amount of one or more VGSC β3 inhibitors.

The present invention also provides a method of modulating one or more symptoms of cancer in a patient. The method comprises administering to the patient a therapeutically effective amount of the VGSC β3 composition described herein.

The present invention also provides a method for inhibiting cell growth in a patient in need thereof, comprising administering to the patient a therapeutically effective amount of a VGSC β3 inhibitor.

The present invention also provides a method for inhibiting cancer cell migration in a patient in need thereof, comprising administering to the patient a therapeutically effective amount of a VGSC β3 inhibitor.

The present invention also provides a method for inhibiting cancer cell attachment in a patient in need thereof, comprising administering to the patient a therapeutically effective amount of a VGSC β3 inhibitor.

The present invention also provides a method of prophylactically treating a patient that is susceptible to developing cancer, metastasis of a cancer, or which already has metastasis and thus is susceptible to recurrence or reappearance. The method is particularly useful for high-risk individuals, for example having a family history of cancer or metastatic tumors, or exhibiting genetic quality for cancer metastasis. In some embodiments, the tumor is a VGSC β3-related tumor. In addition, the method is used to prevent recurrence of a VGSC β3-related tumor in a patient who had a VGSC β3-related tumor removed by surgical resection or treated with conventional cancer treatment.

The present invention also provides a method of inhibiting the progression of cancer and/or causing cancer regression comprising administering to the patient a therapeutically effective amount of a VGSC β3 inhibitor.

In some embodiments, a VGSC β3 inhibitor of the invention is used in combination with chemotherapy and/or radiotherapy to treat a patient in need of anti-cancer therapy. For example, after administration of a VGSC β3 inhibitor, a therapeutically effective amount of anti-cancer radiation therapy may also be used. In some embodiments, the combination provides chemotherapy therapy and a VGSC β3 inhibitor. In some embodiments, VGSC β3 inhibitors and chemotherapy and radiation therapy are administered in combination.

The method of treatment comprises administering to the patient a single or multiple doses of one or more VGSC β3 inhibitors. In some embodiments, the VGSC β3 inhibitor is administered as an injectable pharmaceutical composition that is sterile, non-pyrogenic and comprises a VGSC β3 inhibitor in combination with a pharmaceutically acceptable carrier or diluent.

In some embodiments, the treatment regimen of the present invention is used in conjunction with conventional treatment regimens for cancer, including but not limited to surgery, radiotherapy, hormone ablation and/or chemotherapy. Administration of the VGSC β3 inhibitor of the present invention may be performed prior to, concurrently with, or following conventional cancer therapy. In some embodiments, two or more different VGSC β3 inhibitors are administered to a patient.

In some embodiments, the amount of VGSC β3 inhibitor administered to a patient is effective to inhibit one or more of neutrophil growth, cancer cell growth, tumor formation, cancer cell proliferation, cancer cell metastasis, and VGSC β3 expression. In some embodiments, the amount of VGSC β3 inhibitor administered to a patient is effective to increase cancer cell death through apoptosis.

V. Combination Therapy

In one embodiment, the inhibitor of VGSC β3 disclosed herein is administered to a patient in need thereof along with one or more additional pharmaceutically active agents suitable for treating a tumor, in particular a cancer. For example, a patient suffering from cancer may be administered a pharmacologically effective amount of one or more inhibitors of VGSC β3 with a pharmacologically effective amount of one or more of any of the cancer treatments listed herein and/or any other cancer treatment known in the art.

In the treatment of tumors, particularly cancer, one or more inhibitors of VGSC and one or more other tumor therapeutic agents may be administered in any order, simultaneously or sequentially, or in multiple doses over time. The administration of the inhibitor of VGSC β3 and other therapeutic agents can be, for example, simultaneous, parallel, separate or sequential.

Simultaneous administration may be carried out, for example, in a fixed combination of two or more active ingredients, or may be performed by concurrently administering two or more independently formulated active ingredients. Sequential use (administration) preferably means administration of one or more of the components in a combination at a time point, the other components being administered at different time points, i.e., in a long term staggered manner, preferably such that the combination shows a higher efficiency than the individual compound alone (particularly demonstrating synergy effect). Separate use (administration) preferably means that the combined components are administered independently of each other at different time points, preferably, the components (a) and (b) are applied such that the overlapping of the measurable blood levels of the two compounds does not exist in an overlapping fashion (at the same time).

In addition, combinations of two or more of sequential, separate and simultaneous administration are possible, preferably such that the combined component-drug exhibits a combined therapeutic effect exceeding the effect found when the combination component-drug is used independently at time intervals, and the degree of superposition is so large that the mutual influence of their therapeutic efficiency cannot be found, and the synergistic effect is particularly preferable.

"Combination therapeutic activity" or "combination therapy effect" means that the compounds can be administered separately (at long-term staggered intervals, in particular a sequence-specific manner) such that they are preferably still displayed (preferably synergistic) interactions (combined therapeutic effects) in warm-blooded animals, especially humans, to be treated. Whether this is the case may be determined by monitoring the blood level, which indicates that both compounds are present in the blood of the person to be treated at least during some time interval, and so on.

In some embodiments, a conventional cancer therapeutic agent is administered with a composition of the invention. Conventional cancer therapeutic agents include:
A) a cancer chemotherapeutic agent;
B) other active agents;
C) prodrugs.

Cancer chemotherapeutic agents include, but are not limited to, alkylating agents such as carboplatin and cisplatin; nitrogen mustardising agents; nitrosoureidating agents such as carmustine (BCNU); antimetabolites such as methotrexate; formyltetrahydrofolate; purine analogue antimetabolite, mercaptopurine; pyrimidine analogue antimetabolites such as fluorouracil (5-FU) and gemcitabine (Gemzar®); hormonal antineoplastic agents such as goserelin, leuprolide and tamoxifen; natural antineoplastic agents such as ademetilin, interleukin-2, docetaxel, etoposide (VP-16), Interferon α, Taxol® and retinoic acid (ATRA); antibiotics natural antineoplastic agents, such as bleomycin, dactinomycin, daunorubicin, doxorubicin, daunomycin and mitomycin (including mitomycin C); as well as *vinca* alkaloids natural antineoplastic agents such as vinblastine, vincristine, vindesine; hydroxyurea; glucuronide; adriamycin, ifosfamide, enoxaparin, epithiolone, adriamycin, ancitabine, nimustine, procarbazine hydrochloride, carbachol, carboplatin, carmofur, coloromycin A3, antitumor polysaccharide, anti-tumor platelet factor, cyclophosphamide (Cytoxin®), sorafenine, cytosine arabinoside (cytosine arabinoside), dacarbazine, thiosine, thiotepa, tegafur, dolastatin, dolastatin analogs such as auristatin, CPT-11 (irinotecan), mitoxantrone, vinorelbine, teniposide, aminopterin, erythromycin and esperamycin (See, e.g., U.S. Pat. No. 4,675,187), new oncostatin, OK-432, Bleomycin, Fluoride, bromide uridine, busulfan, diethylstilbestrol diphosphate, peplinomycin, phenenematin (Ubenimex®), Interferon-β, mexane, dibromomannide, melphalan, laminin peptides, lentinan, *coriolus versicolor* extract, tegafur/uracil, estramustine (estrogen/nitrogen mustard).

Other active agents that can be used to treat cancer patients include EPO, G-CSF, ganciclovir; antibiotics, leuprorelin, pethidine, zidovudine (AZT); interleukins 1 to 18, including variants and analogs; interferons or cytokines, such as interferon α, β and γ; hormones such as luteinizing hormone releasing hormone (LHRH) and analogs, and gonadotropin releasing hormone (GnRH); growth factors such as transforming growth factor-β (TGF-β), fibroblast growth factor (FGF), nerve growth factor (NGF), growth hormone releasing factor (GHRF), epidermal growth factor (EGF), Fibroblast growth factor homologous factor (FGFHF), hepatocyte growth factor (HGF) and insulin growth factor (IGF); Tumor necrosis factor-α & β (TNF-α & β); invasion inhibitory factor-2 (IIF-2); bone morphogenetic protein 1-7 (BMP 1-7); somatostatin, thymosin-α-1, γ-globulin, superoxide dismutase (SOD), complement factor; antiangiogenic factor; antigenic substance; and prodrug.

"Prodrug" refers to a precursor or derivative form of a pharmaceutically active substance that is less cytotoxic or non-cytotoxic to tumor cells compared to the parent drug and can be enzymatically activated or transformed into an activated or more active parent form. See, for example, Wilman, "Prodrugs in Cancer Chemotherapy" Biochemical Society Transactions, 14, Page 375-382, 615th Meeting Belfast (1986) and Stella et al., "Prodrugs: A Chemical Approach to Targeted Drug Delivery," Directed Drug Delivery, Borchardt et al., (Eds.), Page 247-267, Humana Press (1985). Prodrugs include, but are not limited to, phosphate containing prodrugs, thiophosphate containing prodrugs, sulfate containing prodrugs, peptide-containing prodrugs, D-amino acid modified prodrugs, glycosylated prodrugs, prodrugs containing β-lactam, prodrugs containing optionally substituted phenoxyacetamide or prodrugs containing optionally substituted phenylacetamide, prodrugs containing 5-fluorocytosine or other 5-fluorouridine (which can be converted to a more activated cytotoxic free drug). Examples of cytotoxic agents that can be derivatized into prodrug forms as used herein include, but are not limited to, the above-described chemotherapeutic agents.

VII. Diagnosis/Detection of Tumors

The present invention also provides a method for diagnosing a tumor or cancer in a subject using the inventive VGSC β3 to diagnose a tumor, e.g., a cancer and/or to predict a tumor, such as cancer progression. The method comprising:

Obtaining a sample or a test cell from a subject;

Detecting protein or gene content of VGSC β3 in the sample or the test cell and a control normal cell by means of detecting a VGSC β3 DNA, mRNA or protein;

Comparing the results, higher protein or gene content of VGSC β3 in the sample or the test cell than that of the normal control indicates that the subject has a tumor.

The present invention also provides a method for diagnosing a VGSC β3-related tumor (e.g., cancer) in a subject using the VGSC β3 of the present invention, the method comprising Obtaining a sample or a tumor cell to be tested from a subject;

Detecting protein or gene content of VGSC β3 in the tumor cells to be tested and the control normal cells by means of detecting the VGSC β3 DNA, mRNA or protein;

Comparing the results, higher protein or gene content of VGSC β3 in the tumor cells to be tested than that of the control normal cell indicates that the subject had a VGSC β3-related tumor (e.g., cancer).

In one embodiment, the means for measuring the level of the encoding DNA or mRNA or protein comprises a probe or primer that can be used to measure the VGSC β3 subunit encoding DNA level or mRNA level, or a detectable antibody, small molecule, oligonucleotide, decoy, mimetics or probe that can detect the expression and activity of the VGSC β3 protein.

In one embodiment, the sample is a sample of a tissue suspected of having a tumor, preferably a tumor biopsy or a cell extract thereof.

In some embodiments, the cell extract comprises an extract of circulating cells of a solid tumor. The circulating cells are typically isolated from a patient sample using one or more separation methods known in the art, including, for example, immunomagnetic separation, CellTrack™ system, microfluidic separation, FACS, density gradient centrifugation and elimination.

In other embodiments, the patient sample includes whole blood, serum, plasma, sputum, bronchial lavage fluid, urine, nipple aspirate, lymph, saliva and/or fine needle aspirate samples. In some cases, the whole blood sample is separated into plasma or serum components and cell components (i.e., cell pellets). Cell components typically contain circulating cells of red blood cells, leukocytes, and/or solid tumors, such as CTC, CEC, CEPC, lymph node disseminated tumor cells and/or CSC and combinations thereof. A plasma or serum component typically contains nucleic acids (e.g., DNA, RNA) and proteins released by circulating cells of a solid tumor.

VIII. Kit

In some embodiments, the present invention provides a means for imaging and/or detecting a gene or gene product associated with VGSC β3 overexpression or for measuring VGSC β3 subunit encoding DNA level or mRNA level or protein expression level, and a kit comprising the means.

The means of the present invention may include a detectable antibody, a small molecule, an oligonucleotide, a decoy, a mimetic, or a probe. The kit of the present invention includes the described means and an instruction for practicing the methods of the present invention. Optionally, the kit further comprises one or more of the following: a control (positive and/or negative), control container, a photograph or description of a representative example of positive and/or negative results VIII Screening Method The present invention also provides a method for designing and preparing an active substance for preventing or treating a tumor in a subject using the VGSC β3 as a target, which comprises designing an antibody, a small molecule inhibitor, a (poly) peptide and a nucleic acid, an antisense oligonucleotide, or a mimetic capable of suppressing the VGSC β3 protein based on its amino acid sequence and nucleic acid coding sequence. The method also includes the step of preparing the active substance as designed above and determining whether it inhibits the expression, activity and/ or associated biological activity of VGSC β3. In some embodiments, inhibition of one or more cancer cell markers, such as growth of cancer cells, indicates the active substance described above. The present invention also provides for the preparation of the active substance described above as a pharmaceutical composition.

The present invention also provides a method of screening for an active substance for preventing or treating a tumor in a subject. The method comprises contacting a cell expressing VGSC β3 with a candidate compound to determine whether expression, activity and/or associated biological activity of VGSC β3 is inhibited. In some embodiments, inhibition of one or more cancer cell markers, such as growth of cancer cells, indicates the active substance described above. The present invention also provides for the preparation of the active substance described above as a pharmaceutical composition.

The present invention also provides a method for screening an anti-cancer agent or an inhibitor of tumor cell proliferation. The method comprises contacting a cell expressing VGSC β3 with a candidate compound to determine whether expression, activity and/or associated biological activity of VGSC β3 is modulated. In some embodiments, inhibition of one or more cancer cell markers, such as growth of cancer cells, indicates an anticancer agent.

IX. Definitions

In addition to the definitions referred to above, the disclosure also relates to the following definitions:

As used herein, the term "about" refers to a value of +/−20%, +/−10%, or +/−5%.

The terms "polypeptide" or "protein" are used interchangeably and refer to an amino acid polymer form of any length and may include both encoded and non-encoded amino acids, chemically or biochemically modified or derivatized amino acids, and polypeptides having modified peptide backbone. The terms include fusion proteins including, but not limited to, fusion proteins having heterologous amino acid sequences, fusions having heterologous and homologous leader sequences (with or without N-terminal methionine residues), immunologically labeled proteins; and the like.

The terms "individual", "subject", "host", and "patient" are used interchangeably and refer to any subject, particularly a human, that needs to be diagnosed, treated or treated. Other subjects may include cattle, dogs, cats, guinea pigs, rabbits, rats, mice, horses and the like. In some preferred embodiments, the subject is a human.

As used herein, the term "sample" refers to a biological material from a patient. The sample of the present invention is not limited to any particular type. Samples include, by way of non-limiting example, single cells, multicells, tissues, tumors, biological fluids, biological molecules or any of the above-mentioned extracts or supernatants. Examples include removal of tissue for biopsy, tissue removed during resection, blood, urine, lymphoid tissue, lymph, cerebrospinal fluid, mucus, and stool samples. Depending on the assay method, the detection method and the nature of the tumor, tissue, cell or extract to be assayed, the sample used can be varied. Methods for preparing samples are generally known in the art and can be conveniently adjusted for obtaining samples compatible with the methods used.

As used herein, the term "biological molecule" includes, but is not limited to, polypeptides, nucleic acids, and sugars.

A "gene product" is a biopolymerized product expressed or produced by gene. The gene product can be, for example, un-spliced RNA, mRNA, spliced variant mRNA, polypeptide, post-translationally modified polypeptide, splice variant polypeptide, and the like. The term also encompasses biopolymerized products produced using RNA gene products (i.e., RNA's cDNA) as templates. The gene product may be enzymatically, recombinantly, chemically produced, or produced in a native cell of the gene. In some embodiments, if the gene product is a protein, it exhibits a biological activity. In some embodiments, if the gene product is a nucleic acid, it can be translated into a gene product of a protein exhibiting biological activity.

As used herein, the term "biological molecule" includes, but is not limited to, polypeptides, nucleic acids, and carbohydrates.

As used herein, the terms "differential expression in cancer cells" and "polynucleotides that are differentially expressed in cancer cells" are used interchangeably herein, which refer to that when compared to cells of the same cell type that are not cancerous, the representative gene or the polynucleotide corresponding to the gene is differentially expressed in cancerous cells, for example, it is found that the RNA level is at least about 25%, at least about 50% to about 75%, at least about 90%, at least about 1.5 times, at least about 2 times, at least about 5 times, at least about 10 times, or at least about 50 times or more differences (e.g., higher or lower). Comparisons can be made in tissues, for example using in situ hybridization or another assay method to allow a certain degree of differentiation between the cell types in the tissue. Comparisons may also be made between cells removed from their tissue source or alternatively between an in situ cell and a second cell removed from its tissue source. In some embodiments, the oncogene gene is up-regulated compared to normal cells.

If at least one symptom or clinical end point of cancer is alleviated, terminated, slowed or prevented, FGF21-related cancers are "inhibited". As used herein, FGF21-related cancers are also "inhibited" if the metastasis or relapse of the cancer is reduced, slowed, delayed or prevented.

As used herein, the term "clinical endpoint" refers to a measurable event as a cancer indicator. The clinical endpoint includes, but is not limited to, time to first metastasis, time to secondary metastasis, size and/or amount of metastasis, tumor size and/or number, tumor location, tumor invasion, quality of life, pain and the like. The ability of a person skilled in the art to determine and measure a clinical endpoint is credible.

As used herein, the term "fragment" refers to a physically contiguous portion of the primary structure of a biomolecule. In the case of a protein, a moiety is defined by a contiguous portion of the amino acid sequence of the protein, meaning at least 3-5 amino acids, at least 8-10 amino acids, at least 11-15 amino acids, at least 17-24 amino acids, at least 25-30 amino acids, and at least 30-45 amino acids. In the case of an oligonucleotide, a moiety is defined by a contiguous portion of the nucleic acid sequence of the oligonucleotide, meaning at least 9-15 nucleotides, at least 18-30 nucleotides, at least 33-45 nucleotides acid, at least 48-72 nucleotides, at least 75-90 nucleotides, and at least 90-130 nucleotides. In some embodiments, a portion of the biomolecule is biologically active. In the context of the present invention, the FGF21 polypeptide fragment does not comprise the full FGF21 polypeptide sequence set forth in SEQ ID NO: 2.

As used herein, the term "epitope" refers to an antigenic determinant of a polypeptide. In some embodiments, an epitope may comprise 3 or more amino acids in an epitope-specific spatial conformation. In some embodiments, the epitope is a linear or conformational epitope. Typically, the epitope consists of at least 4, at least 6, at least 8, at least 10 and at least 12 such amino acids, more typically from 8 to 10 such amino acids. Methods for determining the spatial conformations of amino acids are known in the art and include, for example, x-ray crystals and 2-dimensional nuclear magnetic resonance.

The phrase "complementarity determining region" refers to an amino acid sequence that collectively determines the binding affinity and specificity of the native Fv region of the native immunoglobulin binding site. See, for example, Chothia et al., *J. Mod. Biol.* 196:901-917 (1987); Kabat et al., U.S. Dept. of Health and Human Services NIH Publication No. 91-3242 (1991). The phrase "constant region" refers to a portion of an antibody molecule that produces an effector function.

As used herein, the term "oligonucleotide" refers to a series of contiguous nucleotide residues. Oligonucleotides include, but are not limited to, antisense and siRNA oligonucleotides. An oligonucleotide comprises a partial DNA sequence and has at least about 10 nucleotides and up to about 500 nucleotides. In some embodiments, the oligonucleotide comprises from about 10 nucleotides to about 50 nucleotides, from about 15 nucleotides to about 30 nucleotides, from about 20 nucleotides to about 25 nucleotides. Oligonucleotides can be chemically synthesized and can also be used as probes. In some embodiments, the oligonucleotide is single-stranded. In some embodiments, the oligonucleotide comprises at least a portion of the double strand. In some embodiments, the oligonucleotide is an antisense oligonucleotide (ASO). In some embodiments, the oligonucleotide is a RNA interference oligonucleotide (RNAi oligonucleotide).

As used herein, the term "combination" or "joint" refers to administration of the FGF21 modulator of the present invention with other therapeutic regimens.

As used herein, the term "detect" means establishing, discovering or confirming evidences for activity (e.g., gene expression) or biomolecules (e.g., polypeptides).

As used herein, the phrase "homologous nucleotide sequence" or "homologous amino acid sequence" or variant thereof refers to a sequence characterized by at least a certain percentage of homology at the nucleotide or amino acid level, and are used interchangeably with "sequence identity". Homologous nucleotide sequences include those that encode a protein isoform. Such isoforms can be expressed in different tissues of the same organism as a result of, for example, alternative splicing of RNA. Alternatively, isoforms can be encoded by different genes. Homologous nucleotide sequences include nucleotide sequences encoding proteins of species other than humans, including, but not limited to, mammals. Homologous nucleotide sequences also include, but are not limited to, naturally occurring allelic variants and mutations of the nucleotide sequences set forth herein. In some embodiments, the homologous nucleotide sequence encodes a polypeptide having the same or similar binding characteristics and/or activity as the wild-type sequence. Homologous amino acid sequences include those amino acid sequences that contain conservative amino acid substitutions whose polypeptides have the same or similar binding characteristics and/or activity as the wild-type sequence. In some embodiments, the nucleotide or amino acid sequence is homologous if it has at least 70%, 80%, 85%, 90%, 95%, 96%, 97%, 98%, or 99% identity. In some embodiments, the nucleotide sequences or amino acid sequences are homologous if 1-10, 10-20, 20-30, 30-40, 40-50 or 50-60 nucleotides/amino acid are substituted, added or deleted. In some embodiments, the homologous amino acid sequence has no more than 5 or no more than 3 conservative amino acid substitutions.

Percent homology or identity can be determined by, for example, the Gap program (Wisconsin Sequence Analysis Software, UNIX Release 8, Genetics Computer Group, University Research Park, Madison Wis.) and using default settings, and the program uses Smith And Waterman's algorithm (Adv. Appl. Math., 1981, 2, 482-489). In some embodiments, the homology between the probe and the target is between about 75% and about 85%. In some embodiments, nucleic acids have nucleotides that are at least about 85%, about 90%, about 92%, about 94%, about 95%, about 97%, about 98%, about 99% and about 100% homologous to SEQ ID NO: 1 or a portion thereof. Complementary sequences of such sequences are also provided. In some embodiments, the complementary sequence is a complete and fully complementary sequence of the nucleotide sequence.

Homology can also be at the polypeptide level. In some embodiments, the polypeptide is at least about 85%, about 90%, about 92%, about 94%, about 95%, about 97%, about 98%, about 99%, and about 100% homologous to SEQ ID NO: 2 or a portion thereof. In some embodiments, the polypeptide has up to 5, up to 10, up to 15, up to 20, or up to 30 amino acid insertions, deletions or substitutions.

As used herein, the term "probe" refers to a variable length nucleic acid sequence. In some embodiments, the probe comprises at least about 10 and at most about 6000 nucleotides. In some embodiments, the probe comprises at least 12, at least 14, at least 16, at least 18, at least 20, at least 25, at least 50, or at least 75 contiguous nucleotides. Probes are used to detect the same, similar or complementary nucleic acid sequences. Longer probes are typically obtained from natural or recombinant sources, have a high specificity to the target sequence, and hybridize to the target much more slowly than oligomers. The probes can be single-stranded or double-stranded, and are designed to be specific in PCR, membrane-based hybridization, in situ hybridization (ISH), fluorescence in situ hybridization (FISH), or ELISA-based techniques.

As used herein, the term "binding" refers to a physical or chemical interaction between two or more biomolecules or compounds. Binding, including ionic, nonionic, hydrogen bonding, van der Waals forces, hydrophobic interactions, and the like. The binding can be direct or indirect; indirect means by or due to the influence of another biomolecule or compound. Direct binding refers to an interaction occurs without the influence by or due to another biomolecule or compound, without the need for other basic chemical agents.

As used herein, the term "sample" includes any biological sample obtained from a patient. Samples include, but are not limited to, whole blood, plasma, serum, red blood cells, white blood cells (e.g., cells from peripheral blood mononuclear cells), saliva, urine, feces (i.e., excrement), sputum, bronchial lavage fluid, tears, nipple aspirate, lymphatic (e.g., diffuse tumor cells of lymph nodes), fine needle aspirates, any other body fluids, tissue samples (e.g., tumor tissue), such as tumor biopsies (e.g., needle aspiration biopsies) and their cell extracts. In some embodiments, the sample is whole blood or a component thereof, such as plasma, serum, or cell pellet. In a preferred embodiment, the sample is obtained from circulating cells of a whole blood molecule solid tumor or a cellular component thereof using any technique known in the art. In other embodiments, the sample is a tumor tissue sample of formalin fixed paraffin embedded (FFPE), such as a solid tumor from the lung, colon or rectum.

"Biopsy" refers to the process of taking out tissue samples for diagnostic or prognostic evaluation, also referring to tissue samples themselves. Any biopsy technique known in the art can be applied to the methods and compositions of the present invention. The biopsy technique applied will generally depend on the type of tissue to be evaluated and the tumor size and type (i.e., solid or suspended (i.e., blood or ascites)) and the like. Representative biopsy techniques include excision biopsy, incision biopsy, needle aspiration biopsy (e.g., core needle biopsy, fine needle aspiration biopsy, etc.), surgical biopsy, and bone marrow biopsy. Biopsy techniques are described, for example, in *Harrison's Principles of Internal Medicine*, Kasper et al., Eds. 16, 2005, Chapter 70, and the whole Part V.

Each of the patents, patent applications, accession numbers and publications described herein are hereby incorporated by reference in their entirety.

In addition to the herein described, various modifications of the present invention will be apparent to those skilled in the art from the foregoing description. Such modifications are also intended to fall within the scope of the appended embodiments. The following examples are presented for the purpose of illustration, and are not intended to limit the scope of the present invention.

EXAMPLES

Materials, Reagents (Manufacturers) and Equipment Models and Manufacturers

The following materials, reagents will be used in the examples, both of which are commercially available and are specifically disclosed as follows:

I.1 pcDNA3.0-hSCN3B, commercially available from Origene Corporation (OriGene Technologies, 9620 Medical Center Dr., Suite 200, Rockville, Md. 20850•1.888.267.4436)

I.2 Cell lines: Hep3B, HepG2, HL7702, purchased from Institute of Biochemistry and Cell Biology, Shanghai Institutes for Biological Sciences, Chinese Academy of Sciences I.3 Interference RNA sequence, designed and provided by Shanghai Genepharma Co., Ltd.

```
SCN3B-homo-409
                                  (SEQ ID NO: 3)
5'-CCUGCCUUCAAUAGAUUCUTT-3'

(SEQ ID NO: 4)
5'-ACAAUCUAUUGAAGGCAGGTT-3';
or

SCN3B-homo-608
                                  (SEQ ID NO: 5)
5'-GCGGUAAAGAUUUCCUUAUTT-3

(SEQ ID NO: 6)
5'-AUAAGGAAAUCUUUACCGCTT-3'.
```

I.4 Negative sequence, designed and provided by Shanghai Genepharma Co., Ltd.

```
Sense
                                  (SEQ ID NO: 7)
5'-UUCUCCGAACGUGUCACGUTT-3

Antisense
                                  (SEQ ID NO: 8)
5'-ACGUGACACGUUCGGAGGATT-3'
```

I.5 β3-specific primers synthesized by the Kingsway Technology Inc., the sequence is as follows:

```
β3: F:
                                  (SEQ ID NO: 9)
5'-CGTCTACCGCCTGCTCTTCT-3'

R:
                                  (SEQ ID NO: 10)
5'-GGTATTCCGAGGCATTCTCCT-3'
```

I.6 Analgesic-antitumor peptide, AGAP:

The gene of GENBANK Gene No. AF464898 was cloned into *E. coli* expression vector and transformed into *E. coli* cells to construct recombinant bacteria. The active peptide was expressed in *E. coli* and purified by chromatography to obtain recombinant analgesic antineoplastic peptide.

I.7 GIBCO RPMI1640 medium (Cat. No. LM-R1645), newborn bovine serum (Cat #16010-159), fetal calf serum (Cat. No. 10099-141), purchased from Life Technologies, (Life Sciences Solutions Group, Thermo Fisher Scientific, Carlsbad, Calif.)

I.8 BIOZOL RNA Extraction Kit purchased from BioFlux (Cat #: R1020-01)(BIOFLUX SRL Address: 54 Ceahlau street, Cluj-Napoca 400488, Romania, European Union, Europe)

I.9 Protein extraction kit (KGP2100), reverse transcription kit (Cat #: KGEA-01), Purchased from Keygen Biotech (Nanjing Keygen Biotechnology Development Co., Ltd., Zijing Fangshan Venture Community Building 6, No. 18 Zilan Road, Jiangning District, Nanjing)

I.10 β3 Specific antibodies purchased from abeam (Cat #: ab48552)

I.11 Invitrogen Lipofectamine 2000 transfection kit purchased from Life Technologies (Cat #: 11668019) (Life Sciences Solutions Group, Thermo Fisher Scientific, Carlsbad, Calif.)

I.12 Transwell chambers purchased from Corning Corporation (CORNING, Corning Incorporated, One Riverfront Plaza Corning, N.Y. 14831 USA), I.13 Matrigel purchased from BD (BD Biosciences)

I.14 Instrument: Thermo carbon dioxide incubator (Type 311), Beijing Liuyi Instrument Factory, DYY-8C electrophoresis, Beijing Liuyi Instrument Factory, DYCZ-40D transfer membrane slot

Example 1: Expression of β3 Subunit in Tumor Cells 1.1 Expression of β3 Subunit in Hepatocellular Carcinoma Cell Lines Total mRNA was extracted from different cell lines (HepG2, HL7702), 10 μg of mRNA was reverse transcribed, and 2 μL of cDNA was used as a template to specifically amplify mRNA transcribed from β3 gene (PCR conditions and primers used: Candenas L, Seda M, Noheda P, Buschmann H, Cintado C G, Martin J D, et al. Molecular diversity of voltage-gated sodium channels alpha and beta subunit mRNAs in human tissues. Eur J Pharmacal. 2006; 542: 9-16.), assayed by agarose gel electrophoresis, and the mRNA level in each cell line was detected The total protein of different cell lines was extracted and the protein content was determined by Bradford method. 20-70 μg protein was taked for electrophoresis. After electrophoresis, Western blotting was performed to examine the expression of the β3 subunit gene at protein level. Specifically, the Bradford method was as follows:

1. About 10 mg bovine serum albumin was precisely weighted, put into a 10 ml volumetric flask, dissolved in distilled water and diluted to the scale, shook, to obtain the working fluid. 10 μl, 20 μl, 30 μl, 40 μl, 50 μl and 100 μl of standard protein solution (bovine serum albumin, 1.0 mg/ml) were added to the labeled test tubes, respectively, those less than 100 μl were supplemented with physiological saline to 100 μl. 5 ml Coomassie brilliant blue G-250 solution (50 mg of Coomassie Brilliant Blue G-250 was weighted and dissolved in 25 ml of 95% ethanol, 50 ml of 85% phosphoric acid was added, and finally distilled water was added to dilute to 500 ml, filtered through a filter paper) was added, and normal saline was used as blank control;

2. The microplate was placed on a shaker and shaken for 30 sec, left for 2 min and then shaken again. The colorimetric assay was performed at 595 nm (colorimetric should be done within 1 h). The standard curve is drawn with concentration of protein (mg/ml) for the abscissa, absorbance for the ordinate;

3. The sample to be test was diluted to appropriate concentration, so that the total volume of the sample diluent was 100 μl, 100 μl Coomassie brilliant blue G-250 solution was added, well mixed, then placed still for 2 min, the standard curve 0 tube as reference, measured at 595 nm wavelength, recorded absorbance values;

4. According to the measured sample absorbance, the corresponding protein concentration can be found on the standard curve, multiplied by the sample dilution factor to obtain the actual concentration of the sample.

Western Blot steps as follows:

1. Sample treatment: the loading buffer and the sample to be measured were loaded at the same volume, vortex mixed, and heated in a boiling water bath for 5 min, then centrifuged;

2. Electrophoresis (1) the glass plate is installed according to the manufacturer's instructions;

(2) The required concentrations of the separating gel solution were prepared according to the values given in Table 1;

(3) Acrylamide solution was quickly poured into the gap between the two glass plates, leaving the space required for perfusion of concentrated plastic (comb tooth length plus 1 cm). After the gel was completely polymerized, the overlay liquid was decanted and the top of the gel was washed several times with deionized water to remove the unpolymerized acrylamide. The liquid on the gel was drained as far as possible, and edge of paper towels were used to completely absorb residual liquid;

(4) The concentrated gel solution was prepared according to the values given in Table 1;

(5) The concentrated gel was directly poured onto the polymerized separation gel and a clean Teflon comb was then inserted into the concentrate gel solution. Care was taken to avoid entering of the bubbles and the gel was placed vertically at room temperature to polymerize;

(6) When the concentrated gel was polymerizing, the samples which had already been concentrated were mixed with 2×loading buffer, heated at 100° C. for 5 min to denature the proteins. Samples with diluted concentrations need to be enriched with trichloroacetic acid, and then were precipitated with acetone;

(7) After the polymerisation of the concentrated gel was complete, the Teflon comb was carefully removed and the sample loading slots were immediately washed with an electrophoresis upper slot buffer to remove the unpolymerized acrylamide. The gel was fixed on an electrophoresis apparatus, and an electrophoresis buffer was added thereto. The air bubbles between the two glass plates at the bottom of the gel were removed;

(8) Samples were added to the bottom of the sample well in a predetermined order, and the sample injector should be washed clean with each sample added. Finally, an equal volume of gel loading buffer was added to all unused sample wells;

(9) Electrophoresis device was connected to the power (anode should be connected to the lower slot), electrophoresis were performed until bromophenol blue reached the bottom of the separation gel, and then the power is turned off;

(10) The glass plates were removed from the electrophoresis unit, placed on a paper towel and levered with a spatula.

TABLE 1

Compositions of separating gel and concentration gel

|  | Sealing gel | 12.5% Seperation gel | Concentration gel |
|---|---|---|---|
| Water (ml) | — | 3.96 | 3.15 |
| Acrylamide 30% (ml) | 1.0 | 4.8 | 0.75 |
| 1.5M Tris pH 6.8 (ml) | — | 3.0 | — |
| 1.0M Tris pH 8.8 (ml) | 1.0 | — | 0.57 |
| 10% APS (μl) | 70 | 120 | 120 |
| 10% SDS (μl) | — | 120 | 45 |
| TEMED (μl) | 8 | 12 | |

3. Cut gel, transfer to film (1) After electrophoresis is finished, the glass plates were quickly pried open with a rubber plate, be careful to maintain the formation of gel. The desired bands were cut according to the pre-stained Marker, with the cutting range slightly wider than the target proteins; a corner of the gel is cut and marked; and measured the length;

(2) The gel was immersed in a previously prepared transfer membrane buffer (proteins with a smaller molecular weight were required to shorten the soaking time in the transfer membrane buffer, and the proteins with larger molecular weights were required to extend the soaking time in the transfer membrane to facilitate transfer);

(3) PVDF membranes were cut and labeled on the corners, infiltrated with methanol for 5 min, placed in equilibration with ddH$_2$O for 5 min, and immersed in transfer membrane buffer;

(4) The transfer device "sandwich structure" was installed from bottom to top:sponge→filter paper→film→gel→filter paper—sponge (each layer to ensure no bubbles, filter paper was pressed with a clean dropper or test tube, film and gel layer were placed with caution to avoid the generation of bubbles);

(5) 2 times of the size of the gel was set as the current for transferring film, the transfer membrane time was set according to the molecular weight of the protein, the membrane was cross-flow transferred for 1 h 40 min.

4. Immune response (1) After the membrane was transferred, the membrane was removed, the membrane size was cut according to the location of the band, and the surface of the protein was marked;

(2) With 5% skim milk powder as a blocking solution, being blocked on a shaker at room temperature for 3 h;

(3) The primary antibody was prepared, and diluted with milk blocking solution, and the surface with the target protein was placed face down onto the primary antibody dilution, then incubated at 4° C. overnight;

(4) The primary antibody was discarded, the membrane was washed with TBST, placed on the shaker for washing the membrane three times, each 15 min;

(5) Secondary antibody incubation is same as the primary antibody, incubated at room temperature for 2 h;

(6) The secondary antibody was discarded, the membrane was washed with TBST, placed on the shaker for washing three times, each 15 min 5. Development (1) ECL illumination solution was mixed at a ratio of A:B=1:1, used in a ratio recommended in the protocol;

(2) The illumination solution was evenly dropped on the film;

(3) The film was removed in the dark room, placed in the cassette, exposed for 20 min, and removed;

(4) The film was soaked in the developer for 2 min, washed with water for 2 min, immersed in the fixing solution for 2 min, washed with water for 2 min, and the results were observed.

Figure 1:
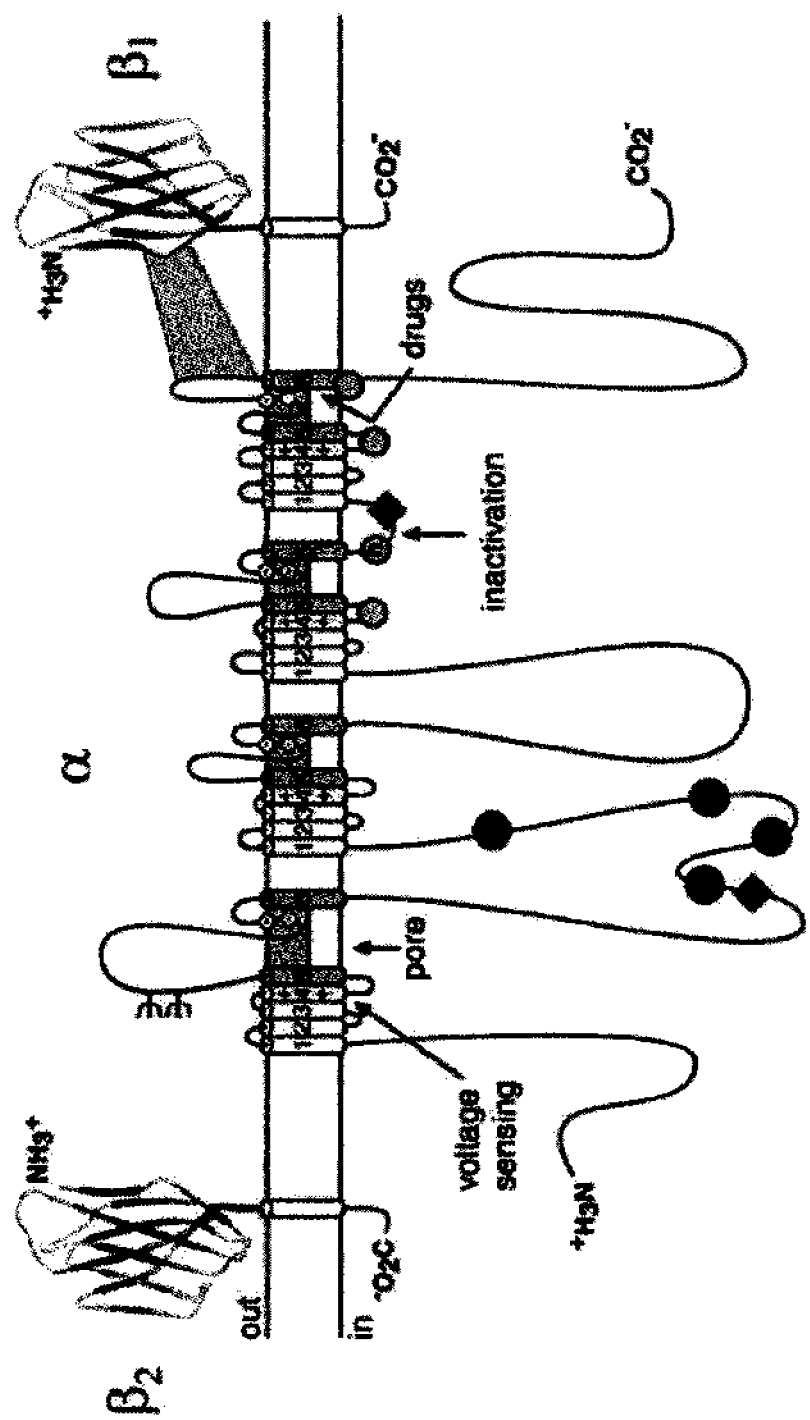
FIG. 1: Structure of voltage-gated sodium channel (ROGER S, POTIER M, VANDIER C, et al., Voltage-Gated Sodium Channels: New Targets in Cancer Therapy [J]. Curr Pharm Des, 2006, 12 (28) 3681-3695)
Figure 2:
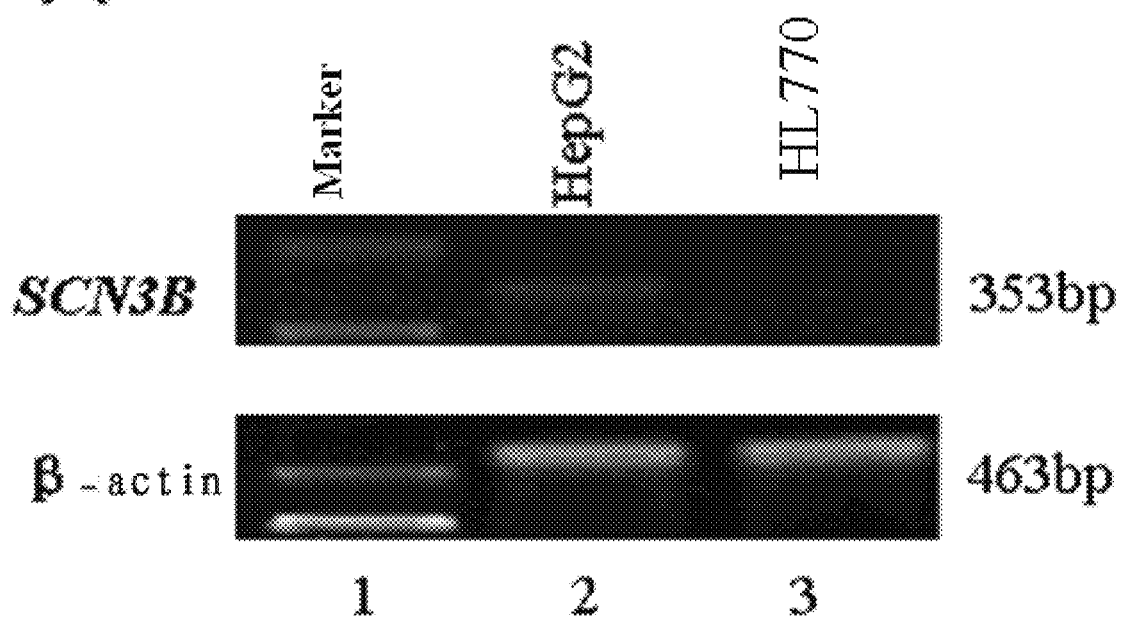
FIG. 2: Expression of β3 in different liver cancer cell lines.
Figure 2:
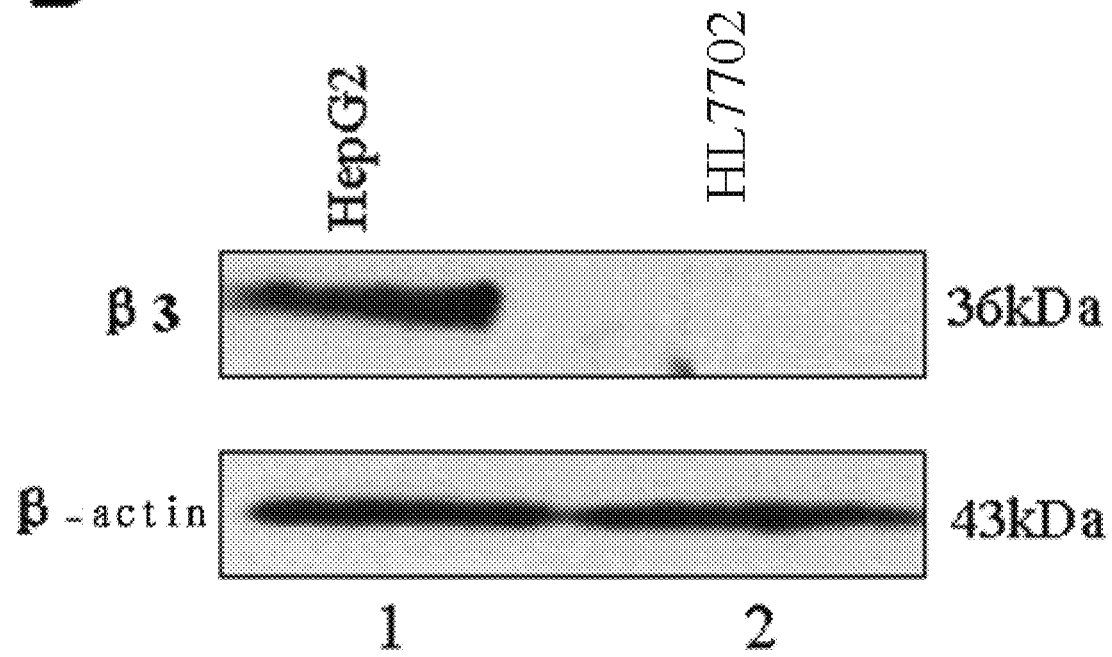

The results showed that VGSCβ3 subunit (SCN3B) RNA (FIG. 2A) and the expression of protein (FIG. 2B) were detected in hepatoma cell line HepG2, while in normal HL7702 cells, the mRNA and protein of VGSC β3 subunit were absent. The results showed that the expression of VGSCβ3 subunit was high in HepG.

1.2 the Different Expressions of β3 Subunit in Different Leukemia Cells

Figure 3:
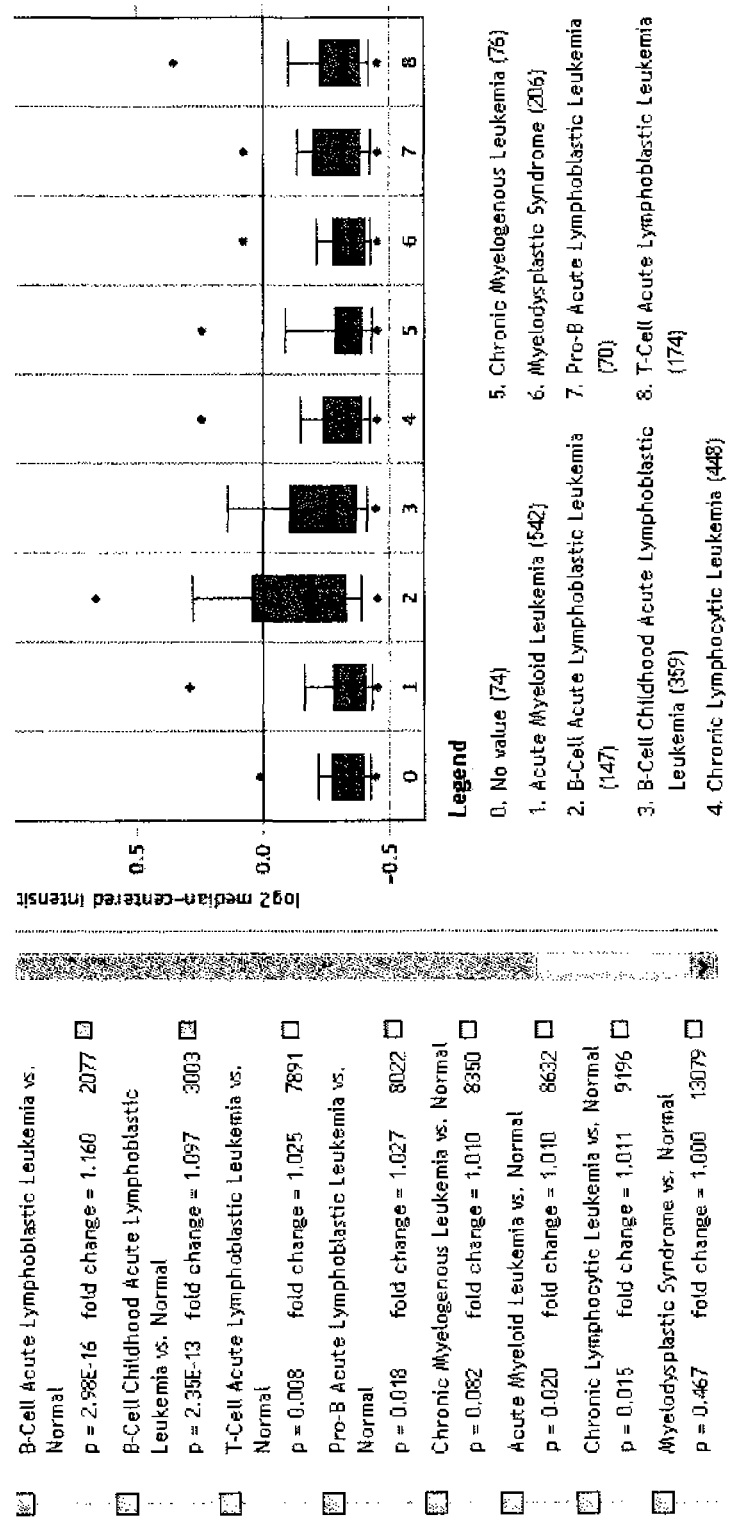
FIG. 3: SCN3B, a gene encoding the VGSC β3 subunit, is expressed in different leukemias.

SCN3B expression was detected in different types of leukemia cell lines and normal cells in the ONCOMINE database (www.oncomine.com). Data analysis of the microarray data (www.oncomine.org) revealed that abnormal SCN3B mRNA expression in VGSC were also present in leukemia. In the Database Screening option, the gene was SCN3B, and the target was leukemia vs. normal tissue. SCN3B codes voltage-gated sodium channel subunit β3, and the following picture shows the expression of SCN3B in different types of leukemia. The results showed, except that in the sixth group of myelodysplastic syndrome (Myelodysplastic Syndrome) the SCN3B expression had no significant difference with that in normal cells, the other seven different types of leukemia, Acute Myeloid Leukemia, B-cell Acute lymphoblastic Leukemia, B-Cell Childhood Acute Lymphoblastic Leukemia, Chronic Lymphocytic Leukemia, Chronic Myelogenous Leukemia, Pro-B Acute Lymphoblastic Leukemia, T-Cell Acute Lymphoblastic Leukemia all showed high levels of SCN3B expression (P<0.05), and the expression levels of SCN3B were different in different types of leukemia (FIG. 3).

Example 2. Down-Regulation of Expression of β3 Subunit Affected Tumor Cell Proliferation 2.1 Down-Regulation of β3 Subunit Expression Influenced the Proliferation of Liver Cancer Cells Using two pairs of β3-specific small interfering RNAs in I.3, and using the method of RNAi, the expression of β3 subunit of hepatoma cell line HepG2 was interfered, and the expression of β3 subunit was down-regulated and the hepatoma cell proliferation was inhibited.

2.1.1 RNAi Interference of β3 Gene Expression

Cells were inoculated one day before the interference experiment, the cells should reach 30% to 50% coverage at the day of interference. Interference experiments were performed according to Lipofectamine 2000 instructions, two pairs of β3-specific small interfering RNAs of the preceding I.3 were transfected into cells at the same concentration (50 nM) to interfere with expression of VGSC β3, using the same amount of negative sequence in random sequence I.4 as control. On the day of transfection, lipofectamine 2000 and plasmid siRNA (25-50 nM) were diluted with serum-free medium, mixed, incubated at room temperature for 5 min. The aforesaid mixture was directly added to the medium, mixed with gently shaking, and cultured cells at conventional conditions for 4-6 h, replaced with fresh medium and continued to culture for 2-3 days, then performed experiment.

2.1.2 the Protein Level of Hep G2 Cell Line was Down-Regulated after the Interference with β Subunit Using the method described in Example 1, the cell total protein obtained in 2.1.1 was extracted and the protein content was determined. The loading buffer and the protein to be measured (20 to 70 μg protein) were loaded with the same volume, vortex mixed, boiling water bath for 5 min, and then centrifuged. After electrophoresis, the gel was transferred to PVDF membrane and subjected to western blotting analysis using the VGSC β3 specific antibody obtained from abeam Company.

Figure 4:
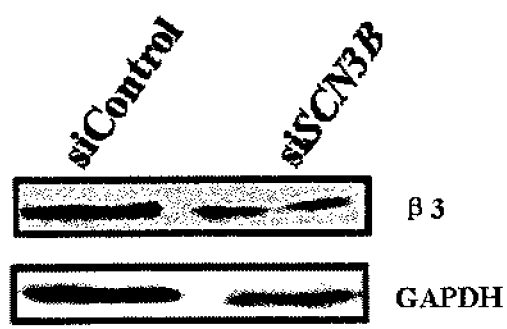
FIG. 4: Western blotting detection of post-interference protein level β3 gene expression.
Figure 4:
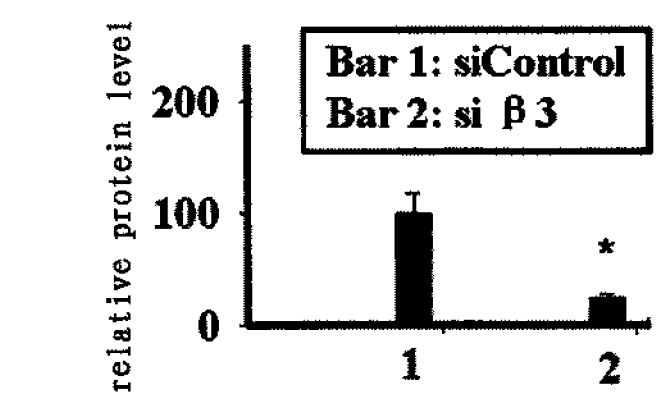

Western blotting results showed that the two pairs of siRNAs in I.3 inhibited the expression of VGSC β3 in HepG2 cells. In other words, siRNA in I.3 effectively inhibited the level of β3 subunit protein (FIG. 4).

2.1.3 Inhibition of β3 Gene can Reduce the Proliferation of HepG2 Cells

The cell proliferation was measured by MTT assay: took the cells in good growth condition and in logarithmic growth phase, digested with conventional trypsin, and pipetted into a single cell suspension, after counting the blood cell with blood counting chamber, the concentration was adjusted to $10^5$ cells/ml (HepG2 cells), then were inoculated into 96-well plates at 100 μl per well, while set the blank hole (only added 100 μl of culture medium, without cells); cultured in 5% $CO_2$ incubator at 37° C. for 24 h, each well was added 0.5 mg/ml MTT, 100 μl, then continued to culture for 4 h, the supernatant was discarded and 150 μl of DMSO was added to each well. The mixture was incubated at low speed for 10 min on a micro shaker, and the absorbance of each well was measured at 490 nm using a microplate reader after the crystals were fully dissolved.

Significance analysis was performed according to the test results, and the inhibition rate was calculated according to the following formula.

Inhibition rate (%)=(control group−loading group)/
(control group−blank well)×100

Figure 5:
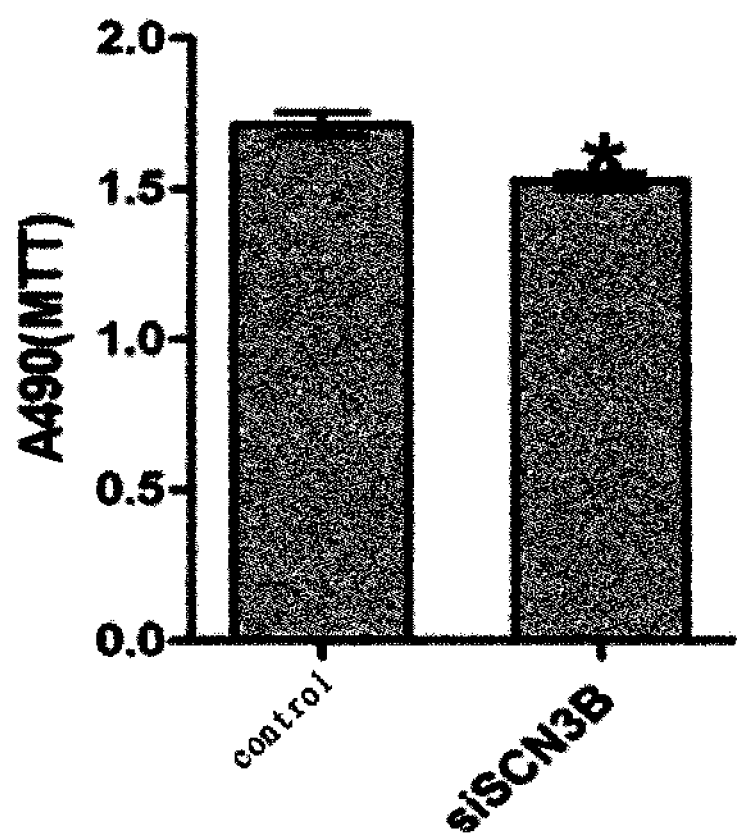
FIG. 5: MTT assay of the effect of VGSC β3 RNAi interference on the proliferation of Hep G2 cells.

Cell proliferation changes were measured by MTT assay, after the expression of the VGSC β subunit of HepG2 cell line was interfered by siRNA as shown in section 2.1.2. The results showed that the proliferation of HepG2 cells was significantly decreased after interfering with β3 subunit (P<0.05) (FIG. 5).

From the above results, it can be seen that the level of HepG2 cells can be reduced by inhibiting the protein level of VGSC β3 in HepG2 cells.

2.1.4 Blocking HepG2 Cell Cycle by Interfering with VGSC β3 Gene

HepG2 cells were subjected to PI staining after interference in 2.1.2: after the cells were processed, the cells were collected by centrifugation after digestion (0.25% trypsin digestion solution, 2 mL, digestion 1-2 minutes), supernatant was discarded, PBS (KCl 0.2 g/L, $KH_2PO_4$ 0.2 g/L, NaCl 8 g/L, $Na_2HPO_4.12H_2O$ 2.9 g/L), after resuspension, centrifugation was performed once (1000 rpm, centrifuged for 5 minutes);

After resuspension of PBS, the cell concentration was adjusted to $10^6$ cells/ml, centrifuged again (1000 rpm, centrifuged for 5 minutes), fixed with 70% ethanol pre-cooled at −20° C., fixed overnight at −20° C.;

After the fixation, ethanol was removed by centrifugation and washed once with PBS.

the centrifuged cells were resuspended with PI staining solution ($10^6$/500 μL) at room temperature for 15-30 min, filtered with 200 mesh sieve to prepare single cell suspension, and detected with flow cytometry: the excitation wavelength was 488 nm and the emission wavelength was 615 nm.

Figure 6:
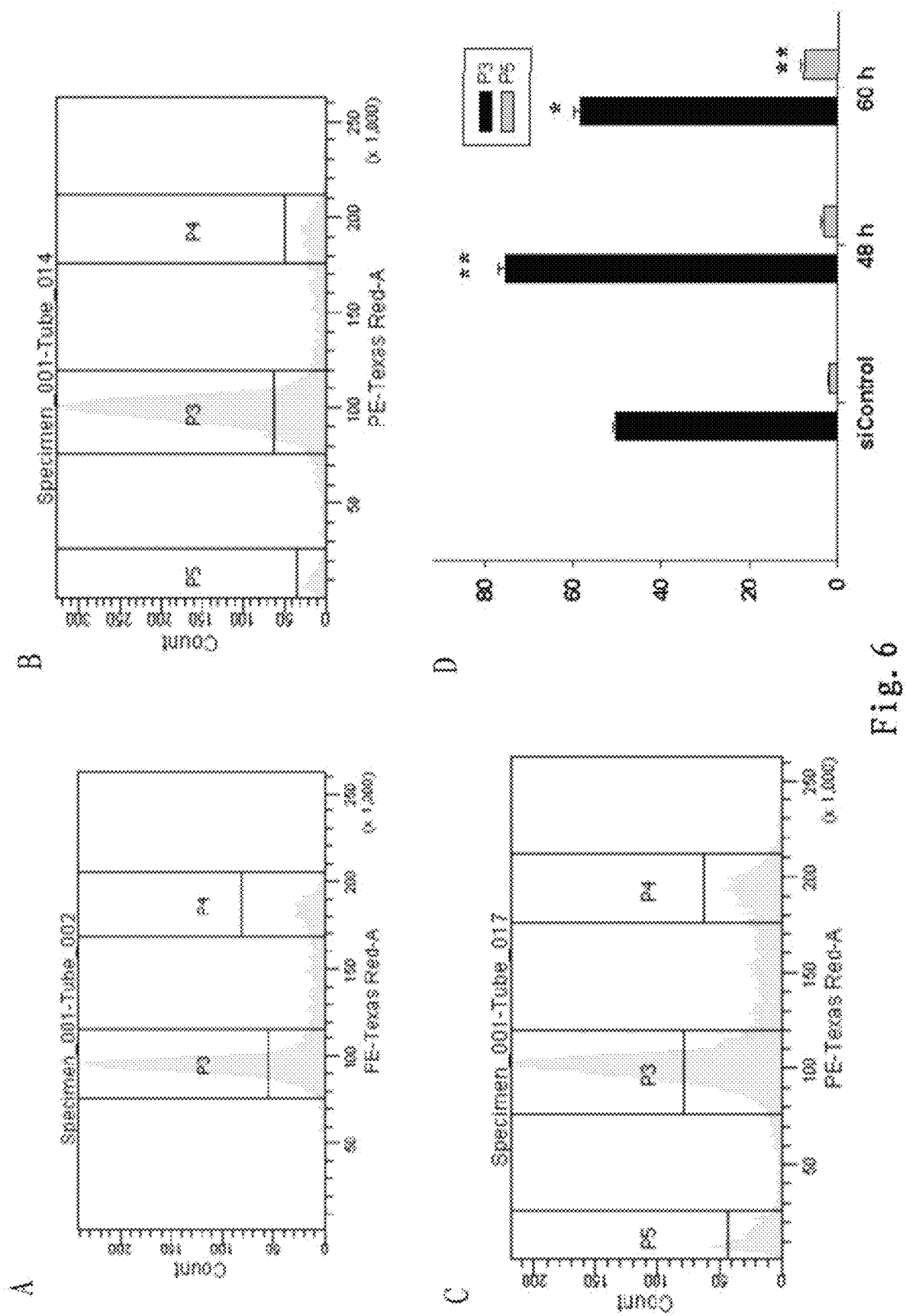
FIG. 6: Effect of interference with VGSC β3 subunit on cell cycle: A: Cell flow cytometry results of blank HepG2 cells; B: Flow cytometry results of HepG2 cells which were interfered with SCN3B for 48 h; C: Flow cytometry results of HepG2 cells which were interfered with SCN3B for 60 h; D: Figs. A, B, C, statistical results of integration of p3 peak and p5 peak area, representing cell numbers, wherein p3 is the G0/G1 phase, p5 is the fragment peak (apoptotic peak)

The cells were counted by flow cytometry, the results showed that the cell cycle was blocked at G0/G1 phase ( P<0.01) 48 hours after the interference (FIG. 6**). It can be seen that the cell cycle of HepG2 can be blocked by interfering with VGSC β3 gene.

Figure 7:
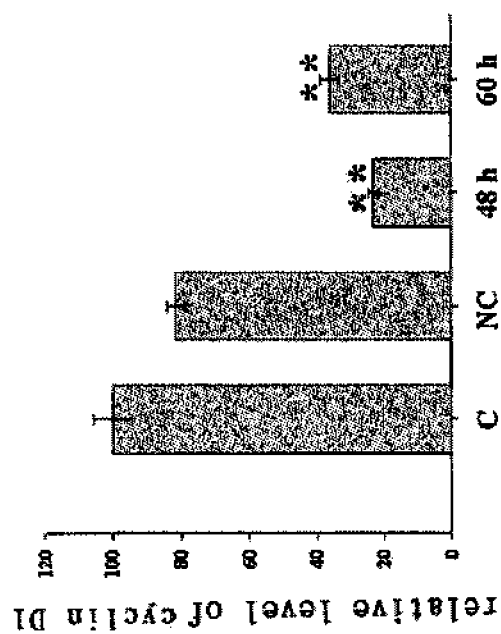
FIG. 7: After VGSC β3 subunit gene was interfered, HepG2 cyclin D1 expression level was down regulated.
Figure 7:
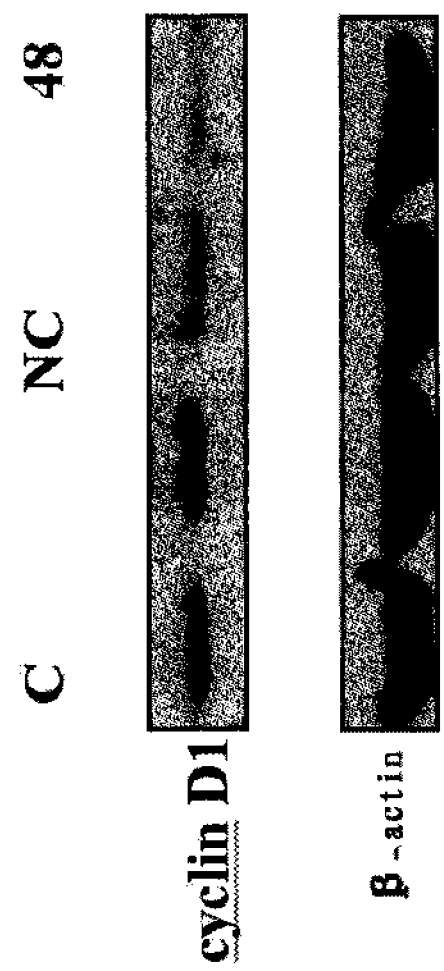

2.1.5 the Expression of Cyclin D1 in HepG2 Cells was Down-Regulated by Interfering with VGSC β3 Gene Using the method described in Example 1, the total cellular protein of the HepG2 cells after interference in 2.1.2 was extracted and the protein content was measured, 20 to 70 μg protein was taken as protein to be measured, and the loading buffer and the protein to be measured were loaded with the same volume, vortex mixed, boiling water bathed for 5 min, and then centrifuged. After electrophoresis, the gel was cut and transferred to PVDF membrane and analyzed by Western blotting with specific antibody. The results showed that the expression of cyclin D1 (SANTA CRUZ; sc753) was down-regulated (FIG. 7).

2.2 the Proliferation of Lung Cancer Cells were Affected by Downregulation of VGSC β3 Subunit Expression.

Using two pairs of β3-specific small interfering RNAs in I.3, and using the method of RNAi, the expression of β3 subunit of lung cancer cell lines was interfered, and the expression of β3 subunit was down-regulated and the lung cancer cell proliferation was inhibited.

2.2.1 β3 Gene Expression was Interfered with RNAi

Cells were inoculated one day before the interference experiment, the cells should reach 30% to 50% coverage at the day of interference. Interference experiments were performed according to Lipofectamine 2000 instructions, the expression of VGSC β3 was interfered by using two pairs of β3-specific small interfering RNAs described in I.3, random sequence the negative sequence in I.4 as control (same method as 2.1.1)

2.2.2 the Protein Level of Lung Cancer Cell Line was Down-Regulated after the Interference with β3 Subunit Using the method described in Example 1, the cell total protein obtained in 2.2.1 was extracted and the protein content was determined. The loading buffer and the protein to be measured (20 to 70 μg protein) were loaded with the same volume, vortex mixed, boiling water bathed for 5 min, and then centrifuged. After electrophoresis, the gel was cut and transferred to PVDF membrane and subjected to western blotting analysis using the VGSC ββ3 specific antibody in I.10.

Figure 8:
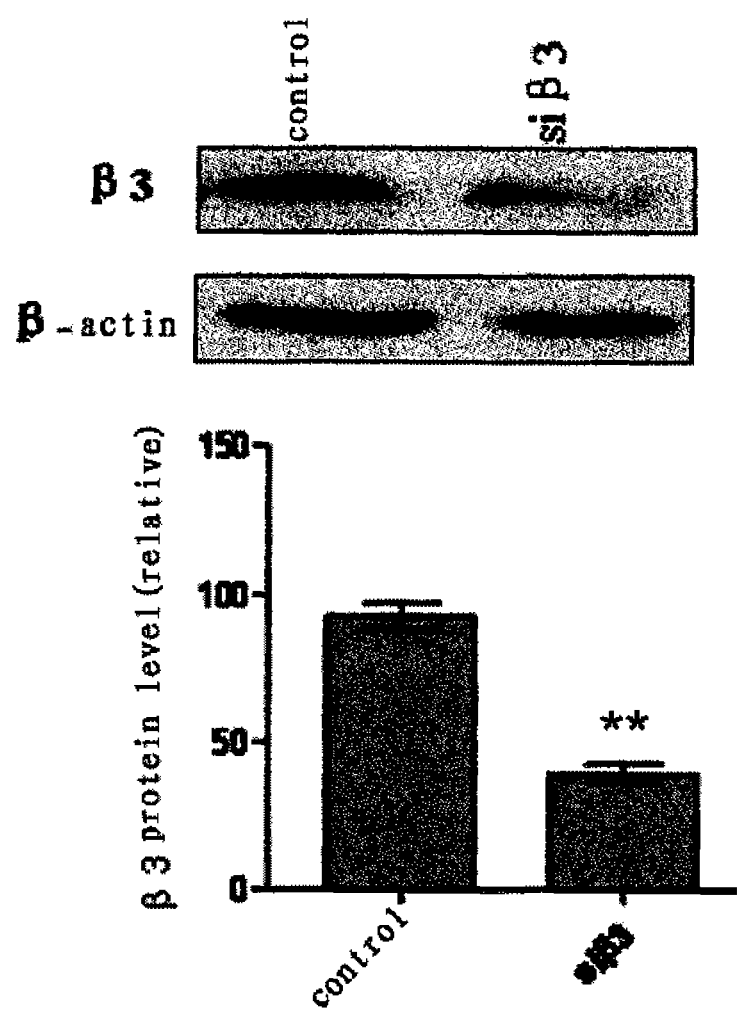
FIG. 8: Protein expression after the VGSC β3 subunit gene in lung cancer cell line A549 being interfered.

Western blotting results showed that the two pairs of siRNAs in I.3 inhibited the level of VGSC β3 subunit protein in lung cancer cell A549 (FIG. 8).

2.2.3 After β3 Gene Interference, the Proliferation of Lung Cancer Cells Decreased Cell proliferation was measured using the MTT assay (described in 2.1.3), Significant analysis was performed according to the test results, and the inhibition rate was calculated according to the following formula.

Inhibition rate (%)=(control group−loading group)/
(control group−blank well)×100

Cell proliferation changes were measured by MTT assay, after the expression of the VGSC β subunit of B5492 cell line was interfered by siRNA as shown in section 2.2.2. Cell proliferation inhibition rate was 50%, when the two siRNAs were transfected at a concentration of 50 nM, respectively (the same method as 2.1.1)

Example 3 Active Peptide AGAP Inhibits Hepatoma Cells by Inhibiting Protein Expression of VGSC β3

3.1 Active Peptides Down-Regulated the Expression of VGSC β3 Subunit, and Inhibited the Proliferation of Hepatoma Cells Analgesic antitumoral peptide (AGAP) at eight different concentrations (0, 5, 10, 15, 20, 25, 30, 35 and 40 μM) were incubated with hepatoma cell lines HepG$_2$ (96 well plates, 10$^4$ cells/well, 24 h later, AGAP was administered at different concentrations as described above, at least 3 wells were repeated for each concentration) for 48 h, the amount of the VGSC β3 subunit expressed was then detected by Western blotting using the antibody in I.10. The cell proliferation level was measured using the MTT method.

Figure 9:
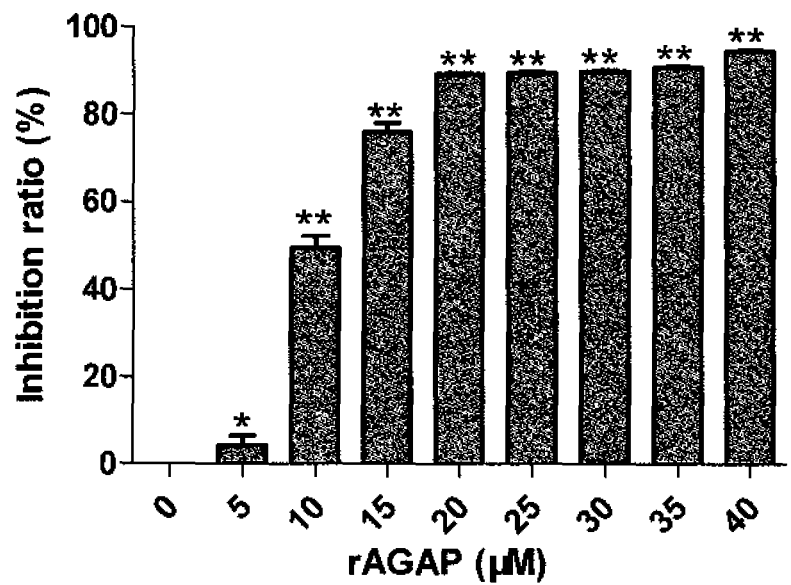
FIG. 9: Effects of AGAP on Hep G2 cell proliferation and expression of VGSC β3 subunit:
A: Inhibitory effect of AGAP on Hep G2 cell proliferation;
B: Inhibitory effect of AGAP on VGSCβ3 subunit expression in Hep G2 cells.
Figure 9:
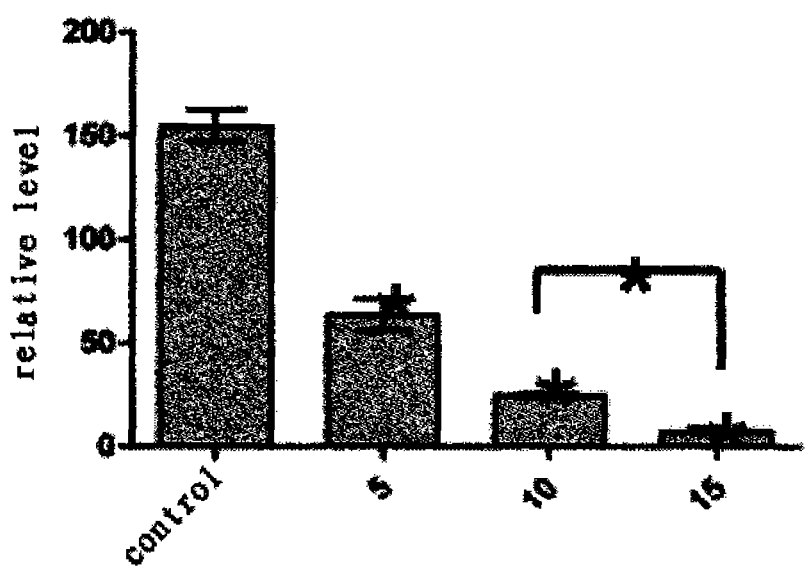

The results showed that the expression of VGSC β3 was decreased when dose increased, in dose-dependent manner after administration of AGAP to HepG2 cells (FIG. 9B), meanwhile, AGAP inhibited the proliferation of tumor cells in a dose-dependent manner, with an IC50 of 10 μM (FIG. 9A). In contrast, bovine serum albumin and cytochrome C (40 μM, 48 h incubation, other conditions were the same as administration AGAP) as controls had no effect on the expression of the VGSC β3 subunit nor did it affect cell proliferation.

It can be seen that active AGAP inhibits cell proliferation by inhibiting the expression of the VGSC β3 subunit.

Figure 10:
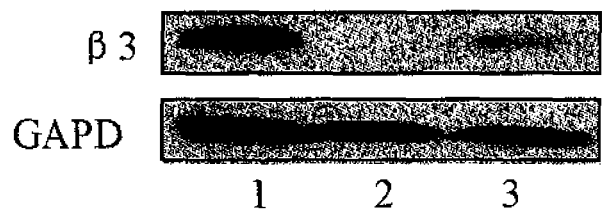
FIG. 10: The expression of VGSCβ3 subunit protein in Hep3B cells after transfection and the expression of VGSCβ3 subunit protein after AGAP administration: Lane 1: transfected with pcDNA3.0-hSCN3B; Lane 2: transfected with empty plasmid pcDNA3.0; Lane 3: effect of administration of AGAP to Hep3B cells transfected with VGSC β3 on the expression of VGSC β3; GAPDH used as an internal control.

3.2 Active Peptide AGAP Reversed Proliferation of Hep3B Cells Due to Up-Regulation of Expression of VGSC β3 Subunit The VGSC β3 gene was transfected into a Hep3B cell line that did not express the VGSC β3 gene using the plasmid transfection shown in FIG. 14 (wherein the gene SCN3B encoding VGSC β3 is set forth as SEQ ID NO: 2, the plasmid construction flow is shown in FIG. 15, PcDNA3.0 plasmids were purchased from Beijing Origene Company (ORIGENE, Address: 9620 Medical Center Dr., Suite 200 Rockville, Md. 20850)) using the following cell transfection experiments. The western blotting results showed that the β3 subunit was expressed at the protein level (FIG. 10).

Cell Transfection Experiments:

1. Using lipofectamine 2000 transfection method, one day before transfection, cells were digested with trypsin and counted, cells were plated, the cells were inoculated into a 6-well culture plate at a suitable cell density of 6×10$^5$ cells/well so as to achieve a confluency of 80% to 90% at the time of transfection.

2. Preparation of transfection solution: the following two solutions were prepared in the EP tube (the amount used to transfect one well).

Solution A: dilute the DNA with serum-free and antibiotic media RPMI1640 to a concentration of 4 μg and a final volume of 500 μl. The plasmid DNA contained the plasmid containing the desired gene, and the empty plasmid pcDNA3.0 plasmid was used as a negative control.

Solution B: Lipofectamine 2000 8 μl was diluted with serum and antibiotic-free medium to a final volume was 500 μl, and allowed to stand at room temperature for 5 min. The ratio of plasmid to Lipo transfection reagent was 1:2.

3. Gently mixed with solution A, B, and allowed to stand at room temperature for 20 min, later cloudy phenomenon appeared, but did not affect the transfection.

4. During this period, cells in 6-well plates were washed twice with serum-free medium and then 1 ml of serum-free RPMI1640 medium without antibiotics was added.

5. The mixture of solution A and solution B was added dropwise to the wells and the plates were shaken and gently mixed, and incubated in a 5% CO$_2$ incubator at 37° C. for 6 hours.

6. After 6 hours, the complete medium containing serum and antibiotics were replaced, and continued the culture in a 5% CO$_2$ incubator at 37° C., and the protein level was detected after 48-72 h.

After transfected with VGSC β3 subunit gene, Hep3B expressed VGSC β3 (The protein expression after transfection is shown in FIG. 10, lane 1), the effect on cell proliferation was determined by MTT assay as described above. From the results in FIG. 11, column 2, it is known that after transfection of β3 subunit, Hep3B cells promoted cell proliferation (**P<0.01). It can be seen that the VGSC β3 subunit can promote the proliferation of cancer cells.

Figure 11:
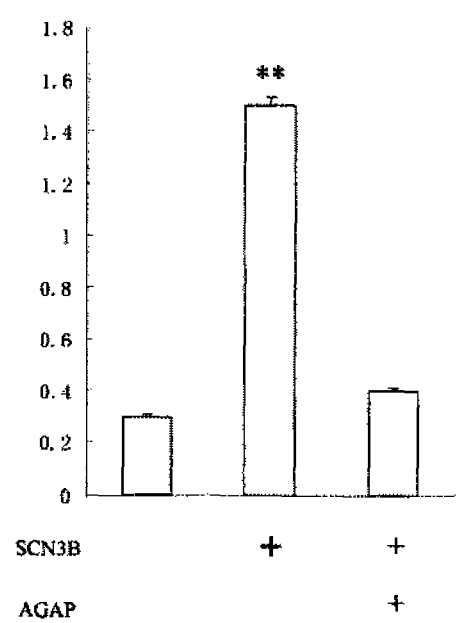
FIG. 11: Detection of cell proliferation after transfection of VGAC beta3 subunit in Hep3B cells and detection of cell proliferation after AGAP administration.

After Hep3B was transfected with β3 subunit gene, active peptide AGAP (10 μM) was added, Western blotting showed down-regulation of the VGSC β3 subunit (FIG. 10, lane 3). The effect on cell proliferation was determined by MTT assay as described above, AGAP significantly inhibited cell proliferation after transfection (FIG. 11, column 3).

Example 5 siRNA of the Present Invention Inhibited Tumor Growth in Nude Mice

HepG2 was transfected with the two pairs of β3 siRNA described in I.3 and the control siRNA described in I.4, cells were collected after 24 h (same method as 2.1.1). Twelve nude mice were chosen and randomly divided into HIF-1a siRNA experimental group and control group, subcutaneous injected with respective HepG2 cells on the back (5×10$^6$/mouse). Tumor size was measured daily and tumor volume was calculated until animals were sacrificed at the 21$^{st}$ day. Tumor volume=(major tumor diameter×(minor tumor diameter) 2)/2.

The tumor subcutaneously grown from the siRNA transfected HepG2 hepatoma cells in nude mice grew slowly. From the first 6-7 days, tumor nodules were appeared at the subcutaneous site where the tumor cells were inoculated in both the experimental group and the control group of nude mice, but the two groups have no difference (t=690, P=0.064>0.05). Starting from 12$^{th}$ day, the tumor volume of the HIF-1α siRNA group was smaller than that of the control group, and the difference was statistically significant (t=15.70, P=0.021<0.05). Thereafter until the nude mice were sacrificed on the 21$^{st}$ day, the tumor volume of the experimental group was smaller than the control group, the difference was statistically significant (17 d: t=17.98, P=0.014<0.05; 21 d: t=17.43, P=0.015<0.05) (Table 2).

TABLE 2

Tumor volume changes of experimental group and control group of nude mice 7, 12, 17 and 21 days after inoculation

| Group | Mean tumor volume (mm3) | | | |
| --- | --- | --- | --- | --- |
| | 7 d after inoculation | 12 d after inoculation | 17 d after inoculation | 21 d after inoculation |
| siRNA Group | 26.35 ± 4.7 | 80 ± 21.9* | 600 ± 210* | 2478 ± 495* |
| Control Group | 20.24 ± 2.9 | 40 ± 10.8 | 280 ± 45 | 1000 ± 156 |

Note:
*P < 0.05 siRNA group compared to control group

Figure 12:
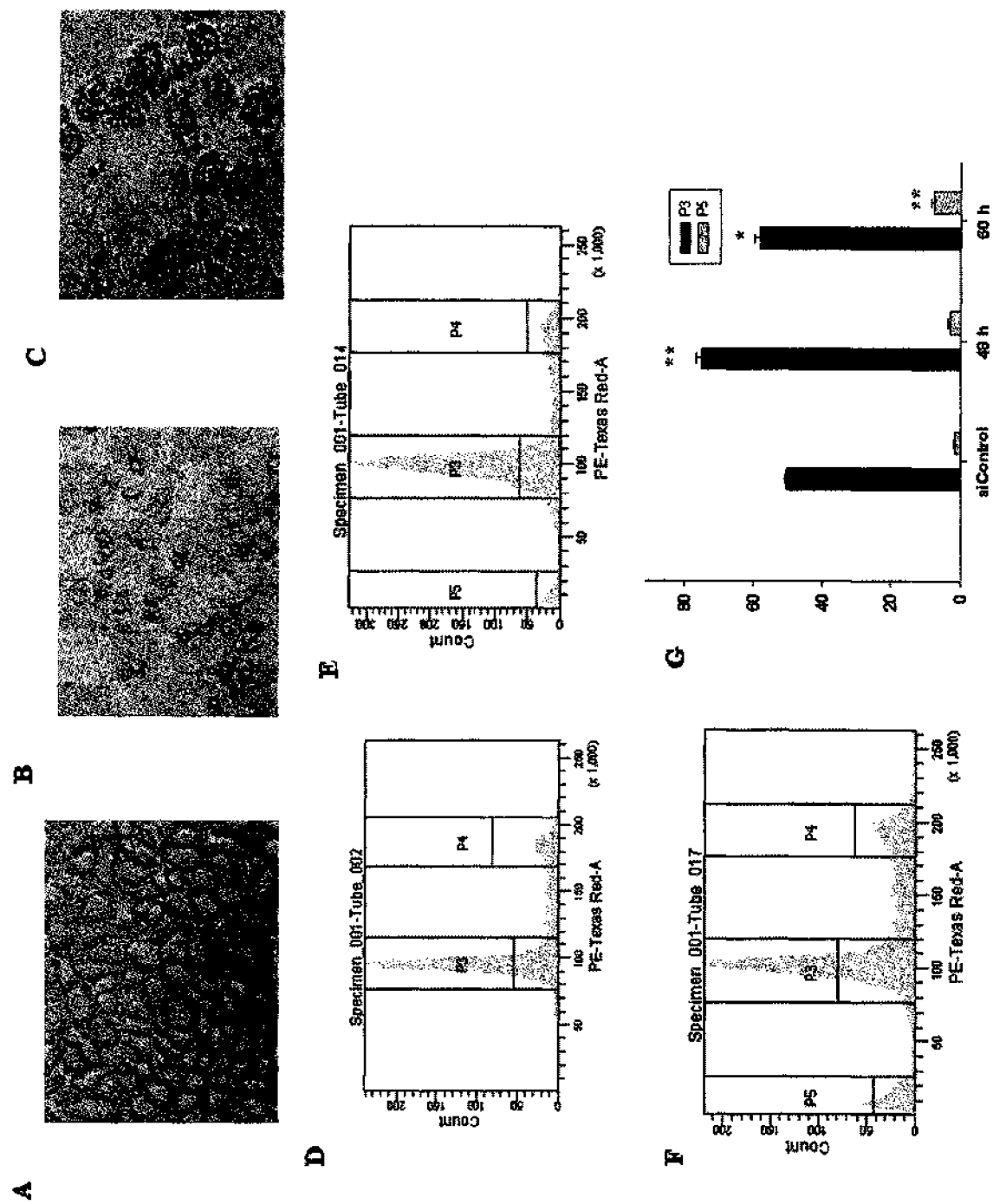
FIG. 12: Effect of interference with VGSC β3 subunit on cell cycle and Cell morphology: A: Image of normal blank HepG2 cell; B: Image of HepG2 cells which were interfered with SCN3B for 48 h; C: Image of HepG2 cells which were interfered with SCN3B for 60 h; D: Cell flow cytometry results of blank HepG2 cells; E: Flow cytometry results of HepG2 cells which were interfered with SCN3B for 48 h; F: Flow cytometry results of HepG2 cells which were interfered with SCN3B for 60 h; G: FIGS. D, E, F, statistical results of integration of p3 peak and p5 peak area, representing cell numbers, wherein p3 is the G0/G1 phase, p5 is the fragment peak (apoptotic peak)
Figure 13:
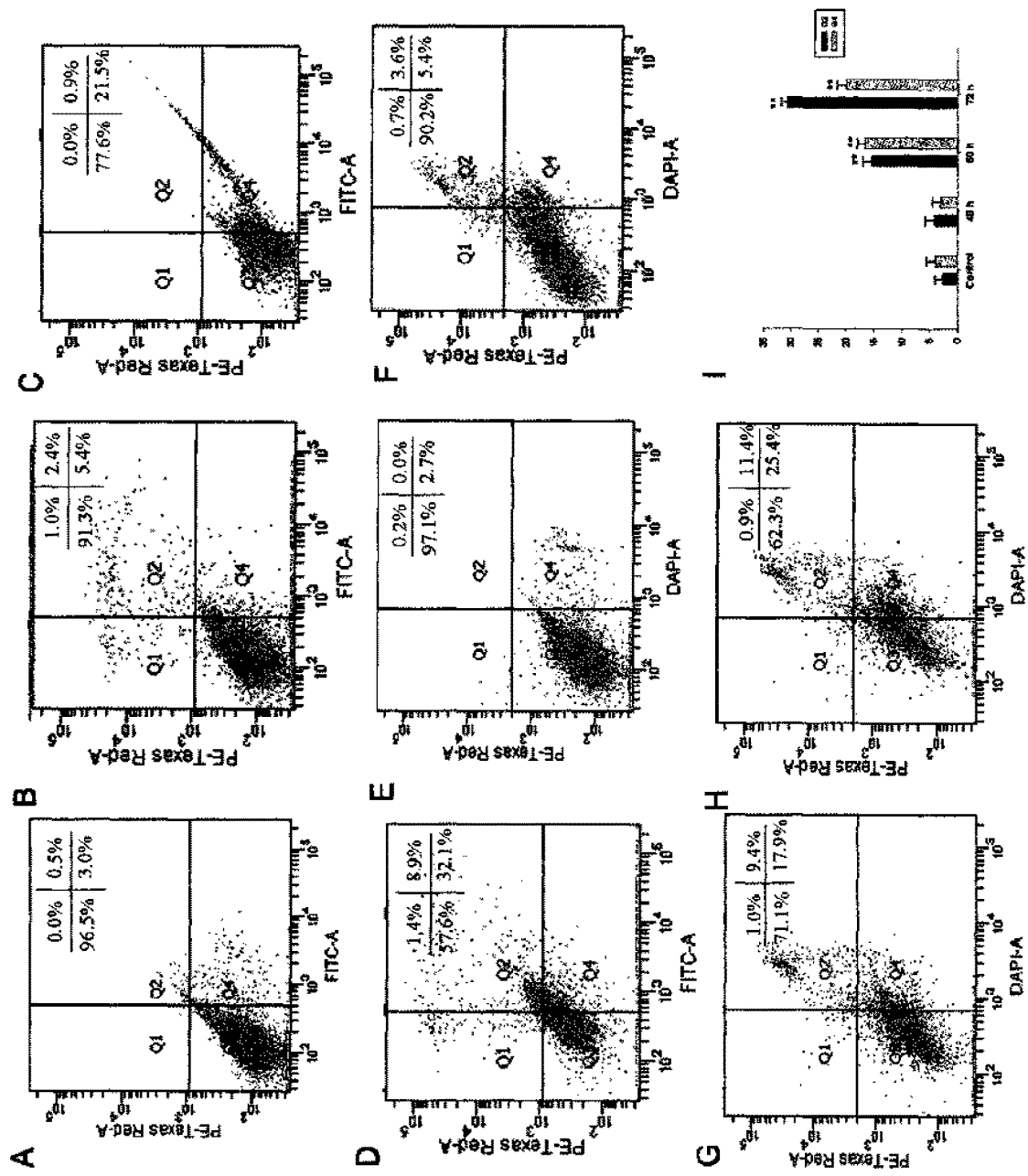
FIG. 13: Effect of VGSCβ3 subunit on apoptosis detected by ANEXIN V.

Example 6. Effect on Cell Morphology and Cell Cycle by Inhibition of VGSC β3 Subunit Expression in HepG2 Cells Interfered HepG2 cells obtained as described in Example 2 were subjected to PI staining as described in PI Mono-Staining Procedure (same method as 2.1.4), counted by flow cytometry (BD FACS Aria™ III), experiment results showed the cell size was decreased after 48 hours of interference, apoptotic bodies and cell debris appeared after 60 hours. Cell cycle was blocked at G0/G1 phase 48 hours after the interference (**P<0.01), the cell cycle blockade was decreased after 60 h (*P<0.05), meanwhile apoptotic peak appeared (*P<0.01) (FIG. 12, p5).

Example 7. Effect on Apoptosis by Inhibition of VGSC β3 Subunit Expression in HepG2 Cells The expression of the VGSC β3 subunit in HepG2 cells was inhibited using two pairs of siRNAs in I.3 as described in Example 2 and the cells were obtained after the interference. The cells were analyzed by flow cytometry after ANEXIN V staining, including the following steps:

1. The cell culture fluid was aspirated to an appropriate centrifuge tube, the attached cells were washed once with PBS, an appropriate amount of pancreatic cell digestion (which can contain EDTA) was added to digest cells.

2. The cells were resuspended in normal medium, mixed, and transferred to the centrifuge tube, centrifuged at 1000 rpm for 5 min, and the supernatant was discarded. The cells were collected, and gently resuspended with PBS and counted.

3. 1 million resuspended cells were taken, centrifuged at 1000 rpm for 5 min, supernatant discarded, 195 μl Annexin V-FITC conjugate solution was added to gently resuspend the cells. 5 μl Annexin V-FITC was added and mixed gently.

4. The cells were incubated for 10 min at room temperature (20 to 25° C.) in the dark. Aluminum foil can be used for protection from light.

5. The cells were centrifuged at 1000 rpm for 5 min, the supernatant was discarded, 190 μl Annexin V-FITC conjugate solution was added to gently resuspend the cells. 10 μl propidium iodide staining solution was added to the cell, gently mixed, and ice bathed and placed in dark place.

6. Flow cytometry was then performed, Annexin V-FITC represented green fluorescence, PI represented red fluorescence.

From the results, it can be seen that the early apoptosis of HepG2 cells took place after 60 h and more late apoptosis (P<0.05, **P<0.01) after 72 h. Thus, it is possible to promote apoptosis by inhibiting the expression of the VGSC β3 subunit in the cells.

The invention claimed is:

1. A method for inhibiting or decreasing tumor cell proliferation, comprising contacting a tumor cell with an amount of a VGSC β3 inhibitor effective to inhibit the expression and/or activity of VGSC β3, wherein the tumor cell is a lung, leukemia or liver cancer tumor cell, wherein the inhibitor of VGSC β3 is analgesic antineoplastic valine (AGAP) or siRNA targeting VGSC β3, and wherein the tumor cell is characterized by an increased expression of VGSC β3 relative to non-cancerous cells,
wherein the siRNA comprises an antisense strand and a sense strand, wherein the antisense strand comprises at least 15 consecutive nucleotides identical to a nucleotide sequence complementary to SEQ ID NO:2.

2. The method of claim 1, wherein the tumor cell is a leukemia tumor cell.

3. The method of claim 1, wherein the tumor cell is a lung or liver cancer tumor cell.

4. The method of claim 3, wherein the tumor cell is HepG2 liver cancer or A549 type lung cancer tumor cell.

5. The method of claim 1, wherein the siRNA has a nucleotide length of 15 bp to 50 bp.

6. The method of claim 1, wherein the siRNA has a nucleotide length of 15 bp to 26 bp.

7. The method of claim 1, wherein the siRNA has a nucleotide length of 15 bp to 36 bp.

8. The method of claim 1, wherein the siRNA has a nucleotide length of 20 bp to 36 bp, wherein the antisense strand comprises a nucleotide sequence at least 95% identical to a nucleotide sequence complementary to 20 or more consecutive nucleotides of SEQ ID NO:2.

9. The method of claim 1, wherein the siRNA has a nucleotide length of 20 bp to 30 bp, wherein the antisense strand comprises a nucleotide sequence at least 95% identical to a nucleotide sequence complementary to 20 or more consecutive nucleotides of SEQ ID NO:2.

10. The method of claim 1, wherein the siRNA has a nucleotide length of 20 bp to 26 bp, wherein the anti sense strand comprises a nucleotide sequence at least 95% identical to a nucleotide sequence complementary to 20 or more consecutive nucleotides of SEQ ID NO:2.

11. The method of claim 1, wherein the siRNA comprises:
a sense strand 5'-CCUGCCUUCAAUAGAUUCUTT-3' (SEQ ID NO:3) and an antisense strand 5'-ACAAUCUAUUGAAGGCAGGTT-3' (SEQ ID NO:4); or
a sense strand 5'-GCGGUAAAGAUUUCCUUAUTT-3' (SEQ ID NO:5) and an antisense strand 5'-AUAAGGAAAUCUUUACCGCTT-3' (SEQ ID NO:6).

* * * * *